United States Patent
Shah

(10) Patent No.: US 9,765,115 B2
(45) Date of Patent: Sep. 19, 2017

(54) INHIBITORS OF METASTASIS, METHODS OF GENERATING SUCH INHIBITORS AND THEIR THERAPEUTIC APPLICATIONS

(75) Inventor: Girish V. Shah, West Monroe, LA (US)

(73) Assignee: Board of Supervisors of Louisiana State University acting on behalf of the University of Louisiana at Monroe, Monroe, LA (US)

( * ) Notice: Subject to any disclaimer, the term of this patent is extended or adjusted under 35 U.S.C. 154(b) by 0 days.

(21) Appl. No.: 14/007,683

(22) PCT Filed: Mar. 30, 2012

(86) PCT No.: PCT/US2012/031532
§ 371 (c)(1),
(2), (4) Date: Jan. 22, 2014

(87) PCT Pub. No.: WO2012/135666
PCT Pub. Date: Oct. 4, 2012

(65) Prior Publication Data
US 2014/0286952 A1    Sep. 25, 2014

Related U.S. Application Data

(60) Provisional application No. 61/470,678, filed on Apr. 1, 2011.

(51) Int. Cl.
| | |
|---|---|
| *C07K 7/08* | (2006.01) |
| *C07K 14/72* | (2006.01) |
| *A61K 38/17* | (2006.01) |
| *G01N 33/50* | (2006.01) |
| *C07K 16/28* | (2006.01) |
| *C07D 233/76* | (2006.01) |
| *A61K 31/4166* | (2006.01) |
| *C12N 15/10* | (2006.01) |

(52) U.S. Cl.
CPC ............ *C07K 7/08* (2013.01); *A61K 31/4166* (2013.01); *A61K 38/1796* (2013.01); *C07D 233/76* (2013.01); *C07K 14/723* (2013.01); *C07K 16/28* (2013.01); *C07K 16/2869* (2013.01); *C12N 15/1055* (2013.01); *G01N 33/5011* (2013.01); *G01N 33/5032* (2013.01)

(58) Field of Classification Search
CPC .... C07K 7/08; C07K 14/723; A61K 38/1796; G01N 33/5011; G01N 33/5032
See application file for complete search history.

(56) References Cited

U.S. PATENT DOCUMENTS

2005/0142541 A1    6/2005 Lu et al. ................ 435/5

OTHER PUBLICATIONS

Anderson, James M. et al., "Tight Junctions," Curr Biol, vol. 18, No. 20, pp. R941-R943 (2008).
Bockaert, J. et al., "GPCR-GIP Networks: A First Step in the Discovery of New Therapeutic Drugs?" Curr Opin Drug Discov Devel, vol. 7, No. 5, pp. 649-657 (2004).
Bockaert, J. et al., "GPCR-interacting proteins (GIPs): nature and functions," Biochem. Soc. Transac, vol. 32, part 5, pp. 851-855 (2004).
Bockaert, Joël et al., "The 'Magic Tail' of G Protein-Coupled Receptors: an Anchorage for Functional Protein Networks," FEBS Letters, vol. 546, pp. 65-72 (2003).
Brennan, Kieran et al., "Tight Junctions: A Barrier to the Initiation and Progression of Breast Cancer?" J Biomed Biotechnol, vol. 2010, Article 460607, pp. 1-16 (2010).
Carr, Daniel W. et al., "Interaction of the Regulatory Subunit (RII) of cAMP-Dependent Protein Kinase with RII-Anchoring Proteins Occurs Through an Amphipathic Helix Binding Motif," J. of Biolog Chem, vol. 266, No. 22, pp. 141880-14192 (1991).
Chen, Minyong et al., "G Protein-Coupled Receptor Kinases Phosphorylate LRP6 in the Wnt Pathway," J Biol Chem, vol. 284, No. 50, pp. 35040-35048 (2009).
Chen, Wen-Ji et al., "Expression Cloning and Receptor Pharmacology of Human Calcitonin Receptors from MCF-7 Cells and Their Relationship to Amylin Receptors," Molecular Pharm., vol. 52, pp. 1164-1175 (1997).
Chien, Jeremy et al., "Calcitonin Is a Prostate Epithelium-Derived Growth Stimulatory Peptide," Mol Cell Endocrinol, vol. 181, pp. 69-79 (2001).
Chien, J. et al., "Constitutive Activation of Stimulatory Guanine Nucleotide Binding Protein ($G_s\alpha QL$)-Mediated Signaling Increases Invasiveness and Tumorigenicity of PC-3M Prostate Cancer Cells," Oncogene, vol. 18, pp. 3376-3382 (1999).
Chigurupati, Srinivasulu et al., "Calcitonin Stimulates Multiple Stages of Angiogenesis by Directly Acting on Endothelial Cells," Cancer Res, vol. 65, No. 18, pp. 8519-8529 (2005).
Conner, A. C. et al., "Heterodimers and Family-B GPCRs: RAMPs, CGRP and Adrenomedullin," Biochem Soc Transac, vol. 32, part 5, pp. 843-846 (2004).
Cui, Hong et al.,"PDZ Protein Interactions Underlying NMDA Receptor-Mediated Excitotoxicity and Neuroprotection by PSD-95 Inhibitors," J. of Neuroscience, vol. 27, No. 37, pp. 9901-9902 (2007).
Denker, Bradley M. et al., "Molecular Structure and Assembly of the Tight Junction," Am J Physiol, vol. 274, pp. 1-9 (1998).
Dong, Maoqing et al., "Importance of the Amino Terminus in Secretin Family G Protein-coupled Receptors. Intrinsic Photoaffinity Labeling Establishes Initial Docking Constraints for the Calcitonin Receptor," J Biol Chem, vol. 279, No. 2, pp. 1167-1175 (2004).
Egerton, M. et al., "Identification of Multiple Human Calcitonin Receptor Isoforms: Heterologous Expression and Pharmacological Characterization," J. Mol Endocrinol, vol. 14, pp. 179-189 (1995).
Fanning, Alan S. et al., "Isolation and Functional Characterization of the Actin Binding Region in the Tight Junction Protein ZO-1," FASEB J., vol. 16, pp. 1835-1837 (2002).

(Continued)

*Primary Examiner* — Ruixiang Li
(74) *Attorney, Agent, or Firm* — John H. Runnels

(57) ABSTRACT

The chain of events that explains calcitonin receptor (CTR)-stimulated invasion and metastasis of prostate cancer cells was identified. The CTR-stimulated events depend on the interaction of CTR with the PDZ3 domain of ZO-1. Small peptides and small molecules were identified that inhibit this interaction. The small inhibitory peptides were synthesized and can be used to attenuate or inhibit metastasis in solid cancer tumors.

14 Claims, 45 Drawing Sheets

(56) References Cited

OTHER PUBLICATIONS

Fanning, Alan S. et al., "The Tight Junction Protein ZO-1 Establishes a Link Between the Transmembrane Protein Occludin and the Actin Cytoskeleton," J Biol Chem, vol. 273, No. 45, pp. 29745-29753 (1998).
Fanning, Alan S. et al., "Zonula Occludens-1 and -2 Are Cytosolic Scaffolds That Regulate the Assembly of Cellular Junctions," *Molecular Structure and Function of the Tight Junction*, Ann. N.Y. Acad. Sci., vol. 1165, pp. 13-120 (2009).
Findlay, D. M., "Regulation of Cell Growth Mediated by the Calcitonin Receptor," Cell Mol Biol, vol. 52, No. 3, pp. 3-8 (2006).
Francis, Sharron H. et al., "Structure and Function of Cyclic Nucleotide-Dependent Protein Kinases," Annu. Rev. Physiol., vol. 56, pp. 237-272 (1994).
Gonzalez-Mariscal, Lorenza et al., "Crosstalk of Tight Junction Components with Signaling Pathways," Biochim Biophys Acta, vol. 1778, pp. 729-756 (2008).
Gonzalez-Mariscal, Lorenza et al., "MAGUK proteins: structure and role in the tight junction," Seminars in Cell & Development Biol, vol. 11, pp. 315-324 (2000).
Hall, Randy A. et al., "Heptahelical Receptor Signaling: Beyond the G Protein Paradigm," J Cell Biol, vol. 145, No. 5, pp. 927-932 (1999).
Hoare, Sam R.J. et al., "Mechanisms of Peptide and Nonpeptide Ligand Binding to Class B G-protein-coupled Receptors," DDT, vol. 10, No. 6, pp. 417-427 (2005).
Huang, C. L. H. et al., "Molecular physiology and pharmacology of calcitonin," Cell Mol Biol, vol. 52, No. 3, pp. 33-43 (2006).
Hurd, Toby W. et al., "Direct Interaction of Two Polarity Complexes Implicated in Epithelial Tight Junction Assembly," Nat Cell Biol, vol. 5, pp. 137-142 (2003).
Katafuchi, Takeshi et al., "Calcitonin Receptor-stimulating Peptide: Its Evolutionary and Functional Relationship with Calcitonin/Calcitonin Gene-related Peptide Based on Gene Structure," Peptides, vol. 30, pp. 1753-1762 (2009).
Khanfar, Mohammad A. et al., "Phenylmethylene Hydantoins as Prostate Cancer Invasion and Migration Inhibitors. CoMFA Approach and QSAR Analysis," European J. of Med. Chem., vol. 45, pp. 5397-5405 (2010).
Kleeff, Jorg et al., "Altered Expression and Localization of the Tight Junction Protein ZO-1 in Primary and Metastatic Pancreatic Cancer," Pancreas, vol. 23, No. 3, pp. 258-265 (2001).
Kohler, Katja et al., "Tight Junction: a Co-ordinator of Cell Signalling and Membrane Trafficking," Biol Cell, vol. 97, pp. 659-665 (2005).
Leve, Fernanda et al., "A Cross-Link Between Protein Kinase A and Rho-Famly GTPases Signaling Mediates Cell-Cell Adhesion and Actin Cytoskeleton Organization in Epithelial Cancer Cells," J Pharmacol Exp Ther, vol. 327, No. 3, pp. 777-788 (2008).
Li, Yuanhe et al., "Structure of the Conserved Cytoplasmic C-terminal Domain of Occludin: Identification of the ZO-1 Binding Surface," J Mol Biol, vol. 352, pp. 151-164 (2005).
Liao, Jinhui et al., "Skeletal Metastasis: Established and Emerging Roles of Parathyroid Hormone Related Protein (PTHrP)," Cancer Metastasis Rev., vol. 25, pp. 559-571 (2006).
Liu, Hong et al., "Proliferation and Polarity in Breast Cancer: Untying the Gordian Knot," eScholarship (Un. of California), Lawrence Berkeley National Laboratory, pp. 1-18 (2005).
Lupp, Amelie et al., "Immunohistochemical Identification of the PTHR1 Parathyroid Hormone Receptor in Nomal and Neoplastic Human Tissues," Eur. J. Endocrinol., vol. 162, pp. 979-986 (2010).
Lynch, Martin J. et al., "RNA Silencing Identifies PDE4D5 as the Functionally Relevant cAMP Phosphodiesterase Interacting with βArrestin to Control the Protein Kinasa A/AKAP79-mediated Switching of the $β_2$-Adrenergic Receptor to Activation of ERK in HEK293B2 Cells," J. of Biolog. Chem., vol. 280, No. 39, pp. 33178-33189 (2005).
Mahon, Matthew J., "The Parathyroid Hormone 1 Receptor Directly Binds to the FERM Domain of Ezrin, an Interaction That Supports Apical Receptor Localization and Signaling in LLC-PK1 Cells," Mol Endocrinol, vol. 23, No. 10, pp. 1691-1701 (2009).
Martin, Tracey A. et al., "Loss of Tight Junction Barrier Function and its Role in Cancer Metastasis," Biochim Biophys Acta, vol. 1788, pp. 872-891 (2009).
Nygaard, Sean C. et al., "Phosphorylation of the Human Calcitonin Receptor by Multiple Kinases is Localized to the C-Terminus," J. of Bone and Mineral REs, vol. 12, No. 10, pp. 1681-1690 (1997).
Pedrew, G.H. et al., "Determination of Protein-Protein Interactions and the Motifs That Mediate Them," Regulation of Gene Expression, Humana Press, pp. 173-176, 184, 199-204, 211-212 (2007).
Purdue, B. W. et al., "Molecular Pharmacology of the Calcitonin Receptor." Receptors and Channels, vol. 8, pp. 243-255 (2002).
Ritchie, Candace K. et al., "Effects of the calciotrophc peptides calcitonin and parathyroid hormone on prostate cancer growth and chemotaxis," The Prostate, vol. 30, No. 3, pp. 183-187 (1997).
Ritchie, Candace K. et aL., "The Effects of Growth Factors Associated with Osteoblasts on Prostate Carcinoma Proliferation and Chemotaxis: Implications for the Development of Metastatic Disease," Endocrinology, vol. 138, No. 3, pp. 1145-1150 (1997).
Sabbisetti, Venkata S. et al., "Calcitonin Increases Invasiveness of Prostate Cancer Cells: Role for Cyclic AMP-Dependent Protein Kinase A in Calcitonin Action," Int J Cancer, vol. 117, pp. 551-560 (2005).
Schwab, Manfred, Encyclopedia of Cancer, $2^{nd}$ Edition, Springer-Verlag Berlin Heidelberg New York, p. 445 (2008).
Shah, G. V., "Calcitonin," Encyclopedia of Cancer, vol. 2, pp. 16-20 (2009).
Shah, Girish V. et al., "Calcitonin Stimulates Growth of Human Prostate Cancer Cells Through Receptor-Mediated Increase in Cyclic Adenosine 3',5'-Monophosphates and Cytoplasmic $Ca^{2+}$ Transients," Endocrinology, vol. 134, No. 2, pp. 596-602 (1994).
Shah, Girish V. et al., "Calcitonin Promotes in vivo Metastasis of Prostate Cancer Cells by Altering Cell Signaling, Adhesion, and Inflammatory Pathways," Endocr Relat Cancer, vol. 15, pp. 953-964 (2008).
Shah, Girish V. et al., "Cadherin Switching and Activation of β-Catenin Signaling Underlie Proinvasive Actions of Calcitonin-Calcitonin Receptor Axis in Prostate Cancer," J Biol Chem, vol. 284, No. 2, pp. 1018-1030 (2009).
Shah, Girish V. et al., "Identification of a Small Molecule Class to Enhance Cell-Cell Adhesion and Attenuate Prostate Tumor Growth and Metastasis," Mol Cancer Ther, vol. 8, No. 3, pp. 509-520 (2009).
Shan, Girish V. et al., "Identification of a Small Molecule Class to Enhance Cell-Cell Adhesion and Attenuate Prostate Tumor Growth and Mestatasis," Mol. Cancer Ther, vol. 8, No. 3, pp. 509-520 (2009).
Shin, Kunyoo et al., "Tight Junctions and Cell Polarity," Annu. Rev. Cell Dev. Biol., vol. 22, pp. 207-235 (2006).
Tao, Yuan-Xiang et al., "Neuronal Pdz Domains: A Promising New Molecular Target for Inhaled Anesthetics?" Mol Interv, vol. 4, iss. 4, pp. 215-221 (2004).
Thiery, Jean Paul et al., "Complex Networks Orchestrate Epithelial-Mesenchymal Transitions," Nature Rev, Molec. Cell Biol., vol. 7, pp. 131-142 (2006).
Thomas, Shibu et al., "Calcitonin Increases Tumorigenicity of Prostate Cancer Cells: Evidence for the Role of Protein Kinase A and Urokinase-Type Plasminogen Receptor," Mol Endocrinol, vol. 20, No. 8, pp. 1894-1911 (2006).
Thomas, Shibu et al., "Calcitonin Induces Apoptosis Resistance in Prostate Cancer Cell Lines Against Cytotoxic Drugs via the Akt/Survivin Pathway," Cancer Biol & Ther, vol. 4, No. 11, pp. 1226-1233 (2005).
Thomas, Shibu et al., "Calcitonin Receptor-Stimulated Migration of Prostate Cancer Cells is Mediated by Urokinase Receptor-Integrin Signaling," Clin Exp Metastasis, vol. 24, pp. 363-377 (2007).
Thomas, Shibu et al., "Knock-Down of Calcitonin Receptor Expression Induces Apoptosis and Growth Arrest of Prostate Cancer Cells," Int J Oncol, vol. 31, pp. 1425-1437 (2007).

(56) References Cited

OTHER PUBLICATIONS

Tovar Sepulveda, Veronica A. et al., "Parathyroid Hormone-Related Protein Enhances PC-3 Prostate Cancer Cell Growth via Both Autocrine/Paracrine and Intracrine Pathways," Regul. Pept., vol. 105, pp. 109-120 (2002).

Troyanovsky, Regina B. et al., "Removal of Calcium Ions Triggers a Novel Type of Intercadherin Interaction," J. of Cell Science, vol. 112, pp. 4379-4387 (1999).

Turley, Eva A. et al., Mechanisms of Disease: Epithelial—mesenchymal Transition—Does Cellular Plasticity Fuel Neoplastic Progression? Nat Clin Pract Oncol, vol. 5, No. 5, pp. 280-290 (2008).

Van Itallie, Christina M. et al., "The Role of Claudins in Determining Paracellular Charge Selectivity," Proc Am Thorac Soc, vol. 1, pp. 38-41 (2004).

Wong, Wei et al., "AKAP Signalling Complexes: Focal Points in Space and Time," Molecular Cell Biol, vol. 5, pp. 959-970 (2004).

Zahraoui, Ahmed., "Les jonctions serrées: Plate-forme de régulation de la prolifération et de la polarité cellulaires" ("Tight junctions, a platform regulating cell proliferation and polarity"), Medicine/Sciences Paris, vol. 20, pp. 580-585 (2004) [with abstract translation].

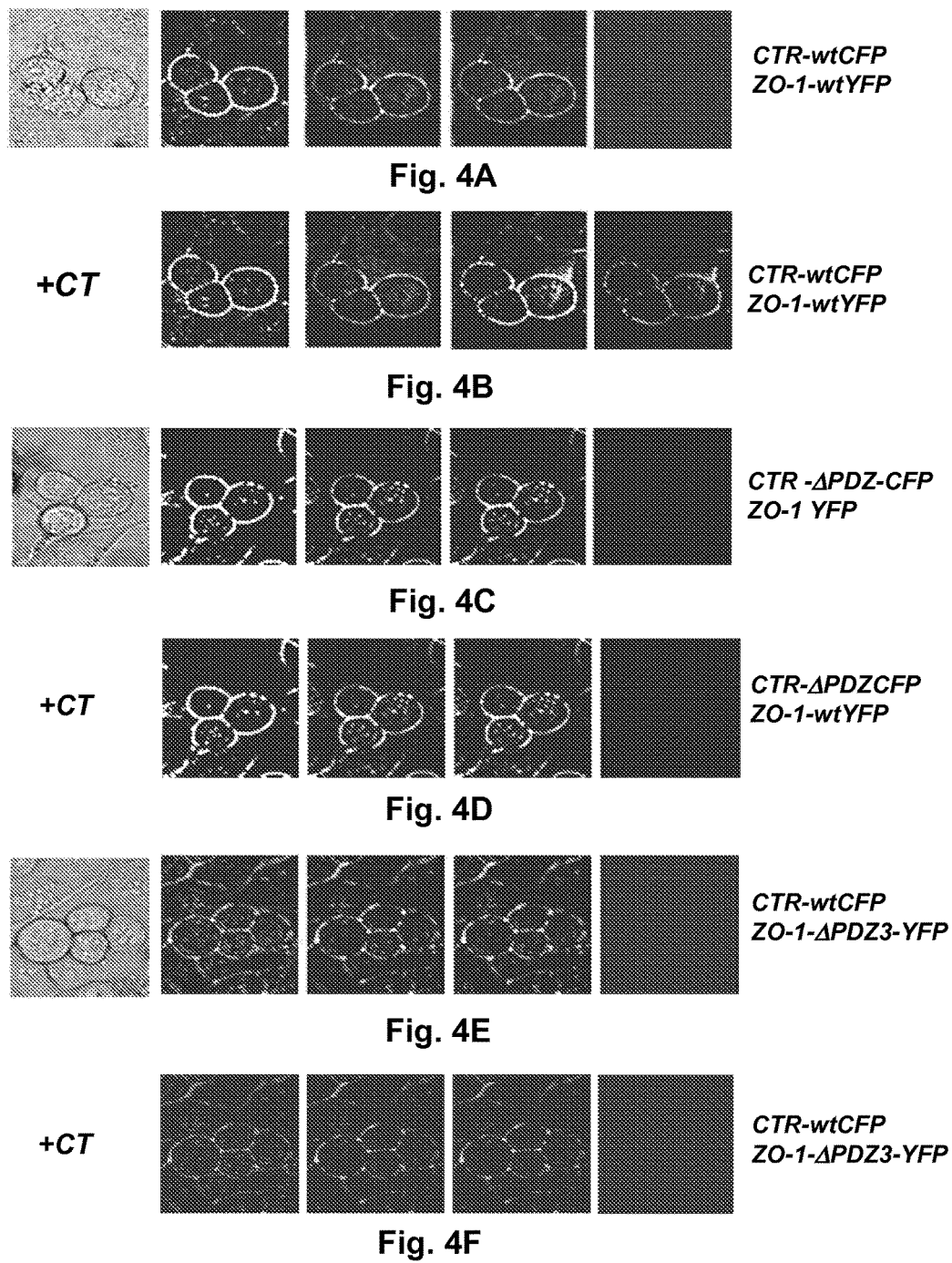

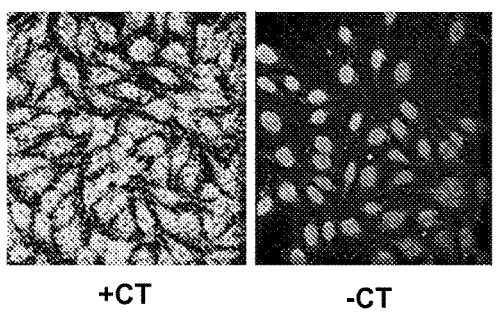
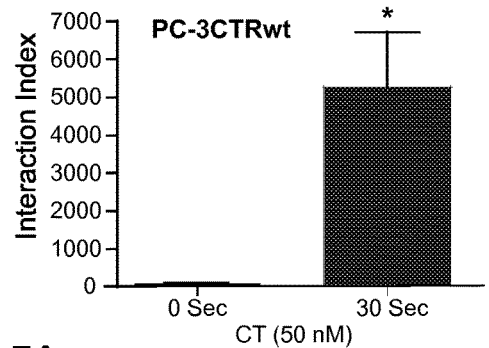
Fig. 7A
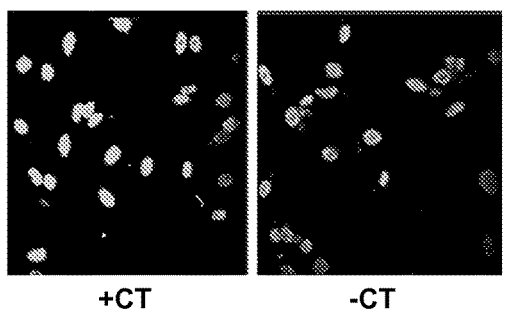
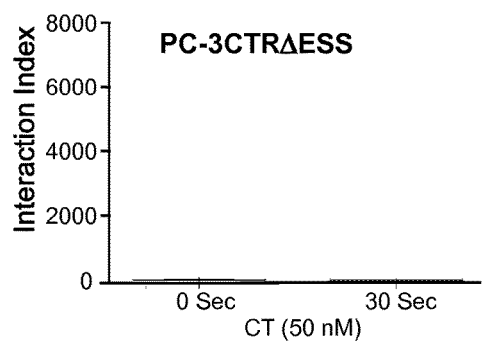
Fig. 7B
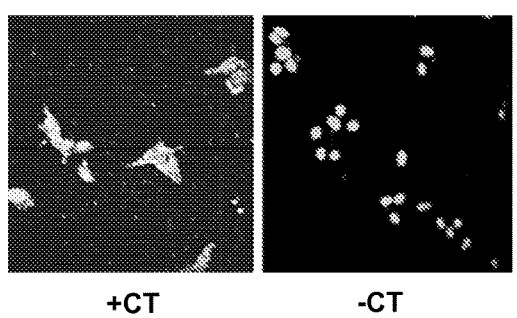
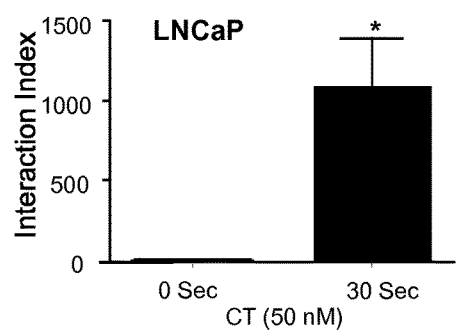
Fig. 7C

PC3-CTR membranes
10 µg   20 µg   40 µg

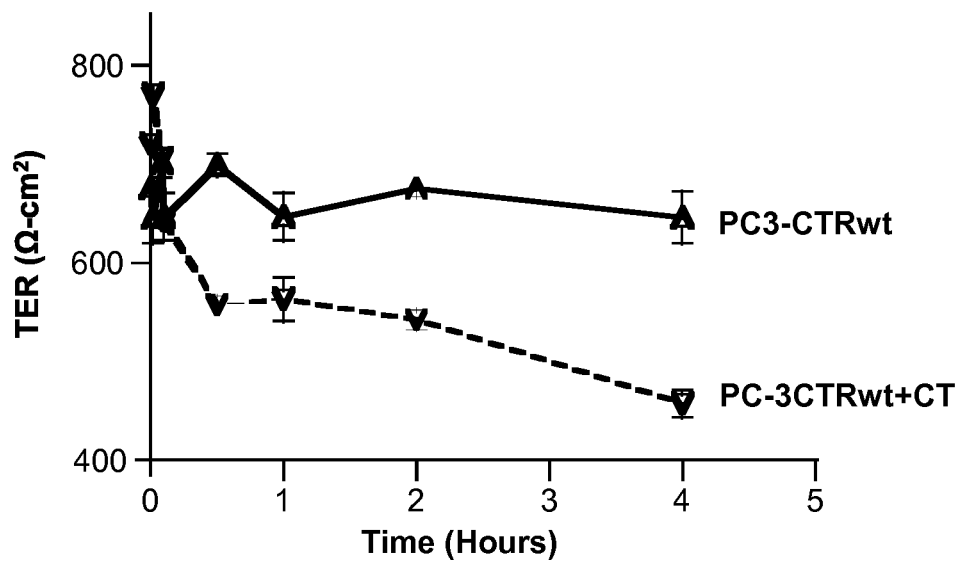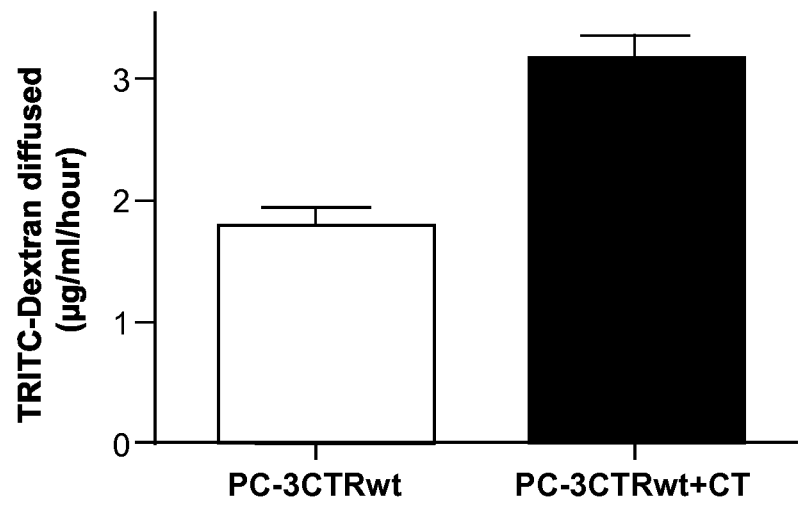
Fig. 15A

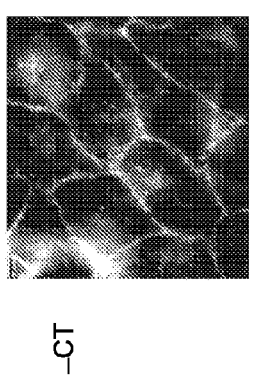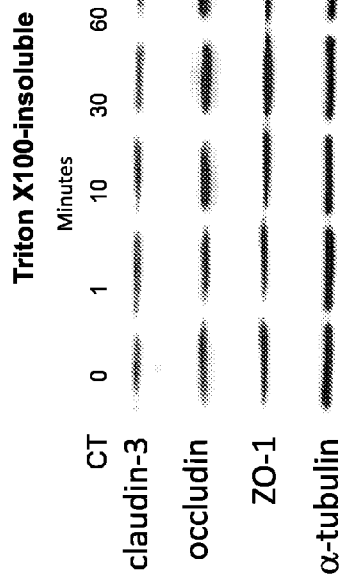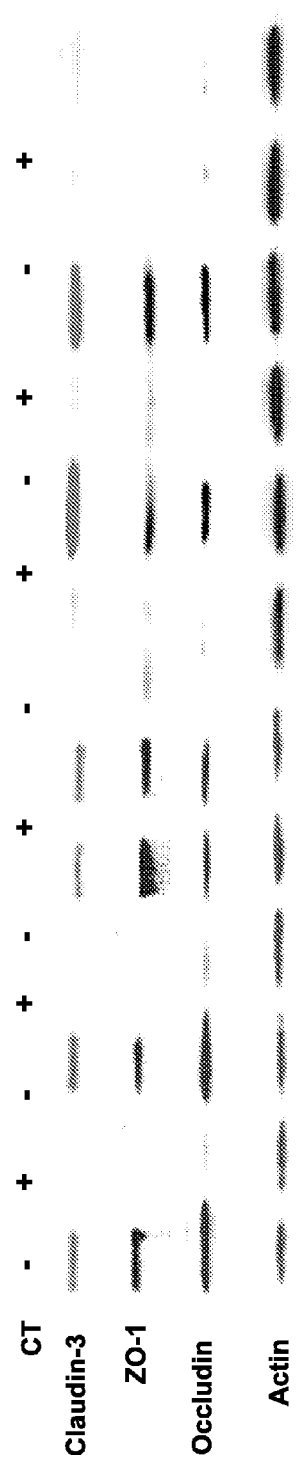
Fig. 19A
Fig. 19B
Fig. 19C

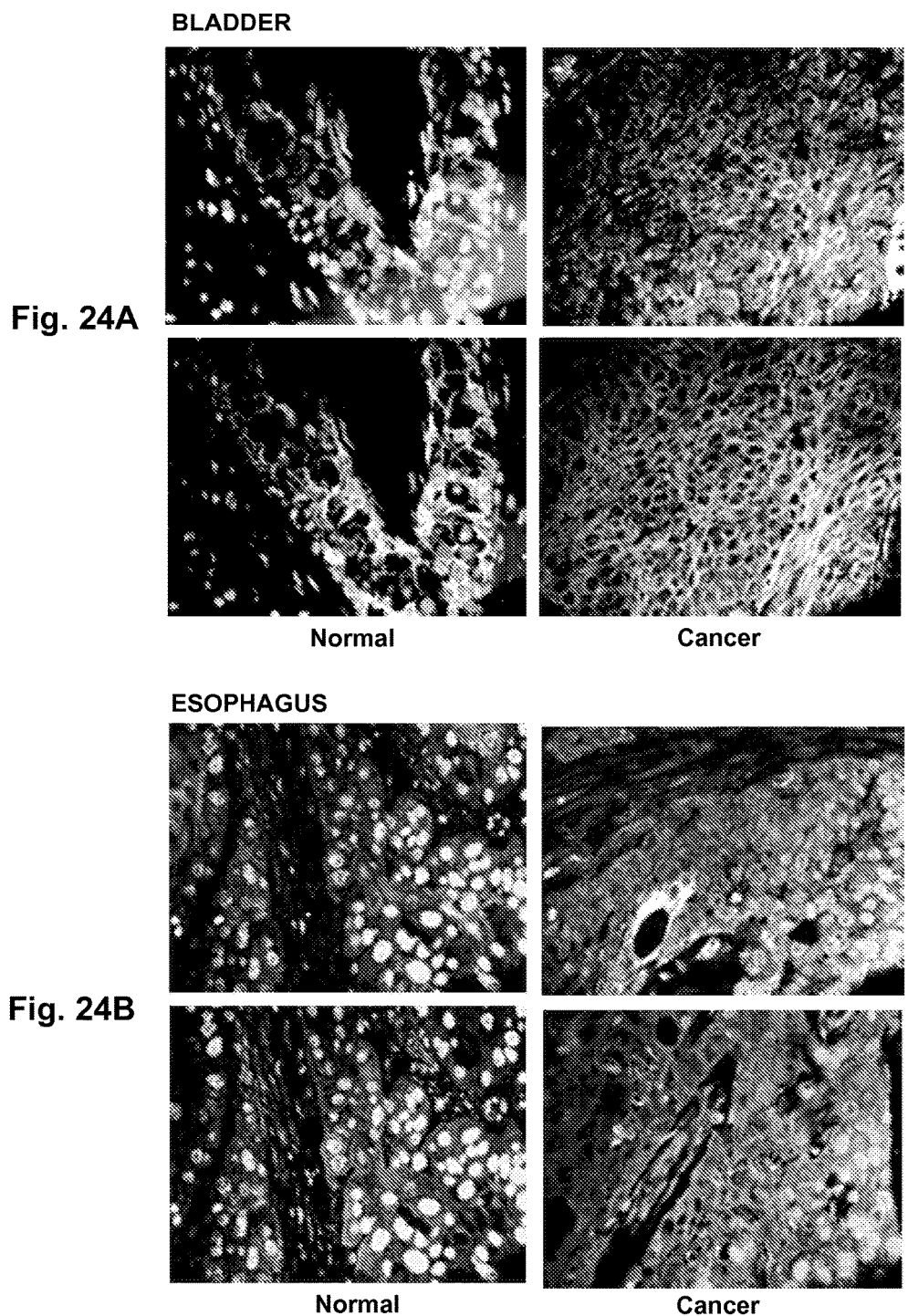
Fig. 24A BLADDER — Normal / Cancer
Fig. 24B ESOPHAGUS — Normal / Cancer Amino Acid Sequence for PDZ1 (SEQ ID NO:9):

TVTLHRAPGFGFGIAISGGRDNPHFQSGETSIVISDVLKGGPAEGQLQENDRVAMVNGVSMDNVEHAFAVQQLRKSGKNAKITIRRKK

Amino Acid Sequence for PDZ2 (SEQ ID NO:10):

KVTLVKSRKNEEYGLRLASHIFVKEISQDSLAARDGNIQEGDVVLKINGTVTENMSLTDAKTLIERSKGKLKMVVQRDE

Amino Acid Sequence for PDZ3 (SEQ ID NO:11):

SMKLVKFRKGDSVGLRLAGGNDVGIFVAGVLEDSPAAKEGLEEGDQILRVNNVDFTNIIREEAVLFLLDLPKGEEVTILAQK

Fig. 29

INHIBITORS OF METASTASIS, METHODS OF GENERATING SUCH INHIBITORS AND THEIR THERAPEUTIC APPLICATIONS

This is the United States national stage of international application PCT/US2012/031532, international filing date Mar. 30, 2012, which claims the benefit of the filing date of provisional U.S. application Ser. No. 61/470,678, filed Apr. 1, 2011, under 35 U.S.C. §119(e).

This invention was made with government support under grant No. CA096534 awarded by the National Institutes of Health. The government has certain rights in this invention.

TECHNICAL FIELD

This invention pertains to inhibitors of cancer metastasis and methods of identifying inhibitors for therapeutic application, for example, inhibitors designed to disrupt the PDZ domain of zonula occludins-1 (ZO-1) and inhibit the interaction between calcitonin receptor and ZO-1. Such inhibitors will stabilize tight junctions, and thus cell adhesion, between cancer cells, and prevent metastasis.

BACKGROUND

Metastasis or spread of cancer cells to locations other than the primary location is the primary cause of death due to cancer. The mechanism of metastasis is not well understood and there are very few drugs or inhibitors that block the process effectively. Most drugs or other therapies for treating cancer are aimed at killing the cancer cells and often kill many normal cells leading to adverse side effects. Some drugs are designed to block the growth of tumors or their blood supply (e.g., inhibit angiogenesis), but these drugs are often marginally effective and interfere with normal physiologic functions, again leading to adverse side effects.

Epithelial-to-mesenchymal transition (EMT) for cells occurs during normal development and at the beginning of epithelial cancers in which the cells acquire an invasive or migratory phenotype (Liu, Radisky et al. 2005; Turley, Veiseh et al. 2008). This change is characterized by the loss of cell-cell adhesion and cytoskeletal rearrangement (Thiery and Sleeman, 2006). Epithelial cell-cell adhesion is predominantly maintained by the apical junction complex (AJC), which is formed by tight junctions (TJs) and adherens junctions (AJs) (Troyanovsky, Klingelhofer et al. 1999). Tight Junctions (TJs) are formed when integral membrane proteins (e.g., the claudin family of proteins and occludins) and junctional adhesion molecules (JAMs) interact with adaptor proteins of the zonula occludens (ZO) family (e.g., ZO-1, ZO-2 and ZO-3) to link TJs with the actin cytoskeleton (Shin, Fogg et al. 2006; Fanning and Anderson 2009). TJs are deregulated in EMT. TJ proteins have been reported to exert major influence over mechanisms that regulate cell polarity, differentiation and migration; and all these processes are central to cancer progression (Brennan et al.; Martin and Jiang, 2009)

Protein Kinase A (PKA), a serine/threnoine kinase, is activated by increased levels of cyclic AMP (cAMP) in localized microdomains and catalyzes key cellular processes such as metabolism, gene transcription, ion channel conductivity, cell growth, cell division and actin cytoskeleton rearrangements (Carr, Stofko-Hahn et al. 1991; Francis and Corbin 1994). Given the broad spectrum of signaling events controlled by PKA, the fidelity of PKA action is tightly regulated by spatial mechanisms that target PKA toward its substrate and by temporal mechanisms involving phosphodiesterases that degrade cAMP to limit the duration of the cellular effects of PKA (Wong and Scott 2004; Lynch, Baillie et al. 2005). Zonula occludens-1 (ZO-1), a scaffolding protein with multiple interaction domains, has been shown to recruit protein kinases, phosphatases, small guanine triphosphatases (GTPases), and transcription factors to the TJ complex (Gonzalez-Mariscal, Tapia et al. 2008). This leads to the juxtaposition of structural (actin and spectrin) and regulatory (actin-binding proteins, GTPases, kinases) proteins with transmembrane proteins (Gonzalez-Mariscal, Betanzos et al. 2000; Kohler and Zahraoui 2005), facilitating interactions among them. PKA signaling regulates both the assembly and opening of the paracellular route in epithelial and endothelial cells (Gonzalez-Mariscal, Tapia et al. 2008). Although PKA seems to enhance TJ assembly and barrier function in normal epithelial cells, PKA has been shown to activate RhoA, a founding member of the small Rho GTPase family, at the apical side of the cell to promote TJ disassembly, increased paracellular permeability, loss of TJ functionality, and actin disorganization in apical and medial regions of epithelial cancer cells (Leve, de Souza et al. 2008).

Higher TJ protein phosphorylation reduces TJ functionality (Singer, Stevenson et al. 1994). ZO-1 is a member of the membrane-associated guanylate kinase (MAGuK) family of large scaffolding and signaling proteins that share several protein-binding domains including three PDZ domains, a SRC homology domain (SH3), and a GUK domain (Fanning et al., 2002; Fanning and Anderson 2009). ZO-1 is a major scaffolding protein and a key organizer of TJs at the plasma membrane (Fanning et al., 2002; Li et al., 2005). ZO-1 binds directly with occludin, claudins and junction adhesion molecules (JAMs) to form TJs (Anderson and Van Itallie, 2008; Denker and Nigam, 1998); associates with other proteins that regulate epithelial cell polarity and paracellular permeability; and serves as a bridge between cell surface and actin cytoskeleton (Fanning et al., 1998; Hurd et al., 2003; Van Itallie and Anderson, 2004; Zahraoui, 2004).

Calcitonin receptor (CTR) is a member of the class B family of G Protein-coupled receptors (GPCRs), which contain numerous drug targets (Conner et al., 2004; Dong et al., 2004). CTR binds calcitonin (CT) and other ligands of the CT family to maintain calcium homeostasis in the bone and the kidneys (Katafuchi et al., 2009; Purdue et al., 2002). However, CTR expression in multiple organs and its actions on cell growth and differentiation demonstrates that CTR has a more diverse role than just the maintenance of calcium homeostasis (Findlay, 2006; Huang et al., 2006; Shah, 2009). The expression of CT and CTR is up-regulated in metastatic prostate cancer (PC) (Thomas, Chiriva-Internati et al. 2007; Shah 2009; Chien et. al., 2001b). Activation of the autocrine CT-CTR axis increases cell proliferation, chemo-resistance, and invasiveness of prostate cancer cell lines (Ritchie, Thomas et al. 1997; Thomas and Shah 2005; Thomas, Chigurupati et al. 2006; Thomas, Chiriva-Internati et al. 2007; Thomas, Muralidharan et al. 2007). Moreover, CTR destabilizes tight junctions (TJs) as assessed by trans-electric epithelial resistance (TER) and paracellular permeability (PCP) of multiple prostate cancer cell lines (Shah et al., 2009). Two small molecules, phenyl-methylene hydrantoin (PMH) and its S-ethyl derivative (S-PMH) were found to enhance cell-cell adhesion and attenuate prostate tumor growth and metastasis, and were noted to be potential drug candidates for CT-positive androgen-independent prostate cancers (Shah et al., 2009).

Human CTR (hCTR) exists in three or more isoforms formed by alternative splicing of the same primary transcript (Egerton et al., 1995). Recent studies suggest selective expression of isoform 2 of hCTR (hCTR2) in basal, but not luminal, epithelium of human prostate cells (Chien et al., 2001b; Shah et al., 1994). However, this spatial specificity is lost in malignancy, and the abundance of CTR transcripts is increased with tumor progression. CTR stimulates several processes associated with tumor growth, invasion, angiogenesis and metastasis. CTR serves as an important factor in the progression of a localized prostate cancer to its metastatic form (Chigurupati et al., 2005; Sabbisetti et al., 2005; Shah et al., 2008; Thomas et al., 2006).

hCTR2 lacks an 16-amino acid insert in the first intracellular loop, which enables it to couple to both stimulatory GTP binding protein ($G_a$s) and $G_a$q. In addition, CTR destabilizes tight and adherens junctions and activates non-G protein-coupled signaling pathways such as phosphoinositide-3-kinase (PI3K)-Akt-survivin and WNT/b-catenin (7,13). (Shah et al., 2009a; Thomas and Shah, 2005). Class B G protein-coupled receptors (GPCRs) may also activate non-G protein-mediated signaling (Chen et al., 2009; Hall et al., 1999). For example, cytoplasmic tails of some GPCRs interact with scaffolding proteins through protein-interacting domains such as SRC homology 2 (SH2) or PSD-95-disc large-zonnula occludens (PDZ) to regulate receptor-mediated signal transduction, receptor regulation, or receptor biosynthesis (Bockaert et al., 2004). The four C-terminal residues of CTR (aa 471-74, E-S-S-A (SEQ ID NO:1) form a canonical type I PDZ domain-binding motif, which may allow it to interact with a PDZ containing scaffolding protein(s) to activate non-G protein-mediated signaling (Bockaert et al., 2003; Tao and Johns, 2004). Other receptors are known that also contain C-terminal PDZ-binding motif, for example, parathyroid hormone (PTH) receptor and adrenergic receptors. Moreover, PTH receptor has been found to be up-regulated in prostate cancer and may be associated with skeletal metastasis. (Mahon, 2009; Lupp et al., 2010; Liao et al., 2006; and Tovar et al., 2002)

Although calcitonin receptor (CTR) activates multiple signaling pathways that may mediate multiple effects of CTR on prostate cancer cells, $G_a$s-activated signaling plays an important role in its proinvasive actions. For example, constitutive activation of $G_a$s mimics CTR-induced increase in metastasizing capacity of prostate cancer cells, and inhibitors of cAMP-dependent protein kinase (PKA) attenuate CTR-mediated invasion of prostate cancer cells (Chien, Wong et al. 1999; Sabbisetti, Chirugupati et al. 2005). However, the precise mechanism by which CTR stimulates prostate cancer metastasis has not been previously identified.

Pancreatic cancer cell lines with activated CT-CTR autocrine axis such as PC-3M and DU-145 cells display greater invasiveness and metastatic potential than cell lines with inactive CT-CTR autocrine axis such as LNCaP and PC-3 cells (Thomas, 2006). LNCaP and PC-3 cells acquire or increase invasive phenotype with activation of CT-CTR autocrine axis (Thomas, 2006). In contrast, PC-3M cells lose their invasive phenotype with knock-down of either CT or CTR expression (Shah et al., 2009; Thomas et al., 2006). Anti-sense CT ribozyme therapy inactivates CT-CTR axis in LPB-Tag transgenic mice, also sharply reducing growth of spontaneously induced prostate tumors (Shah et al., 2008).

DISCLOSURE OF THE INVENTION

I have discovered that calcitonin receptor (CTR) interacts with zonula occludins-1 (ZO-1) leading to the destabilization of Tight Junctions (TJ) and the dissemination of malignant cells (i.e., metastatic cells). I have also developed two peptides that disrupt the interaction between the PDZ motif of ZO-1 and the PDZ binding domain of CTR. These peptides were shown to inhibit cell invasion. I have also discovered a method to identify and develop inhibitors that block the interaction between CTR, or any similar receptor that induces invasion or metastasis, and ZO-1 directly or indirectly leading to abrogation of the process of dissemination of malignant cells and therefore preventing or ameliorating metastasis. The disruption of the CTR-ZO-1 interaction can also be achieved by neutralizing or antagonizing CTR or its ligand, calcitonin.

The role of CTR-C PDZ-binding motif on CTR-induced destabilization of tight junctions (TJs) and invasion of prostate cancer cells was tested; and the interacting protein that mediates these actions was identified. CTR-C PDZ-binding motif was shown to interact with the intracellular tight junction (TJ) protein zonula occludins-1 (ZO-1), and this interaction was critical for the actions of CTR on TJ destabilization as well as orthotopic tumor growth and metastasis of prostate cancer cells.

Both CTR-ZO-1 interaction through PDZ domain and activation of cAMP-dependent protein kinase (PKA) were found to be necessary for CTR-stimulated TJ disassembly, loss of cell adhesion, and thus cell invasion. ZO-1, by interacting with CTR, recruits the receptor to TJ complex, where the CTR may activate the localized PKA to phosphorylate ZO-1 and claudin 3. PKA-mediated phosphorylation of these proteins seems to disengage ZO-1 from integral membrane proteins, leading to rapid TJ disassembly and endocytosis of TJ proteins. CTR-mediated phosphorylation of TJ proteins was shown to be prevented by the blockade of CTR-ZO-1 interaction. I have shown that the CTR-C terminal PDZ-binding motif is required for this interaction, and mutation of this motif abrogates the action of CT TJ disassembly, invasion and metastasis. The CTR-C terminal PDZ binding motif (ESSA; SEQ ID NO:1) is a Class I PDZ binding motif because it satisfies the generic formula as "X-S/T-X-Ø", where X—is any amino acid; S/T means either S or T; and Ø means any hydrophobic acid.

A major discovery is the importance of CTR-ZO-1 interaction in providing spatio-temporal specificity to CTR-stimulated PKA activation. The mutation of the CTR-C PDZ-binding motif completely prevented CTR-ZO-1 interaction, but did not affect either CT-induced cAMP accumulation or the activation of PKA. CTR-induced TJ disassembly and endocytosis of TJ proteins was shown to require both CTR-C PDZ-binding motif and activated PKA.

The direct role of PKA in CTR-induced disassembly of TJs was demonstrated by showing that calcitonin (CT) stimulated phosphorylation of serines/threonines in ZO-1 and claudin-3; and this phosphorylation was blocked by mPKI. Five potential PKA substrates on ZO-1 molecule are distributed between PDZ1-PDZ2, PDZ2-PDZ3, and GUK-ZU5 domains as well as within GUK domain. Destabilization of a segment between PDZ1 and PDZ2 or between GUK and ZU5 domains lead to dissociation of claudins or severance of linkage of TJ complex with actin cytoskeleton. The amino acid sequences for the three PDZ domains are shown in FIG. 29 (PDZ1—amino acid sequence SEQ ID NO:9; PDZ2—amino acid sequence SEQ ID NO:10; PDZ3—amino acid sequence SEQ ID NO:11) CTR-ZO-1 interaction was shown to enable selective activation of localized PKA in TJ complex, which leads to phosphorylation of key TJ proteins such as ZO-1 and Claudin-3. Phosphorylation of these proteins leads to TJ disassembly, consequently increasing the invasive and metastatic capacity of prostate cancer cells. This process was found to be rapid, with CTR-ZO-1 interaction within 30 seconds of CTR activation, and ZO-1 endocytosis beginning soon thereafter.

CTR-ZO-1 interaction was attenuated by use of synthetic peptides carrying the PDZ-binding motif and delivering the peptides inside the cell. The two peptides were the following: Peptide I (PepI): N-EQESSAAYGRKKRRQRRR-C (SEQ ID NO:2); and Peptide II (PepII): N-IIEQES-SAYGRKKRRQRRR-C(SEQ ID NO:3). The prevention of CTR-ZO-1 interaction thus can significantly impact invasiveness of prostate cancer. These peptides may be used for a therapeutic approach for advanced prostate cancer, or other metastatic cancers than depend on a similar CTR-ZO-1 interaction for metastasis to occur. The ZO-1-PDZ3 domain was identified as the site of CTR-ZO-1 interaction.

This invention relates not only to the two peptides above as described in this specification, but also to peptides having modifications to such a sequence resulting in an amino acid sequence having the same function (i.e., a functional peptide that inhibits the CTR-ZO-1 interaction), and about 80%, preferably 85%, more preferably 90%, and most preferably 95% or greater homology to the sequence of the amino acid sequence as described. "Homology" as used here means identical amino acids or conservative substitutions (e.g., acidic for acidic, basic for basic, polar for polar, nonpolar for nonpolar, aromatic for aromatic). The degree of homology can be determined by simple alignment based on programs known in the art, such as, for example, GAP and PILEUP by GCG, or the BLAST software available through the NIH internet site. Most preferably, a certain percentage of "homology" would be that percentage of identical amino acids.

The interaction of CTR with ZO-1 was observed in androgen-responsive as well as androgen-resistant prostate cancer cell lines, and CTR also produced similar effects in these cell lines. Remarkable differences was found in the expression of CT, CTR and CTR-ZO-1 interactions in metastatic and non-metastatic prostate cancer specimens of similar tumor stage, suggesting that the elevation of CT, CTR expression, and CTR-ZO-1 interactions may also serve as early markers of metastatic disease.

The role of CTR-C PDZ-binding motif on orthotopic growth of metastasis of PC-3 cells was tested in nude mice. The PC-3 cell line was chosen because it was the only cell line that lacked endogenous CTR among several PC cell lines that were tested for CT/CTR expression (Chien et al., 2001a). It allowed the expression of either wildtype (wt) or mutant forms of CTR without the interference of endogenous CTR. The results showed that the mutation of the PDZ-binding motif led to almost complete loss in the ability of PC-3 cells to form orthotopic tumors and distant metastases and demonstrate the importance of CTR-ZO-1-TJ axis in CTR-stimulated tumor growth and metastasis. Thus, the importance of PDZ interaction in the formation of CTR-ZO-1 complex to promote tumor growth and metastasis was shown.

While CTR-PDZ domain interaction is critical for metastasis of prostate cancer cells, this finding is not unique for CTR or for prostate cancer. Other receptors that induce invasion or dissemination of malignant cells through disassembly of tight junctions may act through the same mechanism and the disruption of this interaction would lead to abrogation of metastasis. Other receptors known to contain C-terminal PDZ-binding motif are parathyroid hormone (PTH) receptor and adrenergic receptors. Moreover, PTH receptor has been shown to be up-regulated in prostate cancer and may be associated with skeletal metastasis. Such receptors with PDZ-binding motif similar to the CTR-C PDZ binding motif may bind to ZO-1 and destabilize tight junctions to increase metastasis as we have observed in case of calcitonin receptor. Thus drugs can be identified and developed that can inhibit metastasis by disrupting receptor-ZO-1 interaction in cases where the receptor induces invasion or dissemination of tumor cells by binding to the PDZ domains of ZO-1 leading to disassembly of TJs. The yeast 2-hybrid (Y2H) complementation screening assay and the GST-pulldown assay described below is a good system to screen for small molecules that can disrupt the interaction between ZO-1 PDZ motif and CTR (or similar receptors capable of destablizing TJs by binding to ZO-1). The small molecule compounds to be screened can be obtained through standard combinatorial chemisty techniques, from a large library of compounds, or by in-silico modeling based on the predicted structure of the PDZ domain of ZO-1.

Solid cancers other than prostate cancer were also found to employ the same mechanism, i.e., receptor-ZO-1 interaction leading to disruption of TJs and dissemination of cancer cells. Drugs that disrupt receptor-ZO-1 interaction through the PDZ domain would be therapeutically active against pancreatic cancer or for any solid tumors by inhibiting their metastatic potential or increasing angiogenesis in prostate or ovarian cancer cells.

I have shown multiple lines of evidence that CTR-ZO-1 interaction is through the PDZ domain of ZO-1 and is critical for destablization of TJ and the induction of invasion in cells and metastasis in animal models. Various inhibitors (PepI, PepII and hydantoin molecules) have been identified that can block the interaction between CTR and ZO-1. This interaction can also be blocked by using a monoclonal antibody against CTR or CT or by screening and identifying a small molecule antagonist of CTR. Such molecules would act as therapeutics and block metastasis in prostate cancer patients by preventing the downstream event of association of CTR and the PDZ binding domain of ZO-1. Development of such fully human or humanized therapeutic antibodies against either CTR or CT is a widely known to anyone skilled in the art and can be employed to develop novel therapeutics. Likewise, small molecule antagonist of CTR which can lead to the abrogation of interaction between ZO-1 and CTR can be developed by combinatorial chemistry and screening techniques or through in-silico modelling, techniques widely used by people skilled in the art. In addition, antibodies to the PDZ binding domains of ZO-1 can be developed by techniques well known in the art, and such antibodies used to block the interaction between CTR and ZO-1 and thus inhibit metastasis.

Solid cancers other than prostate cancer were also found to employ the same mechanism, i.e., receptor-ZO-1 interaction leading to disruption of TJs and dissemination of cancer cells. Drugs that disrupt receptor-ZO-1 interaction through the PDZ domain would be therapeutically active against pancreatic cancer or for any solid tumors by inhibiting their metastatic potential or increasing angiogenesis in prostate or ovarian cancer cells.

BRIEF DESCRIPTION OF THE DRAWINGS

FIG. 4A depicts micrographs showing the results of acceptor photobleaching fluorescence resonance energy transfer (FRET) microscopy experiments with FRET pair CTRwt-CFP:ZO-1wt-YFP in absence of CT. Live PC-31 cells co-expressing CTR-wt-CFP (cyan fluorescent protein) and ZO-1-wt-YFP (yellow fluorescent protein) were imaged at room temperature with excitation at 436 nm. CFP and YFP emissions were monitored at 480 nm and 535 nm respectively. Micrographs under column 1 are differential interference contrast (DIC) images of cells in culture. Micrographs under columns 2 and 3 are YFP and cyan fluorescent protein CFP images pre-bleaching. Micrographs under column 4 are images of CFP post-YFP bleach, and micrographs under column 5 are the results of column 4 minus column 3.

FIG. 4B depicts micrographs showing the results of acceptor photobleaching FRET microscopy experiments with FRET pair CTRwt-CFP:ZO-1wt-YFP in presence of CT. Live PC-31 cells co-expressing CTR-wtCFP and ZO-1-wtYFP were imaged at room temperature with excitation at 436 nm. CFP and YFP emissions were monitored at 480 nm and 535 nm respectively. Micrographs under column 1 are DIC image of cells in culture. Micrographs under columns 2 and 3 are YFP and CFP images pre-bleaching. Micrographs under column 4 are images of CFP post-YFP bleach, and micrographs under column 5=column 4−column 3.

FIG. 4C depicts micrographs showing the results of acceptor photobleaching FRET microscopy experiments with FRET pair CTRΔESS (CTRΔPDZ)-CFP:ZO-1wt-YFP in absence of CT. Live PC-31 cells co-expressing CTR-wtCFP and ZO-1-wtYFP were imaged at room temperature with excitation at 436 nm. CFP and YFP emissions were monitored at 480 nm and 535 nm respectively. Micrographs under column 1 are DIC image of cells in culture. Micrographs under columns 2 and 3 are YFP and CFP images pre-bleaching. Micrographs under column 4 are images of CFP post-YFP bleach, and micrographs under column 5=column 4−column 3.

FIG. 4D depicts micrographs showing the results of acceptor photobleaching FRET microscopy experiments with FRET pair CTRΔESS (CTRΔPDZ)-CFP:ZO-1wt-YFP in presence of CT. Live PC-31 cells co-expressing CTR-wtCFP and ZO-1-wtYFP were imaged at room temperature with excitation at 436 nm. CFP and YFP emissions were monitored at 480 nm and 535 nm respectively. Micrographs under column 1 are DIC image of cells in culture. Micrographs under columns 2 and 3 are YFP and CFP images pre-bleaching. Micrographs under column 4 are images of CFP post-YFP bleach, and micrographs under column 5=column 4−column 3.

FIG. 4E depicts micrographs showing the results of acceptor photobleaching FRET microscopy experiments with FRET pair CTRwt-CFP:ZO-1ΔPDZ3-YFP in absence of CT. Live PC-31 cells co-expressing CTR-wtCFP and ZO-1-wtYFP were imaged at room temperature with excitation at 436 nm. CFP and YFP emissions were monitored at 480 nm and 535 nm respectively. Micrographs under column 1 are DIC image of cells in culture. Micrographs under columns 2 and 3 are YFP and CFP images pre-bleaching. Micrographs under column 4 are images of CFP post-YFP bleach, and micrographs under column 5=column 4−column 3.

FIG. 4F depicts micrographs showing the results of acceptor photobleaching FRET microscopy experiments with FRET pair CTRwt-CFP:ZO-1ΔPDZ3-YFP in presence of CT. Live PC-31 cells co-expressing CTR-wtCFP and ZO-1-wtYFP were imaged at room temperature with excitation at 436 nm. CFP and YFP emissions were monitored at 480 nm and 535 nm respectively. Micrographs under column 1 are DIC image of cells in culture. Micrographs under columns 2 and 3 are YFP and CFP images pre-bleaching. Micrographs under column 4 are images of CFP post-YFP bleach, and micrographs under column 5=column 4−column 3.

FIG. 7A shows representative micrographs of CTR-ZO-1 interactions in PC-3 CTRwt cells in the absence and presence of CT stimulation for 30 sec. Each dot represents an interaction between activated CTR and ZO-1, detected by in situ PLA™ using the Duolink® kit. Nuclei were stained with DAPI. The graph presents quantitative data of CTR-ZO-1 interactions in three separate but identical experiments (mean±SEM; n=6, p<0.001, paired t-test).

FIG. 7B shows representative micrographs of CTR-ZO-1 interactions in PC-3CTRΔESS cells treated as described in FIG. 7A. The graph presents quantitative data of three separate but independent experiments described in FIG. 7A (mean±SEM for n=6).

FIG. 7C shows representative micrographs of CTR-ZO-1 interactions in LNCaP cells as described in FIG. 7A. The graph presents quantitative data of three separate but independent experiments as described in FIG. 7A (mean±SEM; n=6, *p<0.001, paired t-test).

FIG. 15A shows the effect of CT on TJ stability as measured with transelectric epithelial resistance and paracellular permeability of PC3-CTRwt cells treated with/without CT. The left graph shows transelectric epithelial resistance (TER) of PC3-CTRwt cells, with and without CT, over five hours. Polarized PC-3-CTRwt cells were serum-starved for 4 hours, then treated with/without 50 nM CT. TER was measured with EVOM volt-ohm meter. The results are expressed as TER ±SEM ($\Omega cm^2 \pm SEM$; n=6). The right graph shows paracellular permeability (PCP) of PC3-CTRwt cells with and without CT. PCP was determined by diffusion of ~4 kDa TRITC-conjugated dextran from the upper to the lower chamber in one hour. The results are expressed as μg/ml/hour of TRITC-Dextran diffused ±SEM (n=6; *p<0.05 (−CT v +CT, One way ANOVA and Newman-Keul's test)).

for various time periods in the presence/absence of mPKI (10 nM). β-actin was used for control.

Figures 16A, 16B, 16C:
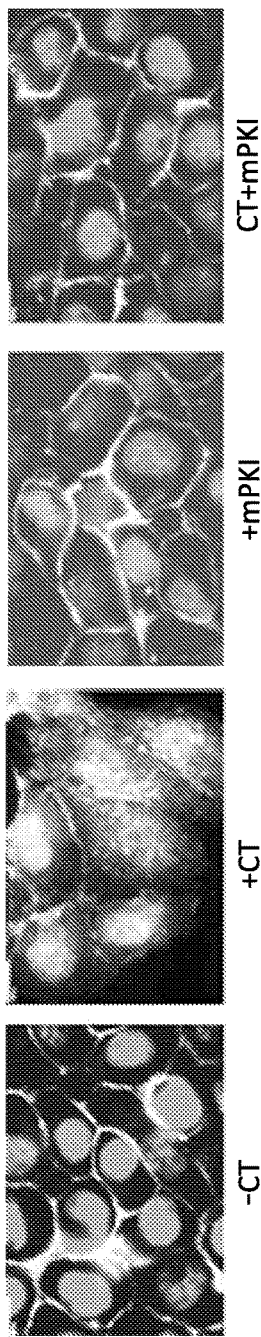
FIG. 16A depicts photo micrographs of PC3-CTRwt cells, CT-stimulated in the presence and absence of mPKI. Polarized PC-3CTRwt cells were fixed and stained for FLAG (CTR), claudin 3 and ZO-1 before and after 30 min of CT stimulus in the presence/absence of mPKI (10 nM) (magnification 400×).
FIG. 16B shows representative immunoblots of claudin 3, ZO-1 and occludin of insoluble and soluble fractions in TX-100 of cells that were treated with/without CT (50 nM)

FIG. 16C shows representative immunoblots of claudin 3, ZO-1 and occludin of insoluble and soluble fractions in TX-100 of cells that were treated with/without CT (50 nM) for various time periods in the presence/absence of H89 (10 μM). β-actin was used for control.

Figure 17A:
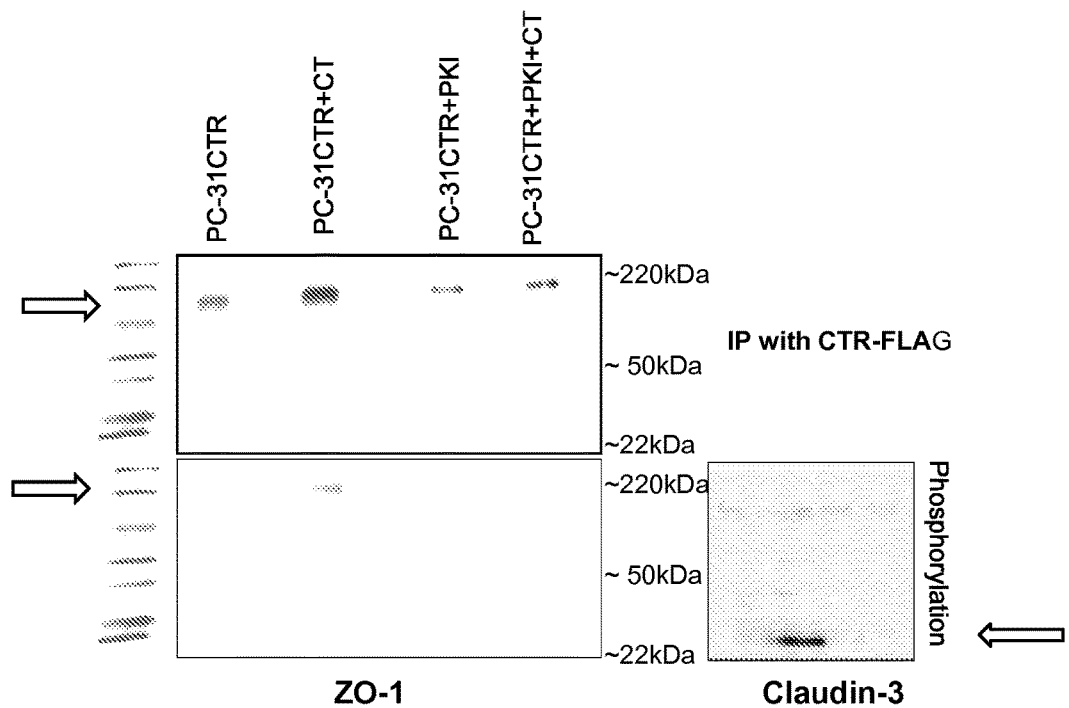

FIG. 17A shows autoradiograms of $^{32}$P-labeled cell lysates and immunoblots of ZO-1 and claudin 3 from PC-31CTR treated with/without CT in the presence/absence of mPKI. Arrows indicate location of ZO-1 and claudin-3.

Figure 17B:
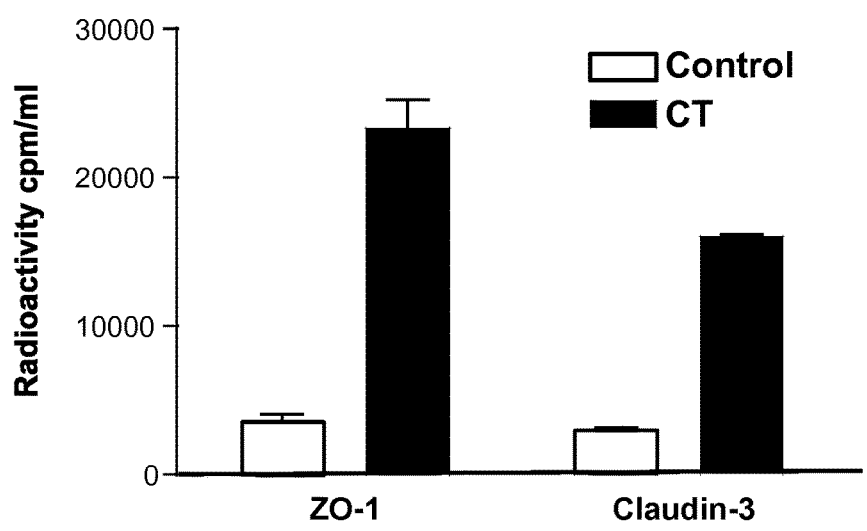

FIG. 17B depicts the total amount of $^{32}$P-radioactivity of IP bands of ZO-1 and claudin from cells treated with CT (CT) and without treatment (Control, C).

Figure 17C:
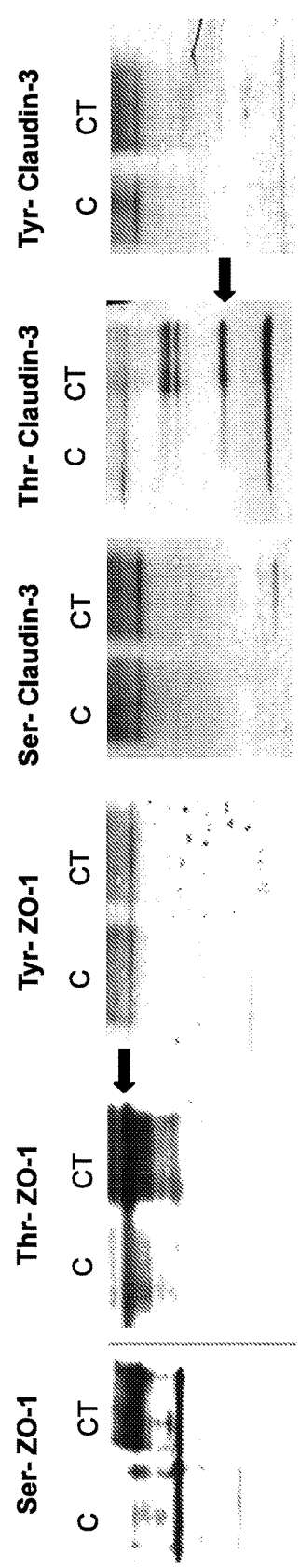

FIG. 17C shows representative immunoblots of ZO-1 and claudin 3 cell lysates treated with (CT) and without CT (C). The blots were probed by antibodies to phosphoserine (Ser), phosphothreonine (Thr), and phosphotyrosine (Tyr). The arrow indicates the band corresponding to either Z0-1 (221 KDa) or claudin-3 (23 KDa).

Figure 18A:
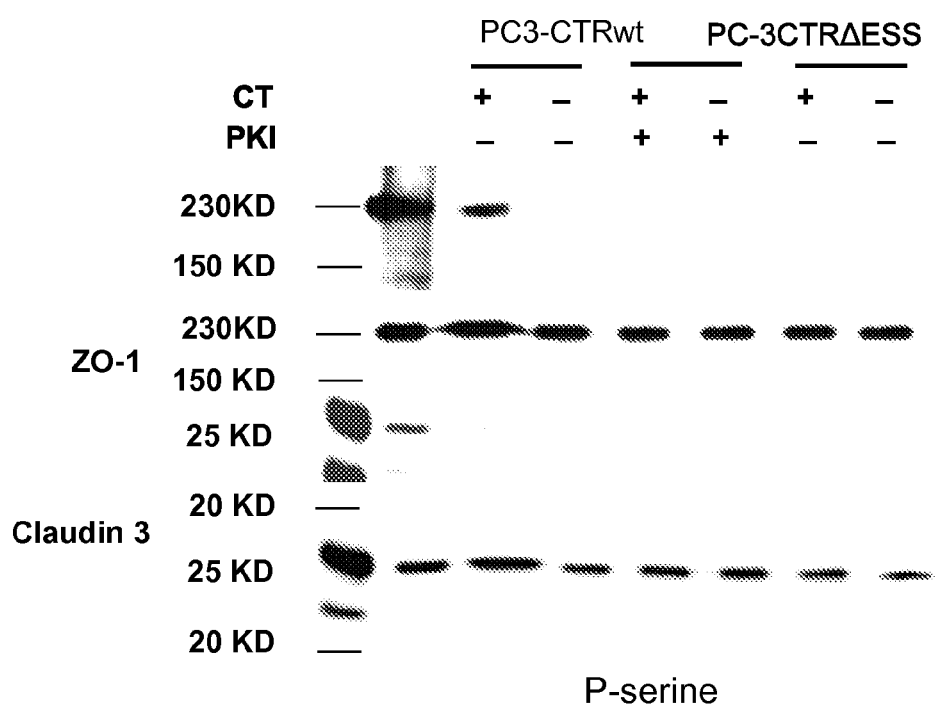

FIG. 18A shows serine phosphorylation of ZO-1 and claudin 3 in CT±mPKI-treated cell lysates from PC-3 CTRwt and PC-3 CTRΔESS cells that were immunoprecipitated with antibodies to either ZO-1 or claudin 3. The immunoprecipitates were then probed with antibodies to phosphoserine.

Figure 18B:
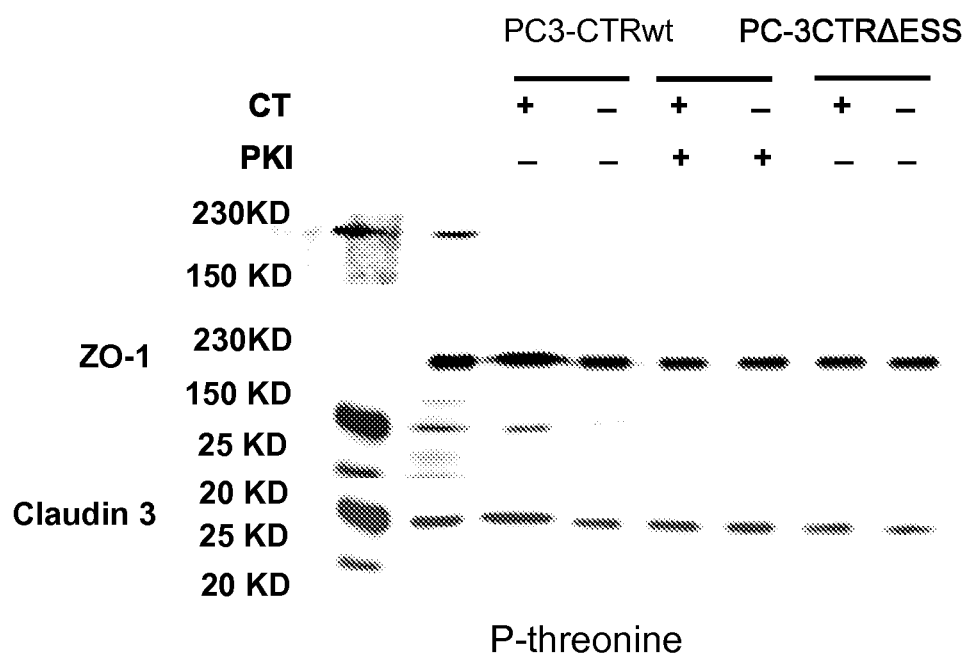

FIG. 18B shows threonine phosphorylation of ZO-1 and claudin 3 in CT±mPKI-treated cell lysates from PC-3 CTRwt and PC-3 CTRΔESS cells that were immunoprecipitated with antibodies to either ZO-1 or claudin 3. The immunoprecipitates were then probed with antibodies to phosphothreonine.

FIG. 19A shows photomicrograhs of PC-3 CTRΔESS cells with and without CT stimulus. Polarized PC-3 CTRΔESS cells were fixed and stained for FLAG (CTR), claudin 3 and ZO-1 before and after 30 min of CT stimulus (magnification 400×).

FIG. 19B shows a representative immunoblot of claudin 3, ZO-1 and occludin from insoluble and soluble fractions in TX-100 of PC-3 CTRΔESS cells that were treated with CT (50 nM) for various time periods from 0 to 240 min.

FIG. 19C shows a representative immunoblot of claudin 3, ZO-1 and occludin of insoluble and soluble fractions in TX-100 of CTR-ΔPDZ1, CTRΔPDZ2 and CTRΔPDZ3 cells that were treated with and without CT (50 nM).

Figure 20A:
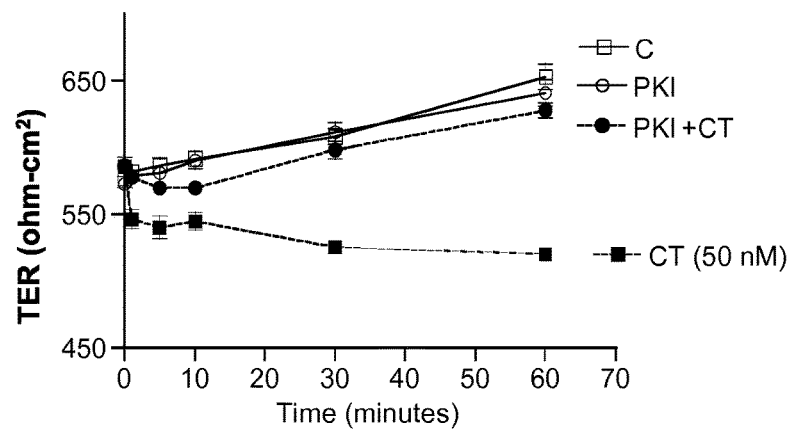

FIG. 20A shows the disruption of TJs as measured by transelectric epithelial resistant (TER) of polarized PC-31-CTR cells measured at several time points after stimulation with diluent, CT (50 nM), myristoylated PKA inhibitory peptide (mPKI) (100 nM) or CT+mPKI.

Figure 20B:
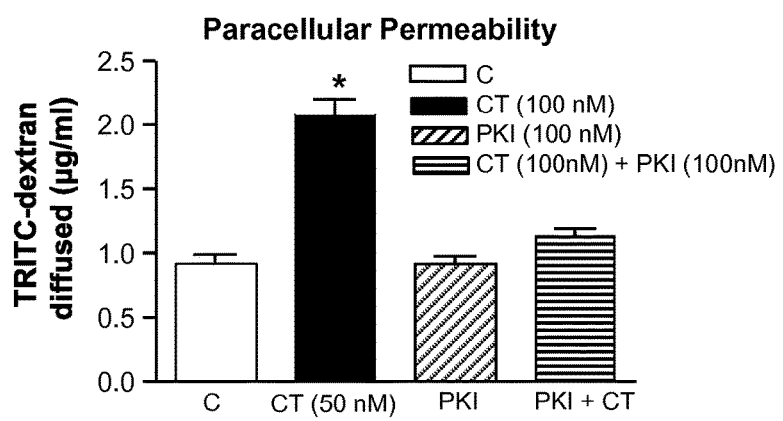

FIG. 20B shows the disruption of TJs as measured by paracellular permeability (PCP) of PC-31-CTR-wt cells cultured in transwell chambers (0.4 μm pore size, 24 mm diameter; Costar) for three days to polarize, and treated with CT (50 nM), mPKI (100 nM) or CT+M-PKI. Paracellular permeability of the cells was determined by diffusion of TRITC-conjugated dextran from the upper chamber to the lower chamber.

Figure 20C:
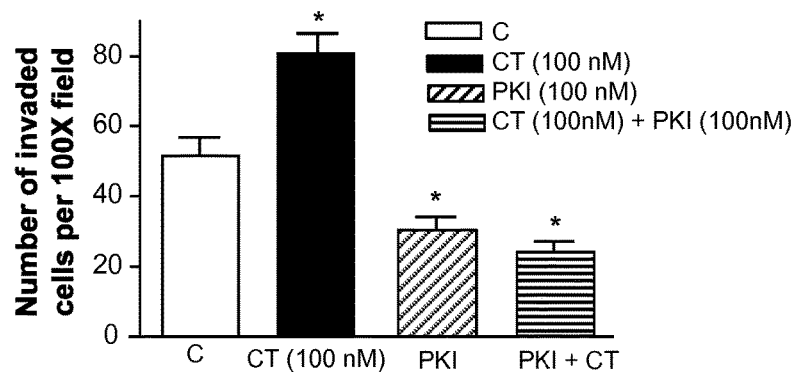

FIG. 20C shows PC-3M invasion of PC-31-CTR cells 24 hours after being treated with diluent (C), CT, PKI, and CT+PKI. Confluent cultures of PC-31-CTR cells were tested for PC-3M cells invasion in Matrigel™ invasion chambers after treatment with diluent (C), CT (50 nM), mPKI (myristoylated PKA inhibitory peptide-100 nM) or M-PKI+CT. The number of invaded cells was determined after 24 hours.

Figure 20D:
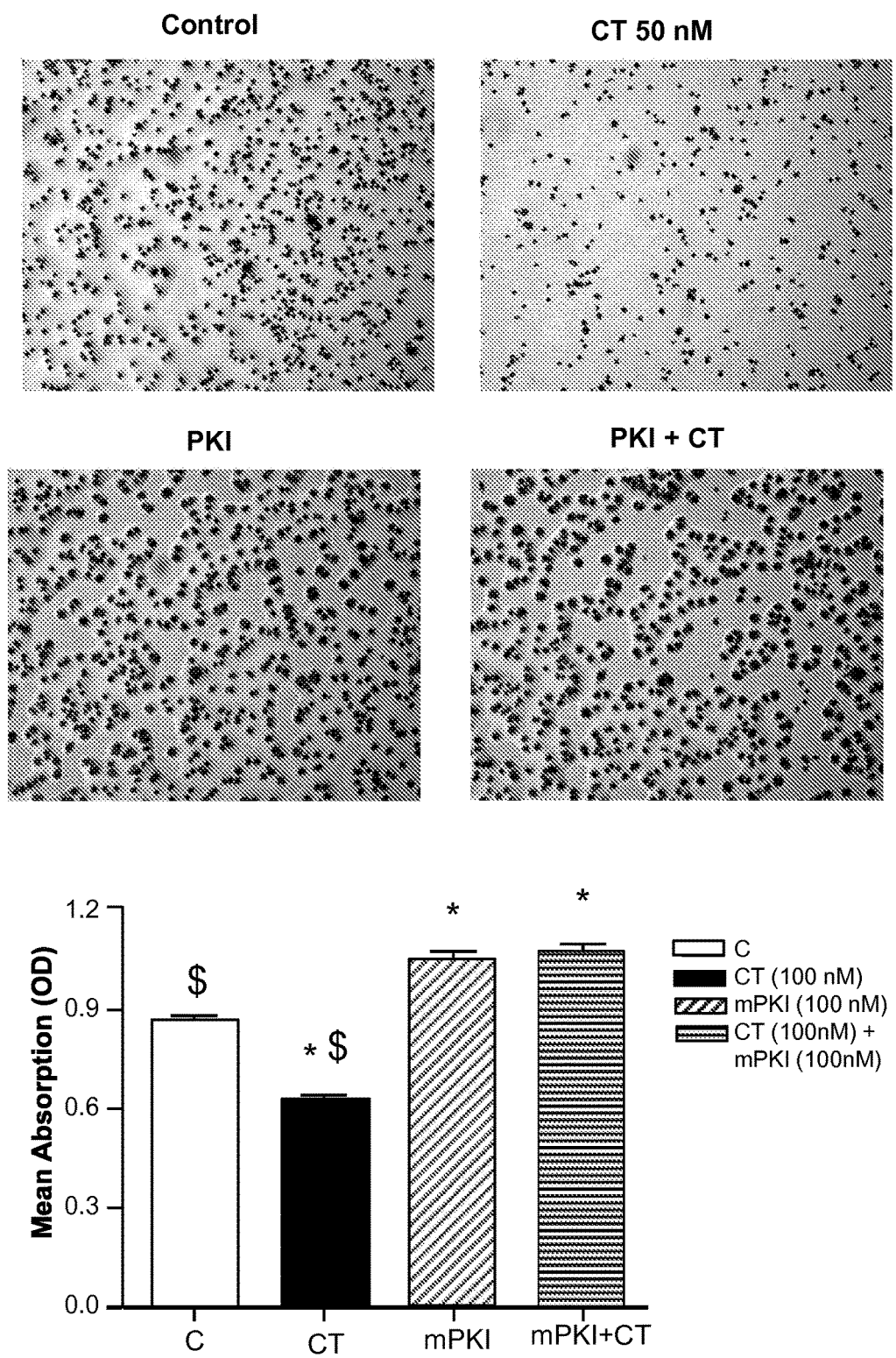

FIG. 20D shows photomicrographs depicting cell adhesion on culture dishes of PC-31-CTR cells one hour after being treated with diluent (C), CT, PKI, and CT+PKI. Confluent cultures of PC-31-CTR cells were tested for cell adhesion after treatment with diluent (C), CT (50 nM), mPKI (myristoylated PKA inhibitory peptide (100 nM) or mPKI+CT. The number of adherent cells was determined by absorbance after 1 hour and are shown in the right graph.

Figure 21:
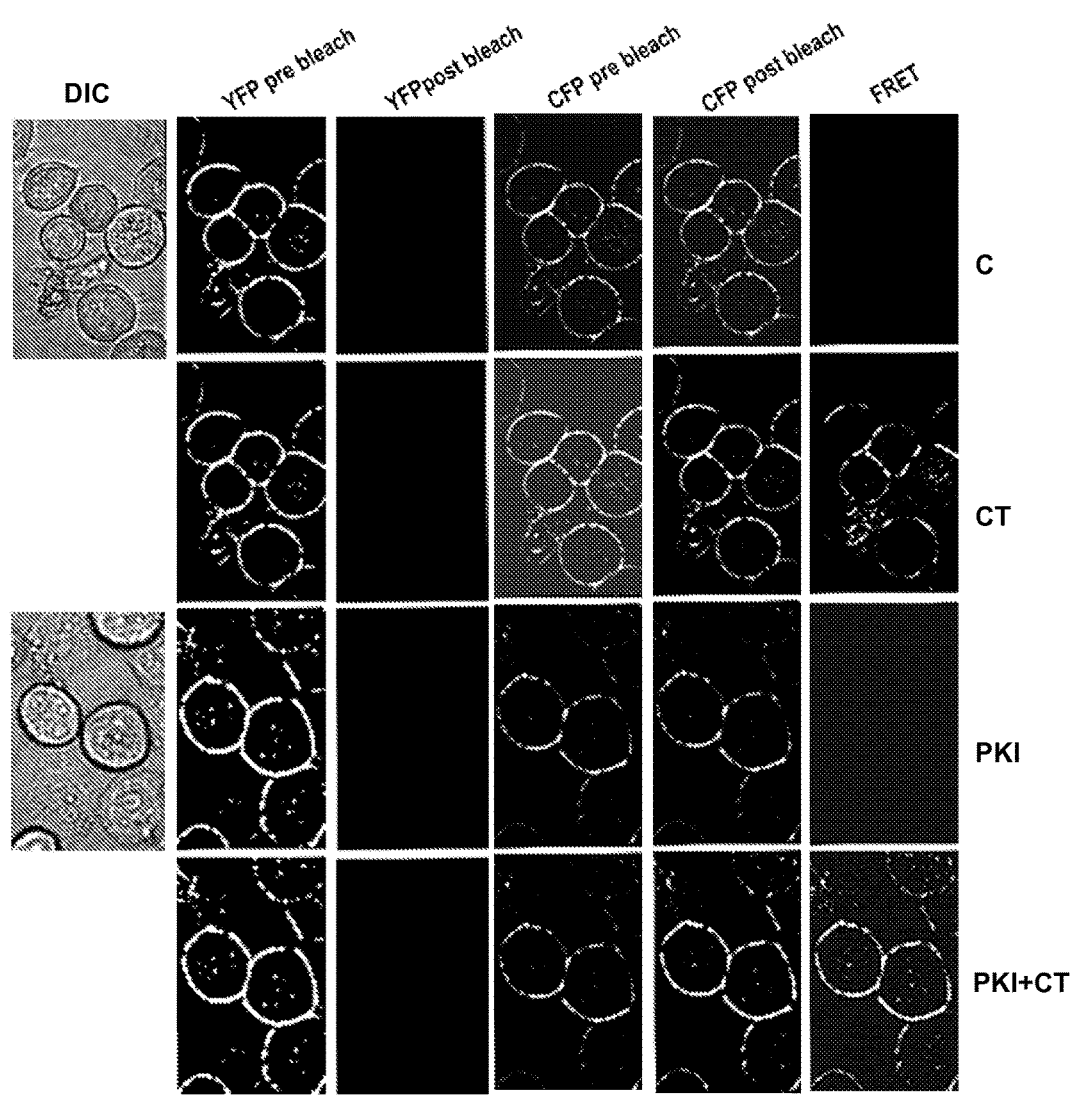

FIG. 21 shows CTR-ZO-1 FRET in the presence and absence of mPKI. Live PC-31 cells co-expressing CTR-wtCFP and ZO-1-wtYFP were imaged at room temperature with excitation at 436 nm. CFP and YFP emissions were monitored at 480 nm and 535 nm respectively. Micrographs under column 1 are DIC images of cells in culture. Micrographs under column 2 are YFP images pre-bleaching. Micrographs under column 3 are images of YFP post-CFP bleaching. Micrographs under column 4 are CFP images pre-bleaching. Micrographs under column 5 are images of CFP post-YFP bleach. Micrographs under column 6 are column 5 minus column 4. The cells were treated with the diluent (C), CT (50 nM), mPKI (100 nM) and CT+mPKI.

Figure 22A:
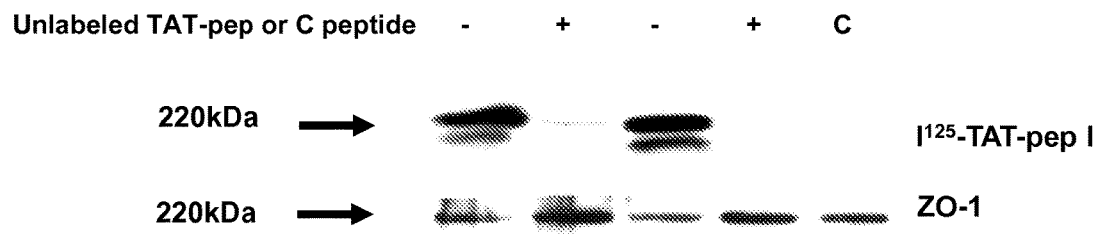

FIG. 22A shows antagonism of CTR-ZO-1 interaction with TAT-pepI. $^{125}$I labeled TAT-pepI were first incubated with/without 20 μM of either TAT-pepI, or TAT-C (20 μM) for 5 min. The cells were then treated with $^{125}$I-TAT-pepI or TAT-C for 25 min. The cell lysates were then immunoprecipitated with Anti-ZO-1 serum, the immunoprecipitates were washed, fractionated on SDS-gel, and then immunoblotted for ZO-1 and autoradiographed.

Figure 22B:
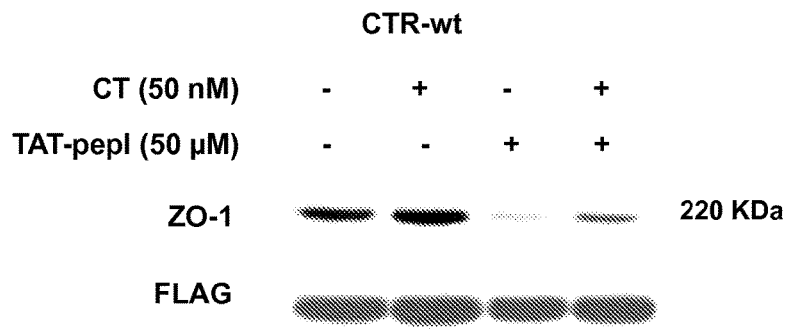

FIG. 22B depicts an immunoblot of TAT-pepI as antagonist for CTR-ZO-1 interaction. FLAG-PC-3CTRwt cells were incubated with excess of TAT-pepI with and without CT for 3 min. The cell lysates were then used to immunoprecitate CTR-FLAG, and the immunoprecipitates were immunoblotted. The blots were then probed for ZO-1 and normalized with IP antibodies (Anti-FLAG).

Figure 22C:
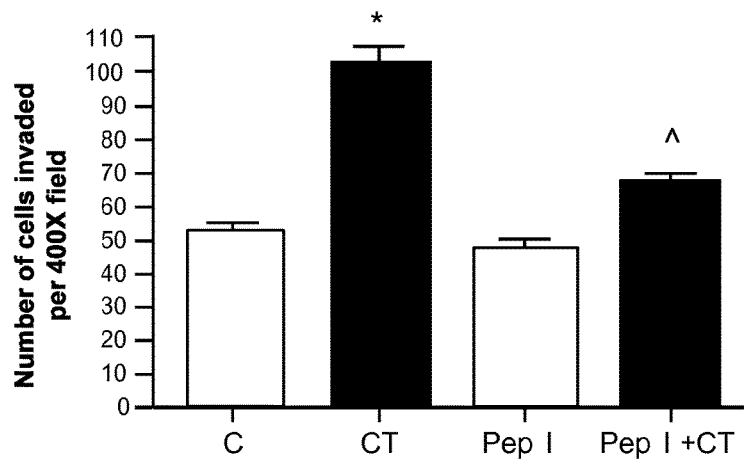

FIG. 22C shows cell invasion of untreated and CT-treated (50 nM) PC-3CTRwt cells in the presence/absence of TAT-pepI. TAT-pepI attenuates CT-stimulated invasion of PC-3CTRwt cells.

Figure 23:
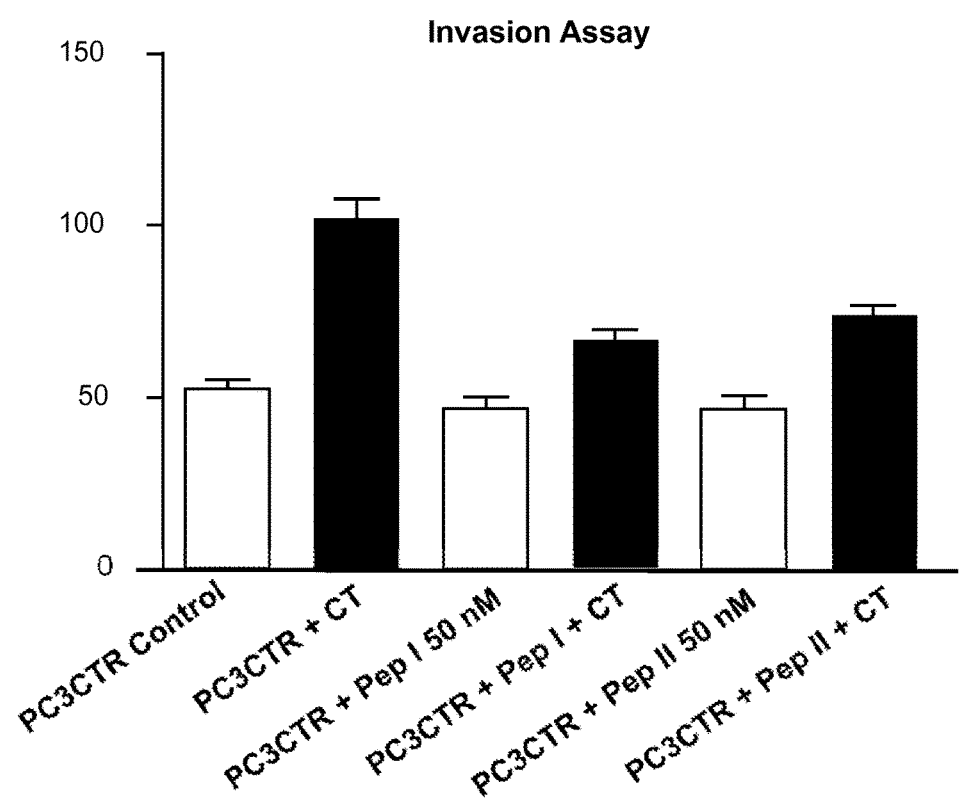

FIG. 23 shows cell invasion of untreated and CT-treated (50 nM) PC-3CTRwt cells in the presence/absence of TAT-pepI or TAT-pepII. Both TAT-pepI and pepII attenuate CT-stimulated invasion of PC-3CTRwt cells.

Figure 24C:
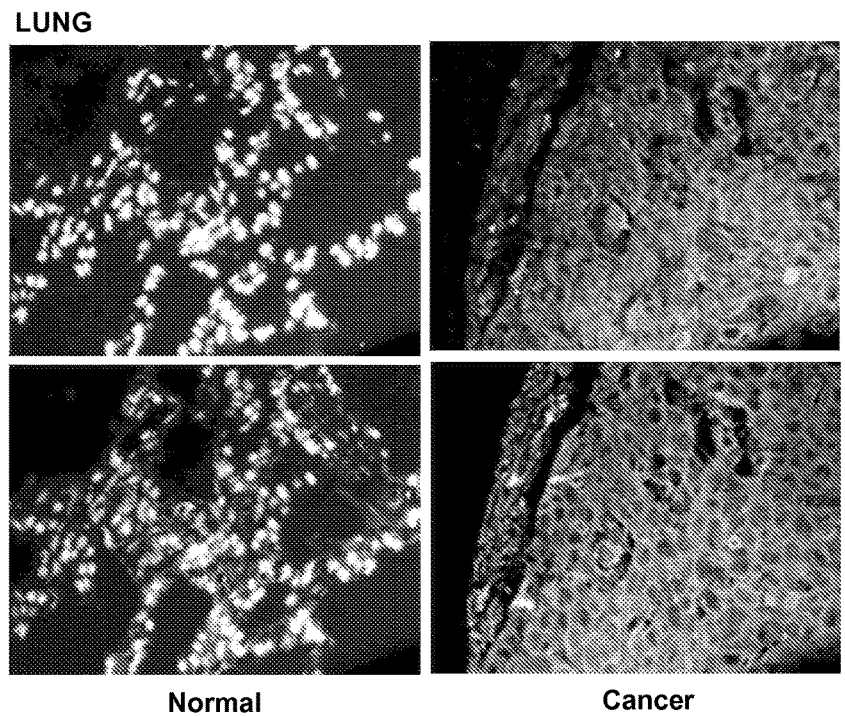
Figure 24D:
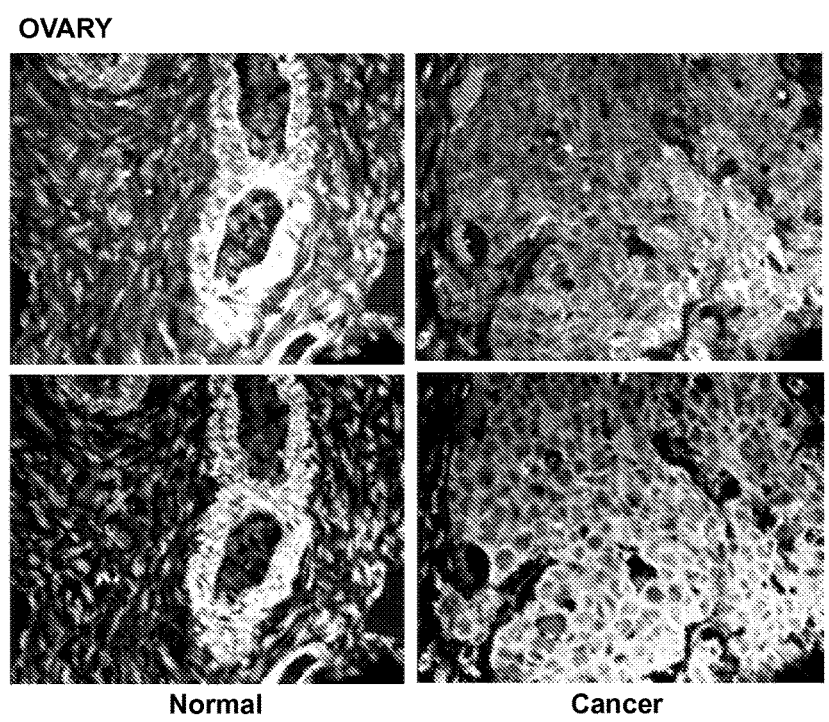
Figure 24E:
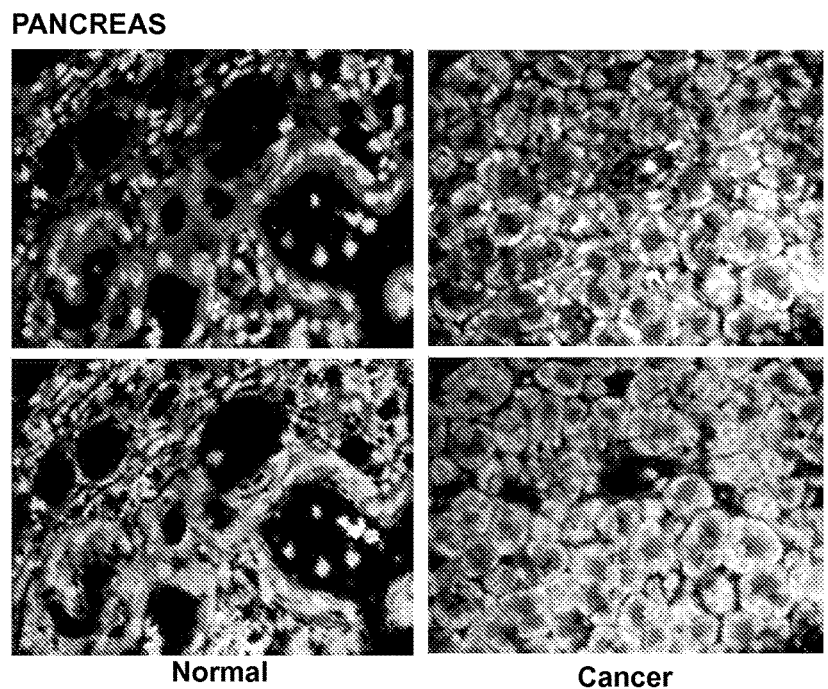
Figure 24F:
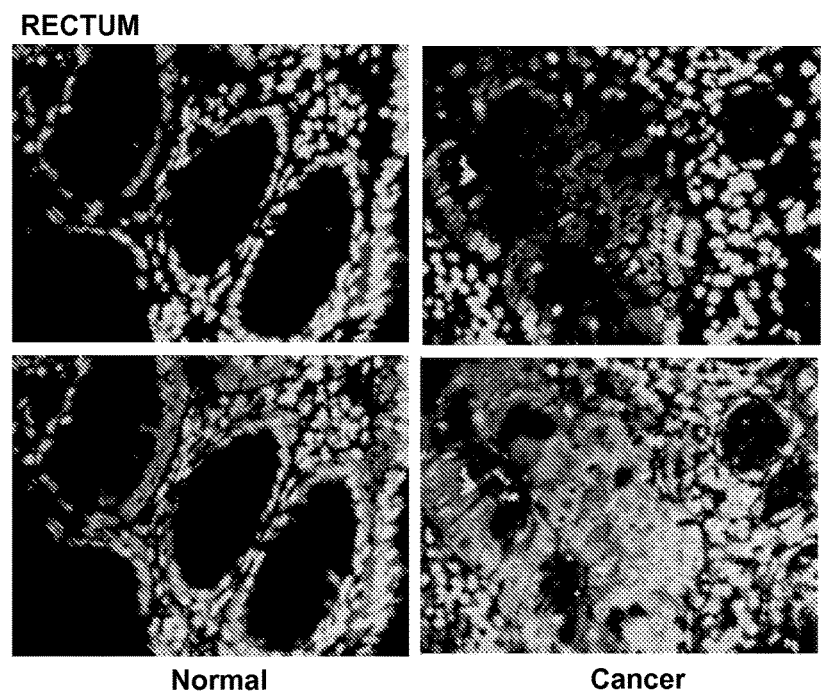

FIGS. 24A-24F depict photomicrographs of normal and cancerous cells as stained for CTR or CT from various tissues—bladder (FIG. 24A), esophagus (FIG. 24B), lung (FIG. 24C), ovary (FIG. 24D), pancreas (FIG. 24E), and rectum (FIG. 24F).

Figure 25A:
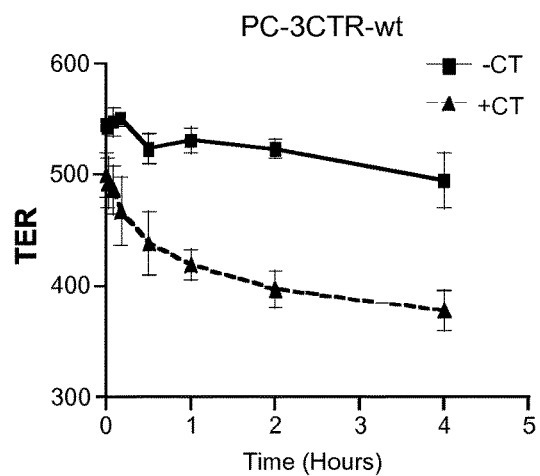
Figure 25B:
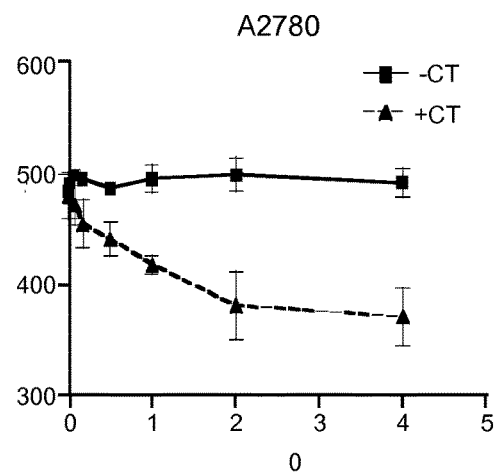
Figure 25C:
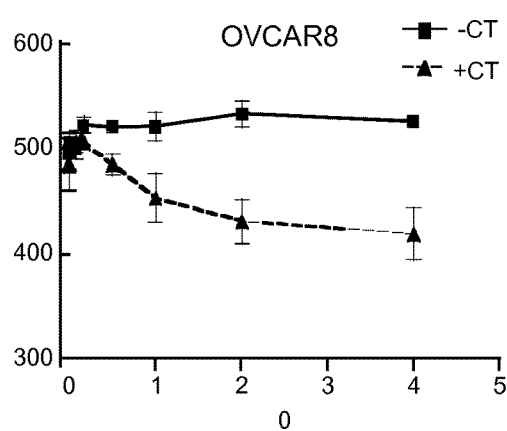
Figure 25D:
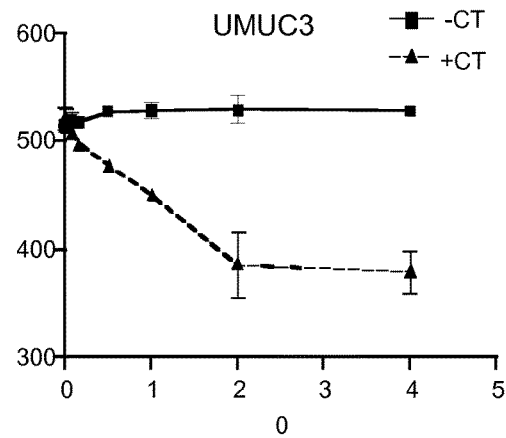
Figure 25E:
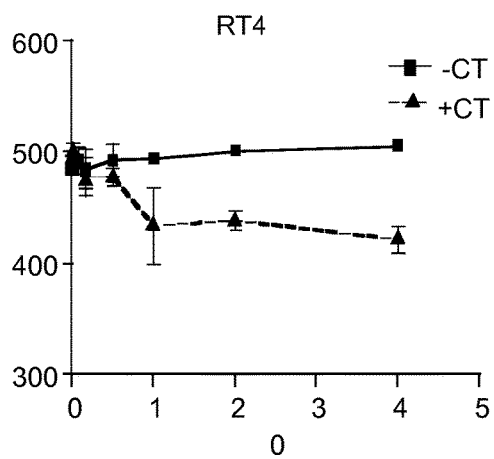
Figure 25F:
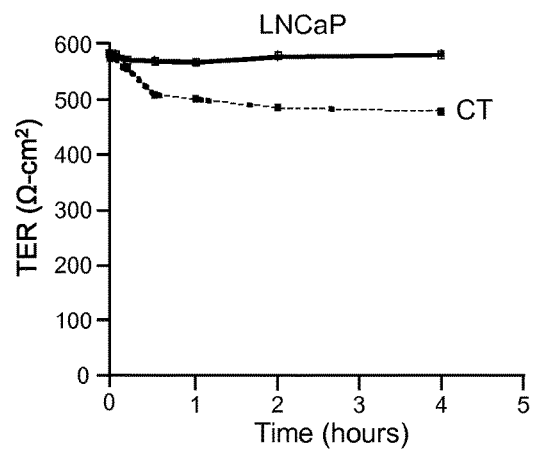
Figure 25G:
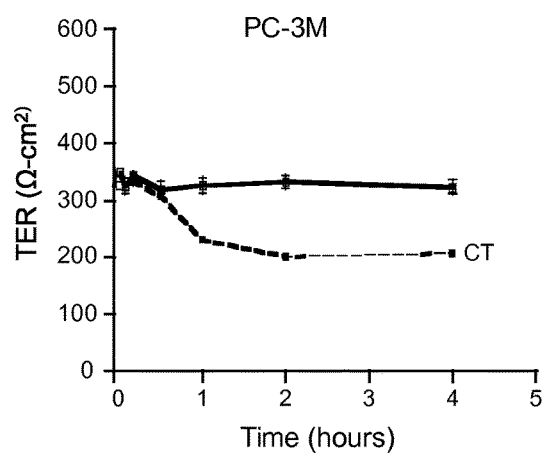
Figure 25H:
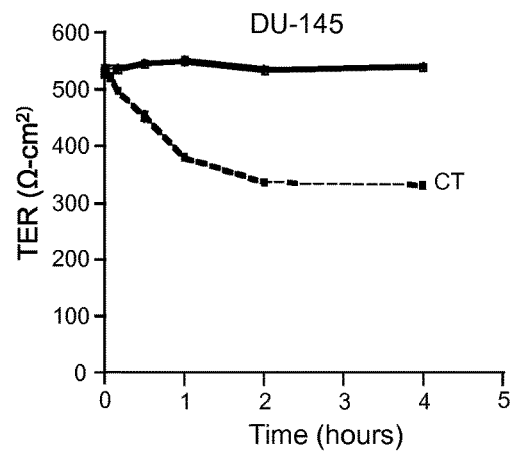

FIG. 25A-H depict TER analysis over 6 hours in the following cell lines treated with and without CT: PC-3TRwt (FIG. 25A), A2780 (FIG. 25B), OVCAR8 (FIG. 25C), UMUC3 (FIG. 25D), RT4 (FIG. 25E), LNCaP (FIG. 25F), PC-3M (FIG. 25G), and DU-145 (FIG. 25H).

Figure 26A:
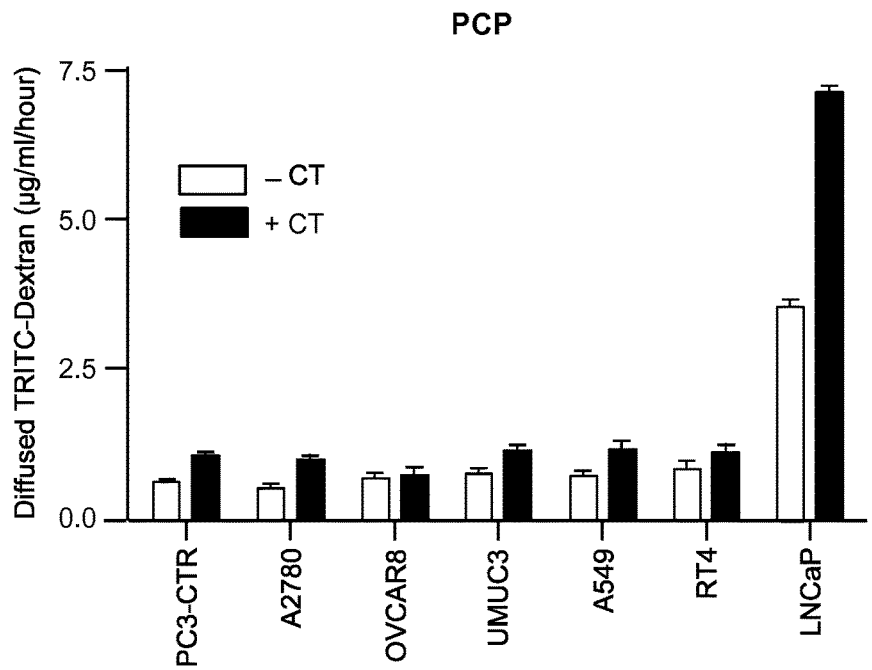

FIG. 26A depicts PCP in the following cell lines treated with and without CT: PC-3TRwt, A2780, OVCAR8, UMUC3, A549, RT4, and LNCaP.

Figure 26B:
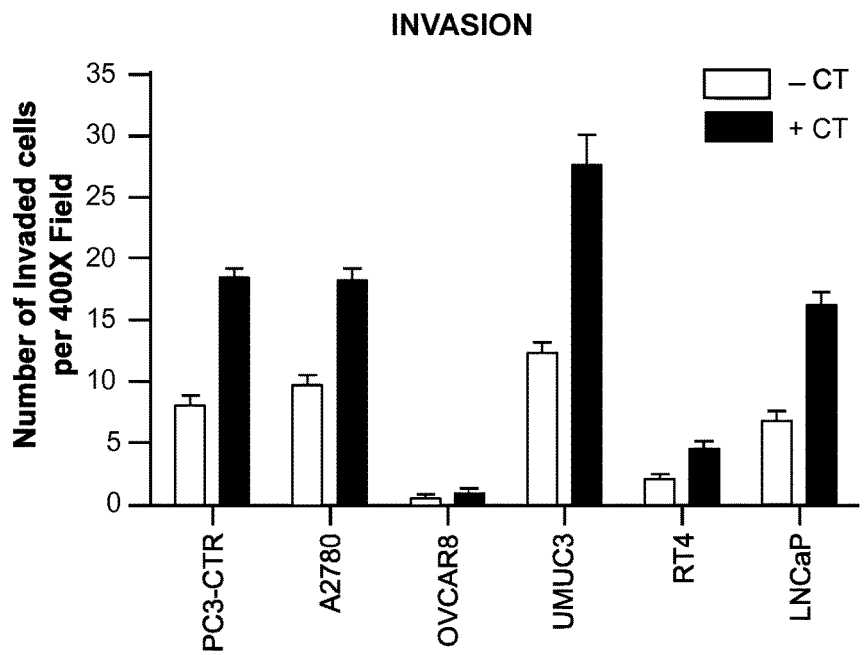

FIG. 26B depicts cell invasion in the following cell lines treated with and without CT: PC-3TRwt, A2780, OVCAR8, UMUC3, RT4, and A549.

Figure 27:
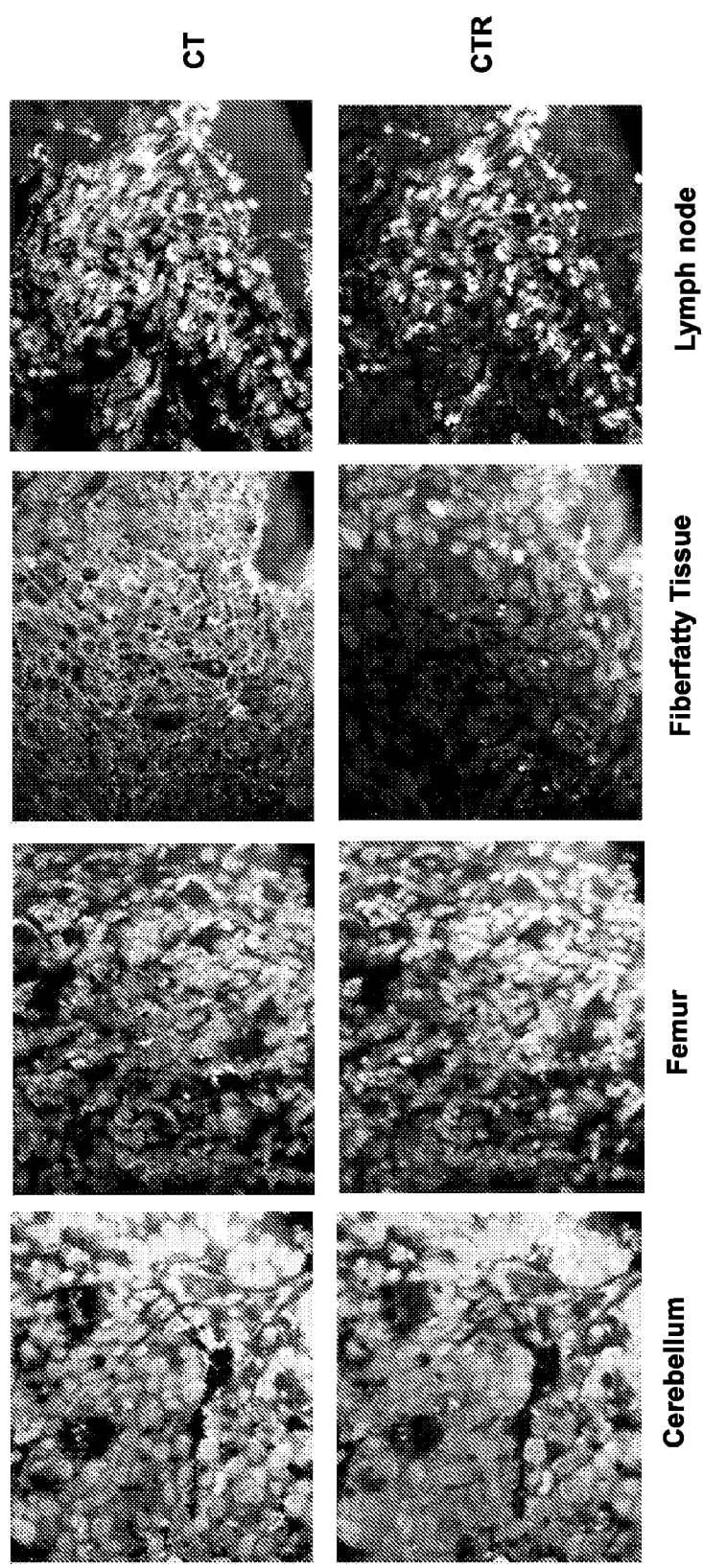

FIG. 27 depicts photomicrographs of CT and CTR in metastatic cells from the following tissues: (A) from cerebellum from adenocarcinoma in the lung; (B) from the right femur from adenocarcinoma in the lung; (C) from fiber fatty tissue from squamous cell carcinoma in the larynx; and (D) from lymph node from adenocarcinoma in the lung.

Figure 28:
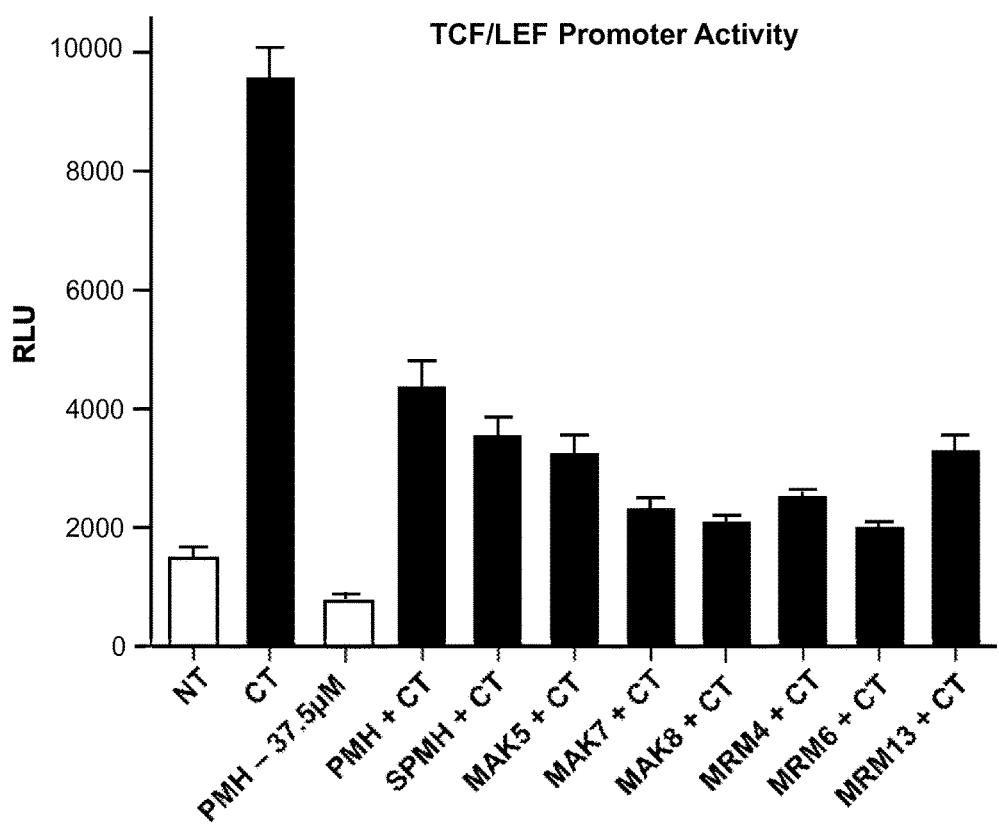

FIG. 28 depicts effect of CT on TCF/LEF promoter activity in PC-3 cells with various compounds added with CT. Cells were seeded into 6-well plates and transfected with the pGL3-OT luciferase/pRL-tK plasmids or pGL3-OF-luciferase/pRL-TK plasmids. The cells were then incubated in complete medium for 48 h, after which they were serum-starved for 16 h. The cells were then treated with CT and/or PMH compounds, and the cell lysates analyzed for luciferase activity. The results are expressed as relative light units (RLU) after normalization with *Renilla* luciferase activity. The experiment was repeated three separate times, and results expressed as means±S.E.M.

FIG. 29 shows the amino acid for the ZO-1 PDZ domains of PDZ1 domain (SEQ ID NO:9), PDZ2 domain (SEQ ID NO:10), and PDZ3 domain (SEQ ID NO:11).

MODES OF USING THE INVENTION

Example 1

Experimental Procedures

Animals:

Male balb/c nu/nu mice (6-8 weeks old) were purchased from Harlan (Madison, Wis.), and housed two per cage in microisolator units under controlled humidity and temperature, fed ad lib on a standard sterilizable laboratory diet, and quarantined for one week prior to their use in the study.

Surgical Orthotopic Implantation (SOI):

All animal procedures were conducted in accordance with the principles and procedures outlined by the NIH and Institutional Animal Care and Use Committee at University of Louisiana at Monroe. The SOI was performed under Ketamin/Xylazine anesthesia as previously described (Chien et al., 1999a; Shah et al., 2009b; Shah et al., 2008). Tumor cell suspensions ($1 \times 10^6$ cells/20 µl) were injected into the dorsal prostate using a 30-gauge needle (n=6/cell line). Animals were regularly monitored for tumor growth and metastasis by fluorography using Kodak 4000 MM imaging station, and sacrificed within sixty days after orthotopic tumor cell implantation. Several organs were collected, fixed and examined for tumor metastasis. At necropsy, primary tumor and other organs were harvested and weighed. Wet sections of organs were examined for the presence of RFP. The remaining tissues were fixed in neutral buffered formalin and processed for H&E staining.

Cell Culture:

LNCaP, PC-3 and DU-145 cell lines were obtained from American Tissue Culture Collection (Manassas, Va.), and maintained as recommended by the supplier for less than six months after the receipt. PC-3I subline was an isolated PC-3 orthologue that lacked CT and CTR mRNA. PC-3M cell line was provided by Dr. Isiah Fidler (MD Anderson Cancer Center, Houston, Tex.). Some of these prostate cancer cell lines were chosen because of the differences in malignancy and in expressing calcitonin (CT) and calcitonin receptor (CTR). For example, PC-3M cells express both CT and CTR and are poorly differentiated, highly metastatic and tumorgenic, and are androgen-independent. PC-3 cells express CT but not CTR, and are moderately differentiated, moderately metastatic and tumorigenic, and androgen-resistant. LNCaP cells express CTR, but not CT; and are well differentiated, poorly metastatic and tumorgenic, and androgen-sensitive. All cell lines were cultured in complete medium (RPMI 1640 medium supplemented with 10% fetal calf serum, 100 IU/ml penicillin G and 100 µg/ml streptomycin) under previously described culture conditions.

DNA Constructs: FLAGCTRwt and FLAGCTRΔESS:

CTR C-PDZ binding motif (ESSA; SEQ ID NO:1) was replaced with alanines (AAAA; SEQ ID NO:4) by inserting mismatches in respective codons as underlined. The primer sequences are as follows:

```
Forward Primer:
                                          (SEQ ID NO: 5)
5'-aagcttatggactacaaggacgacgatgacaagagcttcacattta caagccggtgcttg-3'

Reverse Primers:
CTRwt:
                                          (SEQ ID NO: 6)
5'-ctcgagtcaagcagatgactcttgctctatgatattcaaagggat gatctc-3'

CTRΔESS:
                                          (SEQ ID NO: 7)
5'-ctcgagtcaagcagcagcagcttgctctatgatattcaaagggat gatctc-3'
```

The full-length FLAG-CTRwt and FLAG-CTRΔESS were inserted in pcDNA3.1 expression vector by directional cloning (Invitrogen) (Sanger et al., 1992). Each PCR reaction used a common 5' primer (100 pmol) encoding an HindIII site surrounding the start codon, and unique 3' primers with XhoI site following the stop codon to provide cloning sites for the coding regions of CTRwt/ΔESS variants. The templates were amplified for 30 rounds of PCR (0.5-min denaturation 94° C., 1-min anneal 57° C., 1-min extension 72° C.) using pfu Taq polymerase. PCR products were verified by sequencing (Sanger et al., 1992). The cDNAs for CTRwt/ΔESS were cloned in the pcDNA3.1 vector to obtain expression plasmids (Invitrogen).

ZO-ΔPDZ Mutants:

The cDNA sequence of ZO-1 was mutated by deleting each/or all of the three PDZ domains to obtain the following four mutants: ΔPDZ1 (aa 2-156), ΔPDZ2 (aa 159-252), ΔPDZ3 (aa 294-633) and ΔPDZall (aa 67-1033) (Fanning et al., 1998). All ZO-1 constructs were Myc tagged at the C-terminal and cloned in pCB6 eukaryotic expression vector (Fanning et al., 1998). The cDNA constructs were transfected in PC-3 cells using FuGene 6™, selected in G418, multiple clones were examined, and those expressing stable transgene expression were selected for subsequent studies (Shah et al., 2009; Thomas et al., 2006).

Ligand Binding and Effector Activation: Membrane Preparation and Ligand Binding:

Cultured PC-3CTR-wt and PC-3CTRΔESS cells were harvested to prepare membranes as described before (Shah et al., 1994). The membranes were incubated with increasing concentrations of monoiodinated $^{125}$I-sCT to determine CTR binding characteristics (Shah et al., 1994). The binding data was analyzed by non-linear regression and Scatchard analysis using Prism4™ program (Graphpad, San Diego, Calif.).

cAMP Accumulation:

PC-3CTRwt and PC-3CTRΔESS cells were treated with/without 50 nM CT for three min, washed and harvested in lysis buffer (50 mM Tris, pH 7.5, containing 5 mM EDTA, 50 mM NaF, 1 mM sodium pyrophosphate, 0.5 mM EGTA, 10 mM β-mercaptoethanol, leupeptin, 1 µg/ml; and aprotinin, 1 µg/ml). The lysates were analyzed for cAMP levels by radioimmunoassay (Perkin Elmer, Shelton, Conn.).

PKA, PKC Activity:

The lysates of untreated and CT-treated PC-3CTRwt and PC-3CTRΔESS cells were also used to determine CT-stimulated protein kinase A (PKA) and protein kinase C (PKC) activity (PKA and PKC assay kits, Promega, Madison, Wis.). The manufacturer's instructions were followed.

CTR-C GST Pull-Down Assay:

cDNA encoding intracellular domain of CTRwt and CTRΔESS (aa 441-476) was cloned in pGEX vector (GE Healthcare, Piscataway, N.J.) C-cDNA construct (random cDNA sequence of equivalent length) was prepared as control construct. The constructs were expressed in BL-21 *Escherichia coli* strain, and the equivalent amount of each fusion protein (approx 2 μg) was absorbed on glutathione-Sepharose 4B (GE Healthcare). The beads containing GST-Fusion proteins of C peptide, CTR-Cwt and CTR-CΔESS were then incubated with PC-31 cell lysate. The bound proteins were eluted with reduced glutathione. The presence of ZO-1 in the eluate was detected by Western blotting.

Yeast Two-Hybrid Screening:

The cDNA sequence corresponding to C-terminal domain of hCTR2 (residues 411-476) was inserted in frame in the pNLex-NLS yeast expression vector (Golemis et al., 2001). This bait plasmid was used to transform the yeast strain RFY231: MAT±ura3-1 his3 trp1î::hisG3LexAop-LEU2:: leu2. The transformed yeast was then mated to yeast (RFY309: MATa his3î200 leu2-3 lys2î201 ura3-52 trp1îhisG: pSH18-34) pre-transformed with a human prostate cDNA library in pJG4-5 vector (Origene). All rescued colonies were picked and their galactose dependence, leu and lacZ phenotypes were tested (Golemis et al., 2001; Kolonin et al., 2000). Open reading frames (ORFs) of all galactose-dependent clones were isolated by PCR and cloned into the transcription activation domain (AD) vector by gap repair. The AD clones were then mated against the bait to reconfirm that Leu and lacZ phenotypes were dependent on the ORF. Positive AD clones were further tested for specificity by mating with 7 bait strains expressing unrelated baits (*Campylobacter* proteins) (Kolonin et al., 2000).

To check the strength of interaction, original bait strain was mated with strains expressing each isolated AD clone, and reporter activation was scored on 0-3 scale for growth on leu plates (0=no growth; 3=maximal growth); and 0-5 scale for lacZ activity on X-Gal plates (0=white; 5=dark blue). All interactors in this screen scored maximal growth on leu; and the absence of lacZ activity indicated a weak, but reproducible interaction.

Overlay Assays:

Overlay assays were performed as previously described (Hall, 2004). Cell lysates from stable PC-3 transfectants expressing either ZO-1wt-MYC or ZO-1ΔPDZ-MYC mutants were prepared, fractionated on an SDS-PAGE gel and transferred to nitrocellulose membranes. The membranes were blocked in far Western buffer and incubated with purified GST tagged CTRwt fusion protein overnight at 4° C. and were processed for GST immunoblotting. To control for protein loading, the blots were stripped and reprobed for MYC.

Co-Immunoprecpitation: Examples 2-13

Serum-starved PC-31-V, PC-31-CTRwt or PC-31-CTRΔESS cells (2×10$^6$ per 100 mm dish) were stimulated with or without 50 nM CT for 3 min, washed, and lysed in the IP buffer as previously described (von Zastrow et al., 1994). CTR in normalized lysate proteins was immunoprecipitated with anti-FLAG EZ-view beads (Sigma Chemical Co., St. Louis, Mo.), and eluted with FLAG peptide (600 μg/ml in PBS). CTR immunoprecipitates were processed for ZO-1 immunoblotting. To control for protein loading and transfer, the blots were stripped and reprobed with immunoprecipitating antibody.

Co-Immunoprecpitation: Examples 14-20

Postconfluent PC-3-CTRwt cells were treated with/without 50 nM CT for 10 min, lysed; and cell lysates were incubated with anti-ZO-1 antibody followed by Protein G cross-linked agarose beads. ZO-1 immunoprecipitates were processed for immunoblotting with specific antibodies against appropriate tight junction (TJ) proteins, followed by HRP-conjugated secondary antibody; the blots were then developed with enhanced chemoluminescense (ECL). Where radiolabeled phosphate was used, the blots were autoradiographed. To control for protein loading and transfer, the blots were stripped and reprobed with immunoprecipitating antibody.

Acceptor Photo-Bleaching Fluorescence Resonance Energy Transfer (FRET) Microscopy:

PC-3 cells were plated on glass bottom chambers and grown overnight. The cells were transfected with CTRwt-ECFP-N1 (or CTRΔESS-ECFP-N1) and ZO-1wt-EYFP-N1 (or ZO-1-ΔPDZ3-EYFP-N1) plasmids using Lipofectamine™, cultured for additional 36 h, and imaged live at room temperature using Nikon Eclipse 2000 TE connected with Sensicam-qe (Cooke Corporation, Romulus, Mich.). CFP and YFP images were acquired with excitation at 436 nm and emission at 480 and 535 nm respectively. A 505 nm dichroic filter set in Dual View was used to split the images (Optical Insights, Santa Fe, N. Mex.). FRET was recorded by monitoring the quenching of CFP during YFP photobleaching. The images were analyzed with IPLab 4.0 imaging software (Scanalytics, Inc, Rockville, Md.) and FRET efficiencies were calculated using the formula:

$$\text{FRET}_{Efficiency} = (\text{donor CFP}_{after\ bleaching} - \text{donor CFP}_{before\ bleaching})/\text{donor CFP}_{after\ bleaching}.$$

Thresholds for donor (CFP), acceptor (YFP), and FRET images were set at the beginning of data collection and were kept unchanged for the entire data set.

In Situ Proximity Ligation Assay (PLA):

Fixed PC cells or tissues were immunolabeled with primary antibodies (anti-rabbit ZO-1 serum and anti-goat CTR serum) for overnight at 4° C. The secondary antibodies with attached PLA probes were supplied in the Duolink™ kit (Olink Bioscience, Uppsala, Sweden). CTR-ZO-1 interaction was observed by confocal microscopy at 400×. A red fluorescent dot indicated the two proteins are within 35 nm distance. The number of dots per cell was determined by Blobfinder™ image analysis software (Allalou et al., 2009).

Measurement of Transepithelial Electric Resistance (TER) and Paracellular Permeability (PCP):

Cells were plated on Transwell filters (0.4 μm pore size) and grown to confluency in complete medium (RPMI1640 containing 10% fetal bovine serum, 20 mM HEPES and antibiotics). TER of the cultures (in duplicate wells) was measured at several time intervals with EVOM volt-ohm meter as previously described (Shah et al, 2009). The readings were corrected for blank (TER values from the filter in bathing medium). The integrity and cell density of monolayers were carefully monitored.

For PCP measurements, cells were grown to confluence on Transwell filters. Tetra methyl rhodamine-dextran (1 mg/ml, ~4 kDa, Sigma) was added to the upper chamber. Fluorescence of the lower chamber medium was measured in Modulus Microplate Reader (Turner Biosystems) at various time intervals.

In Vitro Invasion Assay:

Invasion experiments were conducted in Matrigel™ invasion chambers as previously described (Sabbisetti et al., 2005).

Orthotopic Tumor Growth and Metastasis:

To detect micrometastases of implanted tumor cells in mice, the cell lines were stably transfected with DsRed-MCherry-Hyg-N1 (Clontech, Palo Alto, Calif.). Hygromycin resistant colonies that expressed strong red fluorescence at a steady level over the observation period were selected, and used for orthotopic implantation.

CT, CTR Immunohistochemistry of PC Specimens:

CT/CTR immunopositive cell populations in PC tissue microarrays were determined as described previously (Shah et al., 2008). Incubations with rabbit anti-CT serum (Shah et al., 1992) or goat anti-CTR serum (Santa Cruz Biotechnology, Santa Cruz, Calif.) were followed by tetramethyl rhodamine isothiocyanate (TRITC)-conjugated secondary antiserum. The slides were then counterstained with 4',6-diamidino 2-phenylindole (DAPI), and scanned on a microarray scanner (Perkin Elmer, Waltham, Mass.). In addition, the image of every specimen was captured individually with a confocal microscope at 400×. CT/CTR-immunopositive cells per specimen were counted and scored.

Expression of CTRwt and CTRΔESS Receptors in PC-3 Cells:

To examine the importance of CTR-ZO-1 interaction in proinvasive actions of CTR, the CTR-C PDZ-binding motif was mutated by replacing the amino acids ESSA (SEQ ID NO:1) with the amino acids AAAA (SEQ ID NO:4) (this mutant is referred as CTRΔESS). PCR generated full length CTRwt and CTRΔESS cDNAs were cloned directionally into pcDNA3.1 mammalian expression vector as previously described. Both CTR constructs were FLAG-tagged at the 5' end. PCR products were sequenced to verify the sequence and orientation (Sanger et al., 1992). PC-3 cells (which lack endogenous CTR) were transfected with these constructs and stable cell lines expressing either CTRwt or CTRΔESS were prepared and characterized as described above.

Immunofluorescence of Tight Junction (TJ) Proteins:

Approximately 1×10$^4$ cells were grown to confluence on 0.4 μm 12-well Transwell™ filters (Costar, Mass.). After overnight serum starvation, cells were treated with or without 50 nM CT for 60 min, fixed with methanol and incubated with primary antisera (rabbit anti-ZO-1 IgG, Zymed, Calrsbad, Calif.; Claudin-3, CTR-FLAG). Immunostaining was visualized after incubation with TRITC-labelled secondary antibody (1:500). Controls with either non-immune goat IgG or no primary antisera were used in all studies. Digital photographs were taken with Retiga 1300 camera connected to a Nikon Optiphot-2 microscope equipped for epifluorescence, the images were captured at different wavelengths for TRITC and DAPI, were given red and blue pseudo colors respectively, and analyzed using IP Lab™ image analysis program.

Preparation of Triton X-100-Soluble and -Insoluble Cell Lysates and Western Blotting:

Confluent 100 mm plates of each PC sublines were serum starved overnight, and treated with or without 50 nM CT for various periods. Soluble extract (cytosolic) was obtained by incubating cells with 10 mM Tris-HCl, pH-7.4 (containing 150 mM NaCl, 2 mM CaCl$_2$, protease-phosphatase inhibitors cocktail, 1% Nonidet P-40 and 1% Triton-X-100) for 30 min with occasional agitation. After washing the plates with TBS (containing protease inhibitors), the insoluble fraction (plasma membrane-associated) was scraped out from the plates with TBS containing 0.5% SDS, 1% Nonidet P-40, protease inhibitors. The triton X-100-insoluble fraction was collected after homogenizing and centrifuging at 14,000×g for 5 min at 4 C, and protein content of the supernatants was determined using Bio-Rad Reagent (Bio-Rad, Hercules, Calif.).

The lysate fractions were boiled for 5 min in 2× Laemmli buffer. The proteins were fractionated by SDS-PAGE electrophoresis, and electrically transferred to a nitrocellulose membrane. The blots were incubated the appropriate antisera followed by HRP-conjugated secondary antibody; and the blots were developed with ECL. To control for protein loading and transfer, the blots were stripped, and reprobed with either β-actin (insoluble) or α-tubulin (soluble) antibody. The same experiment was repeated two more times.

In Vivo Phosphorylation and Immunoprecipitation:

Postconfluent cells cultured were serum-starved overnight, and then labeled with [$^{32}$P]orthophosphate (NEN/DuPont Chemicals) in phosphate-free serum-free Dulbecco's modified Eagle's medium for 3 hours at 37° C. The cells were then treated with calcitonin (CT) (50 nM for 10 min, 37° C.). When used, myristoylated PKA-inhibitory peptide (mPKI; 100 nM) was added 15 min prior to the addition of CT (50 nM). The cells were then washed with ice-cold phosphate-buffered saline, and lysed in 700 μl lysate buffer. The lysate was cleared by centrifugation for 10 min at 10,000×g. For immunoprecipitation, the supernatant was incubated overnight with primary antibody, and Protein A-Sepharose (40 μl, GE Healthcare) was added next morning. Washed immune complexes were fractionated on SDS-PAGE. The gels were either dried and exposed to film or transferred onto polyvinylidene difluoride membranes and immunoblotted as described above.

Phosphoserine and Phosphothreonine Immunoblotting:

Postconfluent cells were treated with CT (50 nM for 3 min) and lysed with modified RIPA buffer, and cell lysates were immunoprecipitated with anti-ZO-1 or anti-claudin-3 antibody as described above. The IPs were processed for immunoblotting with either anti-phosphoserine or anti-phosphothreonine antibodies followed by secondary antibody and developed with ECL To control for protein loading and transfer, the blots were stripped and reprobed with the immunoprecipitating antibody.

Statistical Analysis:

The results were statistically evaluated by One Way ANOVA analysis, and the levels of significance were derived from Newman-Keuls test. The difference was considered statistically significant when $p<0.05$.

Example 2

CTR Cytoplasmic (C) Tail Contains a Type I PDZ-Binding Motif.

Since CTR activated non-G protein-coupled signaling, its primary sequence was examined and found that the four terminal residues of CTR C-tail (aa 471-74, E-S-S-A (SEQ ID NO:1)) formed a canonical type I PDZ domain-binding motif. This motif was inactivated by replacing these residues with Alanine (A-A-A-A (SEQ ID NO:4); referred as "ΔESS").

Figure 1A:
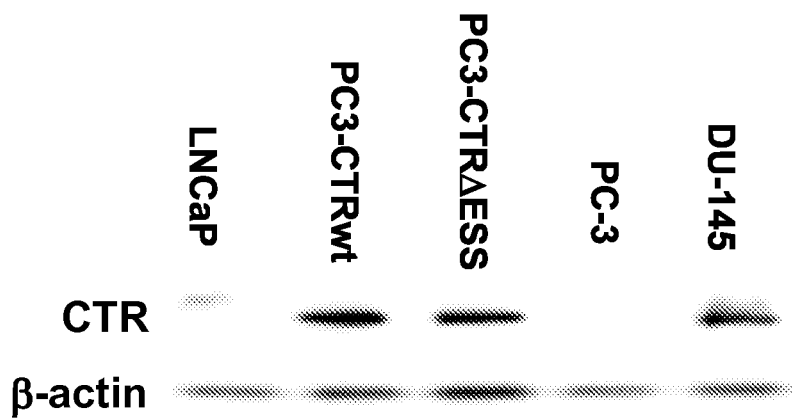
FIG. 1A depicts the effects of calcitonin (CT) in LNCaP, PC-3M and DU-145 prostate cancer cell lines, which endogenously express calcitonin receptors (CTRs). CTR immunoreactivity in plasma membranes of the cell lines (30 μg protein/lane) was determined by Western blot analysis, using β-actin for normalization.
Figure 1B:
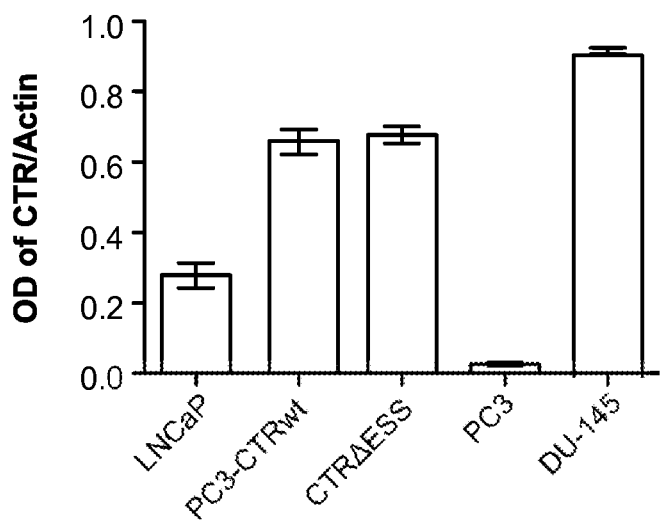
FIG. 1B depicts the optical density of CTR and actin bands on each Western blot obtained by image analysis on Kodak 4000 MM Image station (ratio of CTR OD/Actin OD±SEM; n=3).

CTRwt and CTRΔESS constructs were expressed in PC-3 cell line to generate PC-3CTRwt and PC-3CTRΔESS cell lines. PC-3 cells were chosen because they lack endogenous CTR and enable the study of the mutant CTR without interference from endogenous CTR. The levels of CTRwt or CTRΔESS were examined in plasma membranes of PC-3 stable lines with endogenous CTR levels in plasma membranes of other PC cell lines. As expected, PC-3 cells lacked CTR, and LNCaP cells displayed low levels of CTR. However, the levels of CTR in PC-3CTRwt and PC3-CTRΔESS cells were comparable to endogenous CTR levels of the poorly-differentiated DU-145 cell line as detected by immunoblotting. FIG. 1A depicts the effects of calcitonin (CT) in LNCaP, PC-3M and DU-145 prostate cancer cell lines, which endogenously express calcitonin receptors (CTRs). CTR immunoreactivity in plasma membranes of the cell lines (30 μg protein/lane) was determined by Western blot analysis, using β-actin for normalization. FIG. 1B depicts the optical density of CTR and actin bands on each Western blot obtained by image analysis on Kodak 4000 MM Image station (ratio of CTR OD/Actin OD ±SEM; n=3). As expected, PC-3 cells had little to no CTR, LNCaP had moderate levels, and DU-145 had the highest levels. The PC-3 cells with CTRwt or CTRΔESS inserted showed high levels of CTR.

Example 3

Mutation of CTR-C PDZ-Binding Motif does not Alter-subcellular Localization of CTR or its G Protein-Coupled Signaling.

Figure 1C:
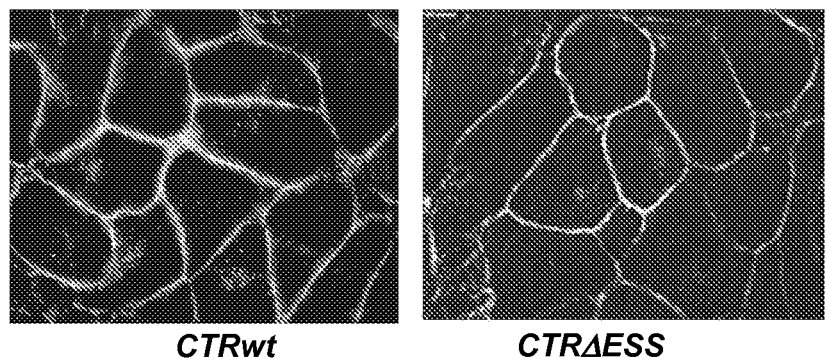
FIG. 1C depicts photomicrographs showing CTRwt and CTRΔESS (a mutant) localized to the plasma membrane (at 400×) in PC-3 cells.
Figure 1D:
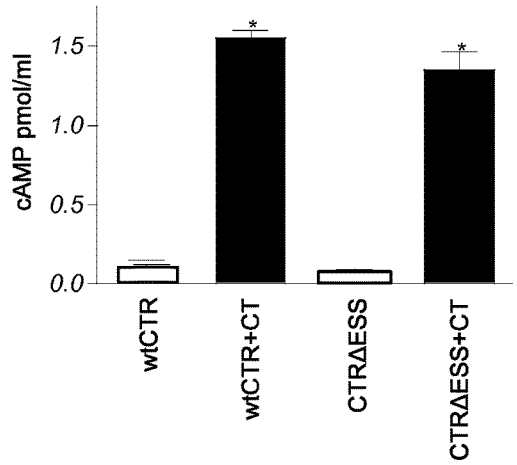
FIG. 1D depicts the effect of 50 nM CT on cAMP accumulation in PC-3 CTRwt and PC-3 CTRΔESS cells stimulated with/without 50 nM CT for 3 min. The cells were lysed, and the lysates were analyzed for cAMP levels by radioimmunoassay (*$p<0.01$ (paired t-test)).
Figure 1E:
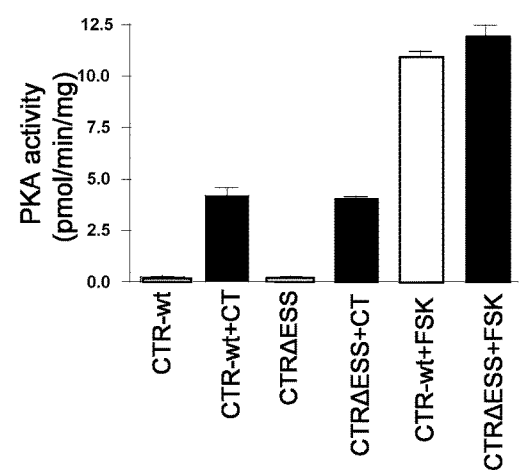
FIG. 1E depicts the effect of 50 nM CT on protein kinase A (PKA) activity in cell lysates of untreated and CT-treated PC-3 CTRwt and PC-3 CTRΔESS cells that were incubated with PKA substrate peptide and $^{32}$P-ATP, and also treated with forskolin, an activator of PKA.
Figure 1F:
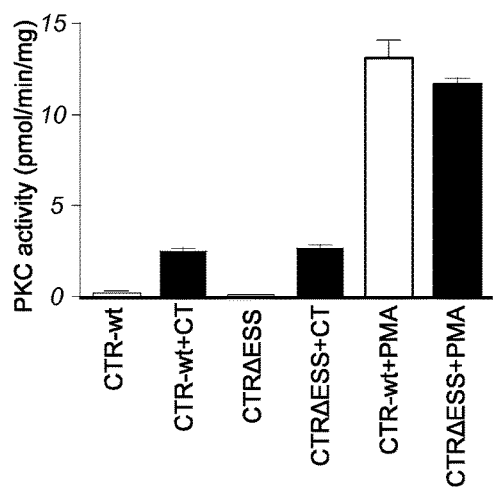
FIG. 1F depicts the effect of 50 nM CT on protein kinase C (PKC) activity in lysates of untreated and CT-treated PC-3 CTRwt and PC-3 CTRΔESS cells that were incubated with PKC substrate peptide and $^{32}$P-ATP, and also treated with phorbol 12-myristate 13-acetate (PMA), an activator of PKC.

Both CTRwt and CTRΔESS were localized to the plasma membrane as shown in FIG. 1C. FIG. 1C depicts photomicrographs showing CTRwt and CTRΔESS (a mutant) localized to the plasma membrane (at 400×) in PC-3 cells. To examine the ability of CTRwt and CTRΔESS to activate its G protein-coupled effectors, the effect of 50 nM CT was examined on cAMP accumulation and PKA and PKC activity. Both receptors caused similar increase in cAMP accumulation as well as PKA and PKC activity (FIGS. 1D-1F). FIG. 1D depicts the effect of 50 nM CT on cAMP accumulation in PC-3 CTRwt and PC-3 CTRΔESS cells stimulated with or without 50 nM CT for 3 min. The cells were lysed, and the lysates were analyzed for cAMP levels by radioimmunoassay (*p<0.01 (paired t-test)). The addition of CT stimulated cAMP production in both PC-3 CTRwt and PC-3CTRΔESS.

FIG. 1E depicts the effect of 50 nM CT on PKA activity in cell lysates of untreated and CT-treated PC-3 CTRwt and PC-3 CTRΔESS cells that were incubated with PKA substrate peptide and $^{32}$P-ATP, and also treated with an activator of PKA, forskolin (FSK). FIG. 1F depicts the effect of 50 nM CT on PKC activity in lysates of untreated and CT-treated PC-3 CTRwt and PC-3 CTRΔESS cells that were incubated with PKC substrate peptide and $^{32}$P-ATP, and also treated with an activator of PKC, phorbol 12-myristate 13-acetate (PMA).

Figure 1G:
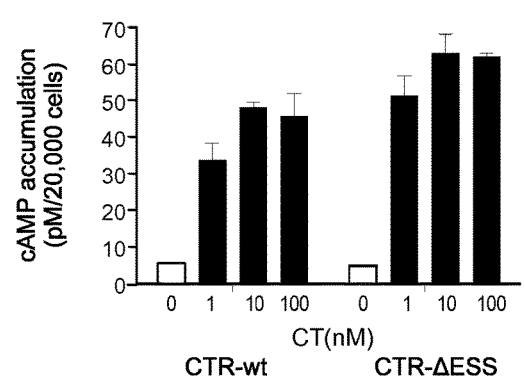
FIG. 1G depicts cAMP accumulation in PC-3 CTR and PC-3 CTRΔESS cells in response to CT at multiple doses (between 0-100 nM) stimulated for 3 min (*$p<0.01$ (One-way ANOVA and Newman-Keuls test)).

The effect of CT on cAMP was further tested in a dose-response study where the response to CT at multiple doses (between 0-100 nM) was examined. FIG. 1G depicts cAMP accumulation in PC-3 CTR and PC-3 CTRΔESS cells in response to CT at multiple doses (between 0-100 nM) stimulated for 3 min (*p<0.01 (One-way ANOVA and Newman-Keuls test)). Once again, both CTRwt and CTRΔESS cells significantly increased cAMP accumulation at all doses, and responses of both receptors were similar (FIG. 1G). Taken together, these results indicate that ΔESS mutation in CTR does not alter either the localization of CTR on PC-3 cell membranes or its ability to activate $G_{\alpha}s$ and $G_{\alpha}q$ signaling.

Example 4

CTR-C PDZ-Binding Motif is Required for the Action of CTR on TJ Stability and Invasion

Figure 2A:
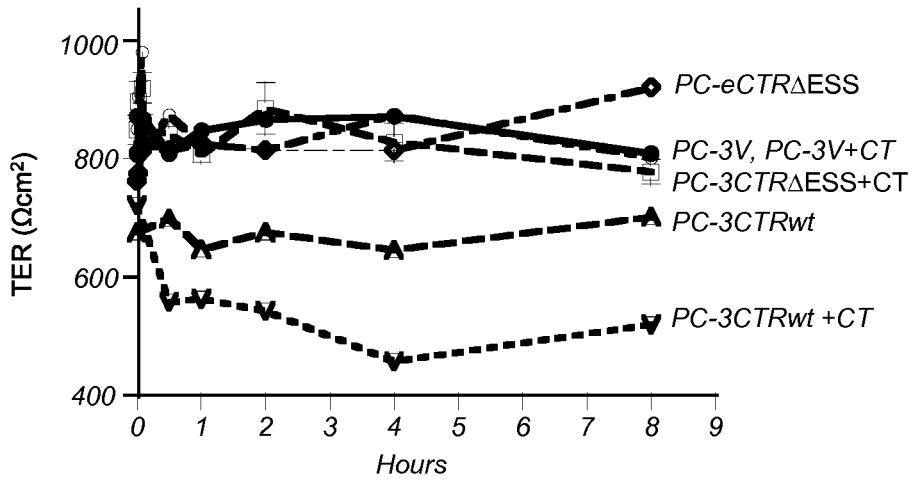
FIG. 2A depicts CTR-C PDZ-binding motif mutation and tight junction (TJ) disruption as measured using transepithelial electric resistance (TER). Polarized PC-3V, PC-3 CTRwt and PC-3 CTR-ΔESS cells were serum-starved for 4 hours, then treated with/without 50 nM CT. Transepithelial electric resistance was measured with EVOM volt-ohm meter, and results are expressed as ($\Omega cm^2 \pm SEM$; n=6).
Figure 8A:
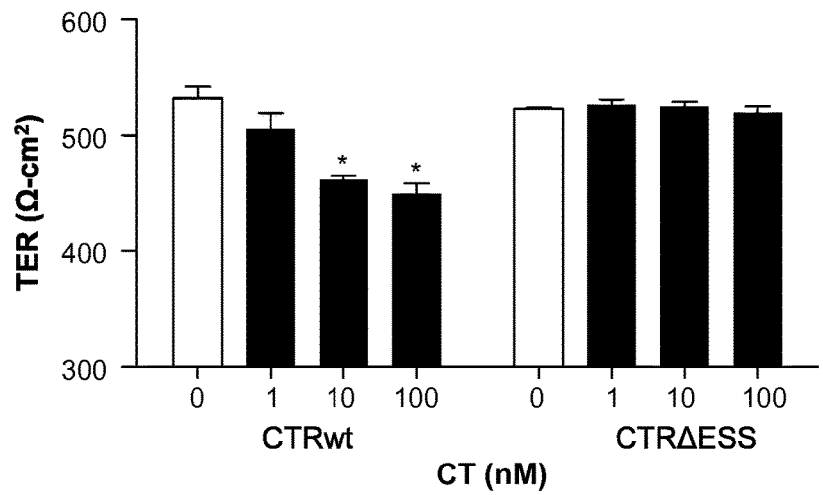
FIG. 8A depicts CTR-C PDZ-binding motif mutation and tight junction (TJ) disruption as CT concentration increases and as measured using transepithelial electric resistance (TER). Polarized PC-3 CTRwt and PC-3 CTR-ΔESS cells were serum-starved for 4 hours, then treated with various concentrations of CT. Transepithelial electric resistance was measured with EVOM volt-ohm meter, and results are expressed as ($\Omega cm^2 \pm SEM$; n=6).

A. TER:

To examine the effect of calcitonin (CT) on tight junctions (TJs), the transepithelial electric resistance (TER) of polarized PC-3 cells expressing either the vector (PC-3V), CTRwt or CTRΔESS was monitored for 8 hours after CT stimulation (FIG. 2A). Polarized PC-3V, PC-3 CTRwt and PC-3 CTR-ΔESS cells were serum-starved for 4 hours, then treated with or without 50 nM CT. TER was measured with EVOM volt-ohm meter, and results expressed as $\Omega cm^2 \pm SEM$ (n=6). Polarized PC-3V cells displayed relatively high TER, and CT did not alter it (FIG. 2A). Since PC-3 cells secrete CT, the expression of CTRwt may have activated CT-CTR axis causing almost 40% reduction of TER in PC-3CTRwt cells. Exogenous CT decreased TER even further. However, expression of CTRΔESS in PC-3 cells did not affect TER even after CT stimulation. When tested at multiple CT concentrations, a significant decrease in TER of PC-3CTRwt cells was observed at CT concentrations of 10 and 100 nM. However, PC-3CTRΔESS cells did not show any changes in TER at all CT concentrations (FIG. 8A).

Figure 2B:
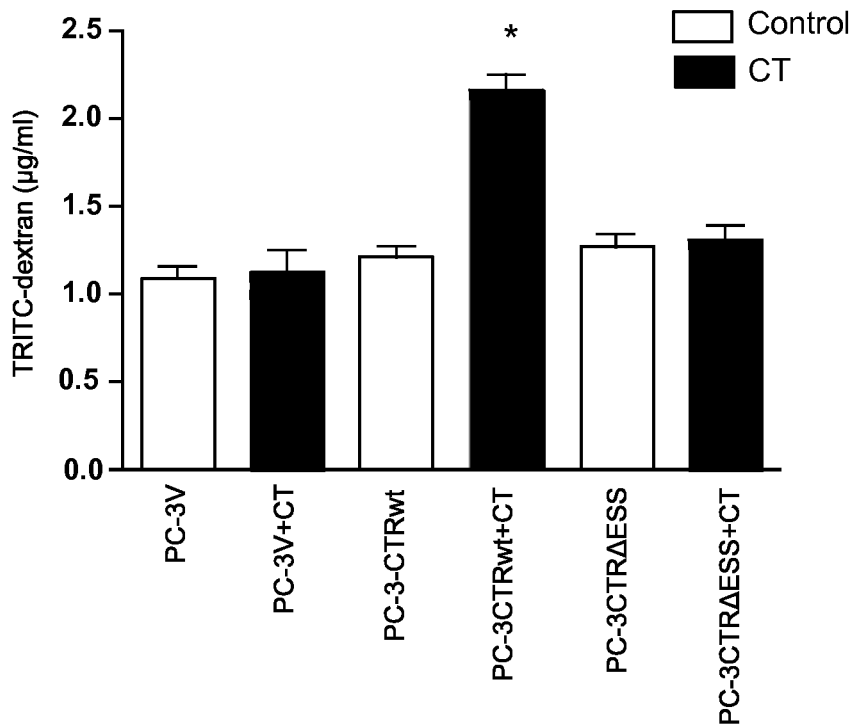
FIG. 2B depicts CTR-C PDZ-binding motif mutation and tight junction (TJ) disruption as measured using paracellular permeability (PCP). Polarized PC-3V, PC-3-CTRwt and PC-3CTRΔESS cells were treated with/without 50 nM CT, and paracellular permeability determined by diffusion of ~4 kDa TRITC-conjugated dextran from the upper to the lower chamber in one hour. The results are expressed as µg/ml/hour of TRITC-Dextran diffused ±SEM (n=6; *$p<0.05$ (−CT v +CT, One way ANOVA and Newman-Keul's test)).
Figure 8B:
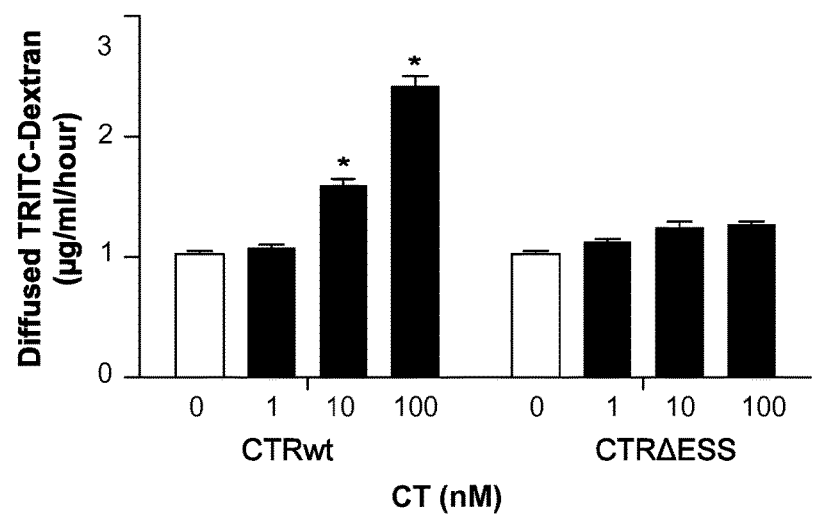
FIG. 8B depicts CTR-C PDZ-binding motif mutation and tight junction (TJ) disruption as CT concentration increases and as measured using paracellular permeability (PCP). Polarized PC-3V, PC-3-CTRwt and PC-3CTRΔESS cells were treated CT, and paracellular permeability determined by diffusion of ~4 kDa TRITC-conjugated dextran from the upper to the lower chamber in one hour. The results are expressed as μg/ml/hour of TRITC-Dextran diffused ±SEM (n=6; *p<0.05 (−CT v +CT, One way ANOVA and Newman-Keul's test)).

B. PCP:

TJs form a barrier that regulates the movement of ions, solutes and growth factors between cells. To detect whether CT affects the barrier, the diffusion of fluorophore-conjugated dextran was measured across polarized PC cell line monolayers, a procedure called paracellular permeability (PCP). FIG. 2B depicts CTR-C PDZ-binding motif mutation and tight junction (TJ) disruption as measured using PCP. Polarized PC-3V, PC-3-CTRwt and PC-3CTRΔESS cells were treated with or without 50 nM CT, and PCP determined by diffusion of ~4 kDa TRITC-conjugated dextran from the upper to the lower chamber in one hour. The results are expressed as μg/ml/hour of TRITC-Dextran diffused ±SEM (n=6; *p<0.05 (−CT v +CT, One way ANOVA and Newman-Keul's test)). PC-3V cells displayed relatively low PCP and exogenous CT did not alter it (FIG. 2B). Expression of CTRwt in PC-3 cells caused a small increase in their PCP, but the addition of CT increased PCP significantly. In contrast, CTRΔESS expression had little effect on PCP in the presence or absence of CT. Similar to TER, CT induced an increase in PCP of PC-3CTRwt cells at the doses of 10 nM or higher. Again, CT did not alter PCP of PC-3CTRΔESS cells at all tested concentrations (FIG. 8B).

Figure 2C:
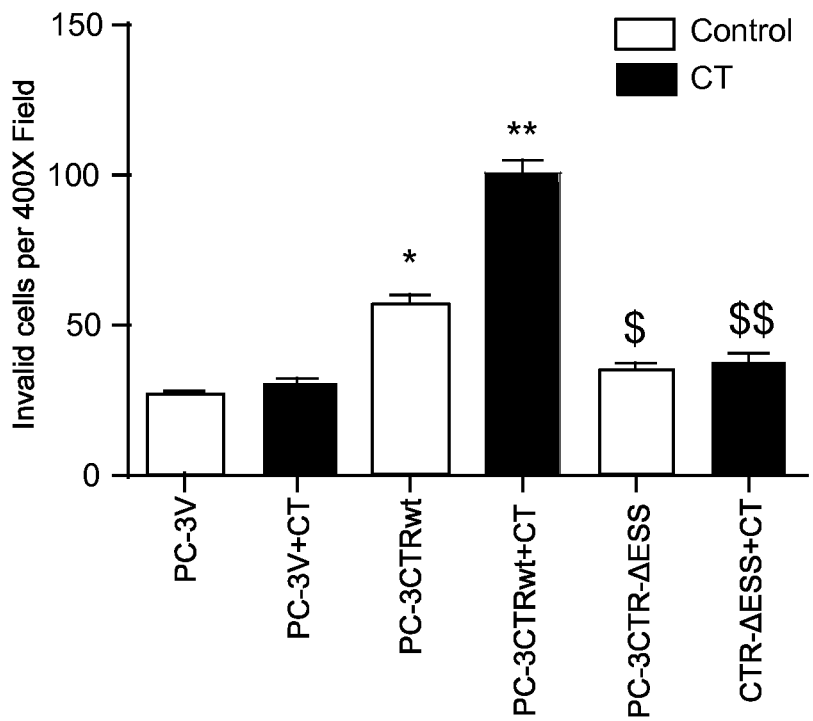
FIG. 2C depicts CTR-C PDZ-binding motif mutation and effects on cell invasion. PC-3V, PC-3 CTRwt and PC-3 CTRΔESS cells were added to upper insert of invasion chambers with/without 50 nM CT, and cells that passed through the Matrigel™ barrier were counted after 48 h. The results are expressed as mean number of invaded cells per 400× field ±SEM (n=6; *$p<0.05$ (PC-3V v PC-3CTR-wt); $ $p<0.05$ (PC-3CTR-wt v PC-3CTRΔESS); $$-$p<0.05$ (PC-3CTRwt+CT v PC-3CTRΔESS+CT) (one-way ANOVA and Newman-Keul's test)).

C. Invasion:

CT increases invasiveness, and even induces an invasive phenotype in non-invasive prostate cancer cells. The role of PDZ-binding motif in CT-stimulated invasion was examined. FIG. 2C depicts CTR-C PDZ-binding motif mutation and effects on cell invasion. PC-3V, PC-3 CTRwt and PC-3 CTRΔESS cells were added to upper insert of invasion chambers with or without 50 nM CT, and cells that passed through the Matrigel™ barrier were counted after 48 h. The results are expressed as mean number of invaded cells per 400× field ±SEM (n=6; *p<0.05 (PC-3V v PC-3CTR-wt); $ p<0.05 (PC-3CTR-wt v PC-3CTRΔESS); $$-p<0.05 (PC-3CTRwt+CT v PC-3CTRΔESS+CT) (one-way ANOVA and Newman-Keul's test)). Expression of CTRwt in PC-3 cells increased invasion by 2.5-fold (FIG. 2C). However, expression of CTRΔESS did not cause a similar increase. When stimulated with 50 nM CT, PC-3-CTRwt cells responded with an additional 2.5-fold increase in invasion, but PC-3CTRΔESS did not.

Figure 2D:
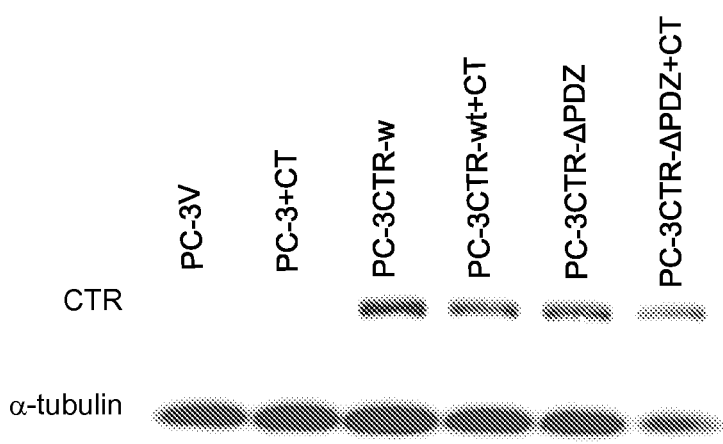
FIG. 2D depicts a representative Western blot showing CTR immunoreactivity in cell lysates from PC-3V, PC-3 CTRwt and PC-3 CTRΔESS cells treated with/without 50 nM CT.

Since CTRwt and CTRΔESS had dramatically different effects on TER, PCP and invasion, experiments were conducted to make certain that the variances were not due to differences in their CTR levels. FIG. 2D depicts a representative Western blot showing CTR immunoreactivity in cell lysates from PC-3V, PC-3 CTRwt and PC-3 CTRΔESS cells treated with or without 50 nM CT. CTR immunoreactive levels were similar in all cell lines in the presence or absence of CT (FIG. 2D), which suggests that the interaction of CTR with its partner protein through its PDZ binding motif is critical for its destabilizing actions on TJs and promoting invasion.

Example 5

CTR Also Destabilizes TJs and Increases Invasion of Other PC Cell Lines

Figure 9A:
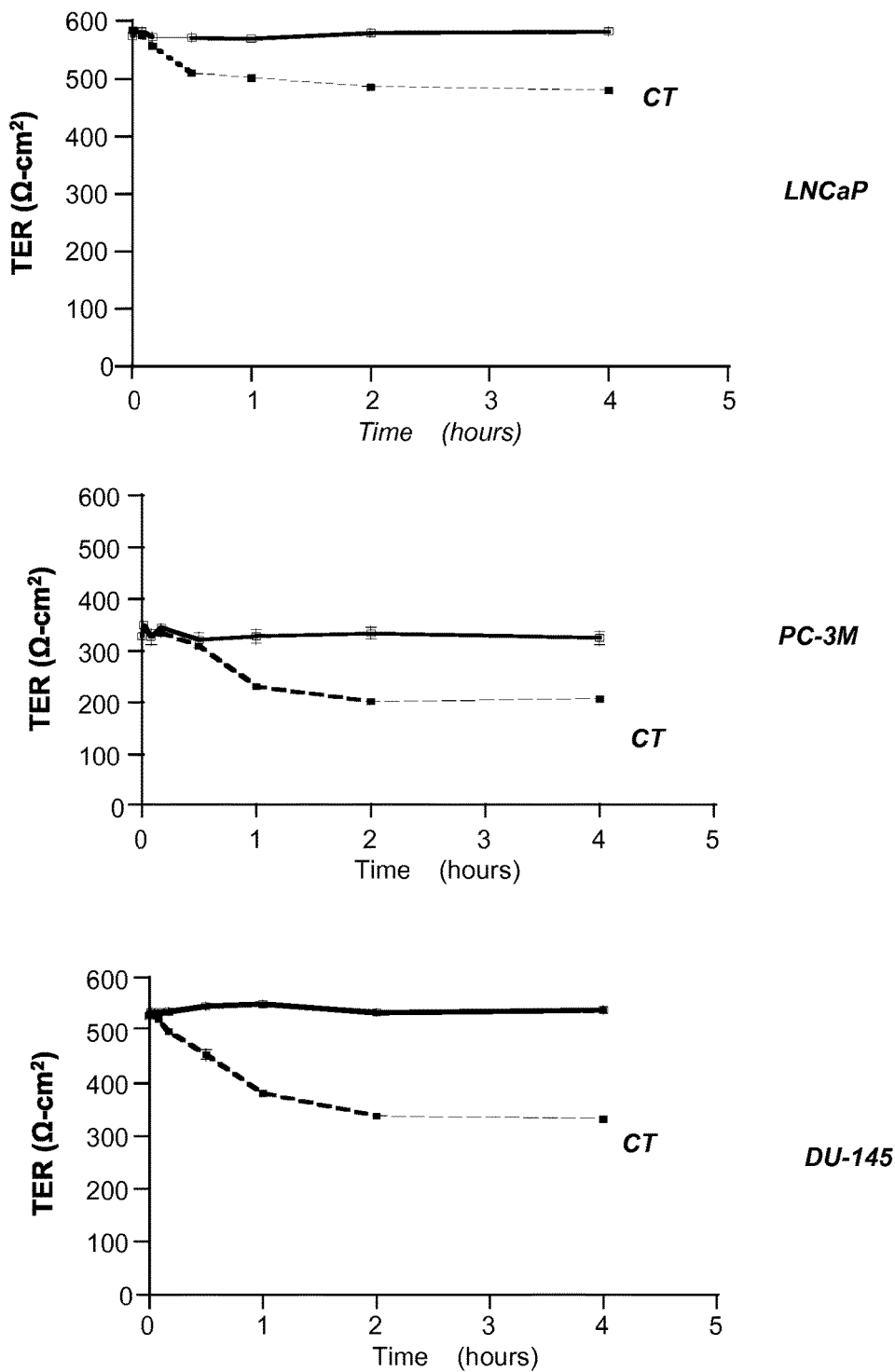
FIG. 9A depicts the effect of CT on tight junction (TJ) disruption as measured using transepithelial electric resistance (TER) in three prostate cancer cell lines—LNCaP, PC-3M, and DU-145. Cells were serum-starved for 4 hours, then treated with and without 50 nM CT. Transepithelial electric resistance was measured with EVOM volt-ohm meter
Figure 9B:
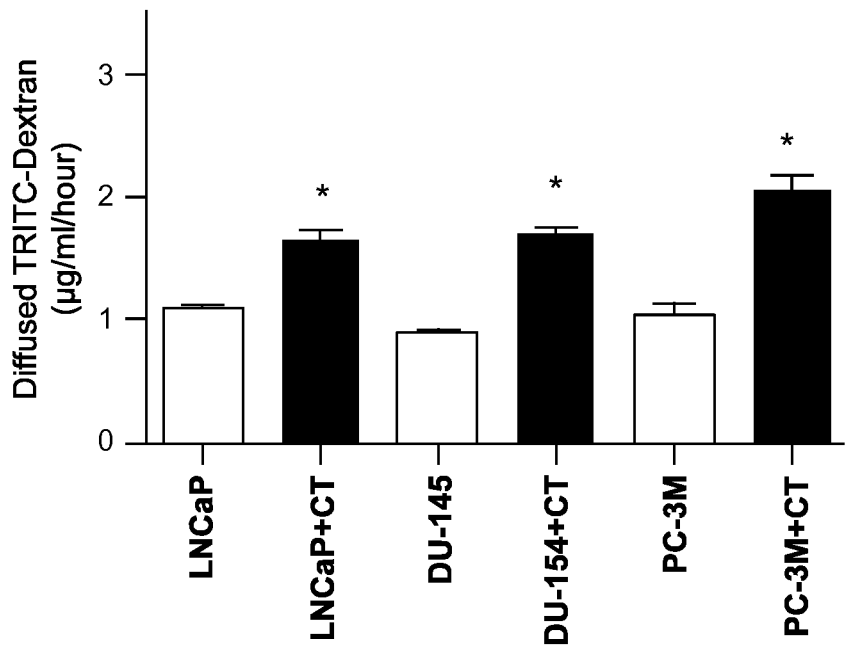
FIG. 9B depicts the effect of CT on tight junction (TJ) disruption as measured using paracellular permeability (PCP). Polarized LNCaP, PC-3M, and DU-145 cells were treated with and without 50 nM CT, and paracellular permeability determined by diffusion of ~4 kDa TRITC-conjugated dextran from the upper to the lower chamber in one hour. The results are expressed as μg/ml/hour of TRITC-Dextran diffused ±SEM (n=6; *p<0.05 (−CT v +CT, One way ANOVA and Newman-Keul's test))
Figure 9C:
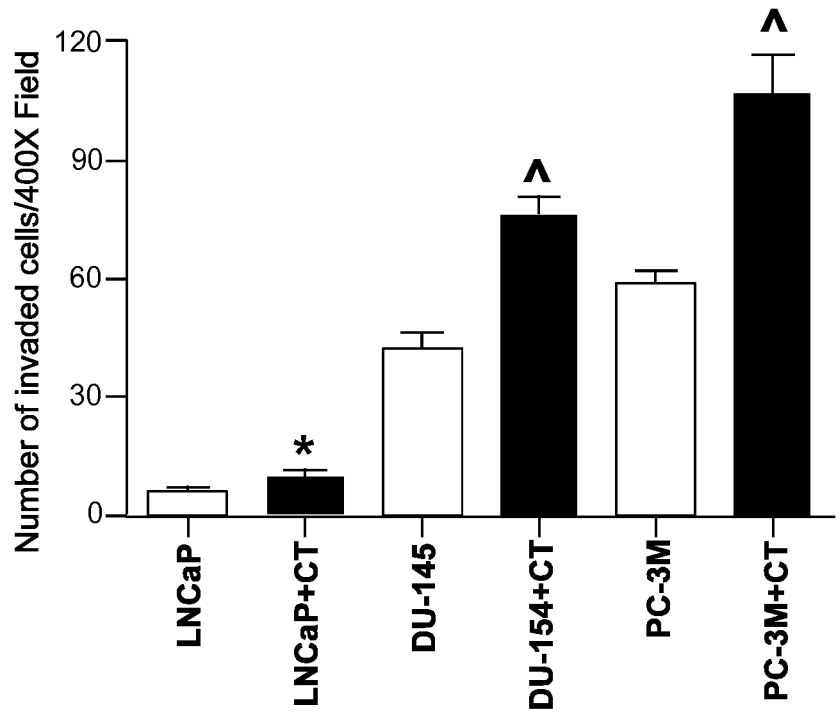
FIG. 9C depicts effects of CT on cell invasion. PC-3M, LNCaP, and DU-145 cells were added to upper insert of invasion chambers with/without 50 nM CT, and cells that passed through the Matrigel™ barrier were counted after 48 h. The results are expressed as mean number of invaded cells per 400× field ±SEM (n=6; *p<0.05).

Whether CT produces similar effects in LNCaP, PC-3M and DU-145 cell lines, which endogenously express CTR, was examined as shown in FIG. 1A. FIGS. 9A-9B depict the effect of CT on tight junction (TJ) disruption as measured using TER and PCP in the three prostate cancer cell lines—LNCaP, PC-3M, and DU-145. Cells were serum-starved for 4 hours, then treated with and without 50 nM CT, before measuring TER as described above. In FIG. 9B, cells were treated with and without 50 nM CT, and PCP determined by diffusion of ~4 kDa TRITC-conjugated dextran from the upper to the lower chamber in one hour. The results are expressed as μg/ml/hour of TRITC-Dextran diffused ±SEM (n=6; *p<0.05 (−CT v +CT, One way ANOVA and Newman-Keul's test)). FIG. 9C depicts effects of CT on cell invasion in the same three cell lines—PC-3M, LNCaP, and DU145. Cells were added to upper insert of invasion chambers with or without 50 nM CT, and cells that passed through the Matrigel™ barrier were counted after 48 h. The results are expressed as mean number of invaded cells per 400× field ±SEM (n=6; *p<0.05).

As shown in FIGS. 9A-9B, CT reduced TER and increased PCP of these cell lines, suggesting CT destabilizes TJs in androgen-responsive as well as androgen-refractory PC cell lines. Similarly, CT significantly increased invasion of LNCaP cells, which displayed very low invasion, as well as more invasive DU-145 and PC-3M cells (FIG. 9C).

Example 6

Identification of CTR-Interacting Protein

Since the action of CTR on TJ stability and invasion required PDZ-binding motif, CTR-interacting protein was identified by Y2H complementation screening using as bait the 64 amino acid CTR C-tail of hCTR2 fused with the Gal-4 DNA binding domain. After screening $1\times10^6$ transformants, 11 interacting clones were identified, purified and sequenced. The results are shown in Table 1 below. Most positive clones encoded plasma membrane proteins and/or proteins associated with the adenylyl cyclase system. One clone encoded tight junction protein ZO-1, and this clone also provided the strongest signal in secondary screening. Since CTR destabilized TJs only in the presence of PDZ-binding motif, CTR-ZO-1 interaction was further characterized.

TABLE 1

| No: | Gene | X-Gal Score | Leu Score |
|---|---|---|---|
| 1 | PP1R9A-ERM domain | ++ | +++ |
| 2 | PDE9Av20 | + | +++ |
| 3 | tight junction protein 1 (TJP-1) (Zonula Occludens-1) | +++ | +++ |
| 4 | SNX4-nexin-4 | ++ | +++ |
| 5 | apoptosis-inducing factor-PDCD8 | ++ | +++ |
| 6 | vigilin-high density lipoprotein binding protein | + | +++ |

TABLE 1-continued

| No: | Gene | X-Gal Score | Leu Score |
|---|---|---|---|
| 7 | SMARCA4 | ++ | +++ |
| 8 | MAPK9v2 | ++ | +++ |
| 9 | Homo sapiens tumor-associated calcium signal transducer 2 (TACSTD2) | ++ | +++ |
| 10 | Homo sapiens transgelin (TAGLN), transcript variant 2, mRNA | + | +++ |
| 11 | Homo sapiens WNK lysine deficient protein kinase 4 (WNK4), mRNA | ++ | +++ |

Example 7

CTR-C-Tail Interacts with ZO-1.

Figure 3A:
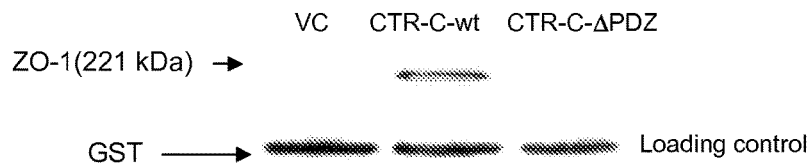
FIG. 3A shows a representative Western blot validating CTR-ZO-1 interaction with FLAG-CTR-C-pull down. The beads containing the GST-fusion proteins of C, CTR-C-wt and CTR-CΔESS (CTR-C-ΔPDZ) (2 µg protein) were incubated with PC-3 cell lysates for 6 h at 4° C., washed, and bound proteins were eluted with 5 mM reduced glutathione. ZO-1 was identified in the eluted proteins by immunoblotting.

GST Pull-down assay. CTR-C tail-ZO-1 interaction was examined using GST pull-down assays. Equal amounts of GST-C (negative control; a random sequence of equivalent length to CTR-C wt), GST-CTR-Cwt and GST-CTR-CΔESS fusion proteins (2 μg) were immobilized on gluthatione-Sepharose 4B beads, and were incubated individually with equal amount of PC-3 cell lysates. FIG. 3A shows a representative Western blot validating CTR-ZO-1 interaction with FLAG-CTR-C-pull down. The beads containing the GST-fusion proteins of C, CTR-C-wt and CTR-CΔESS (CTR-C-ΔPDZ) (2 μg protein) were incubated with PC-3 cell lysates for 6 h at 4° C., washed, and bound proteins were eluted and analyzed for ZO-1 immunoreactivity with 5 mM reduced glutathione. ZO-1 was identified in the eluted proteins by immunoblotting. As shown in FIG. 3A, only the CTR-C-wt fusion protein, but not CTR-CΔESS or GST-C, pulled ZO-1 immunoreactivity down.

Co-Precipitation.

Figure 10A:
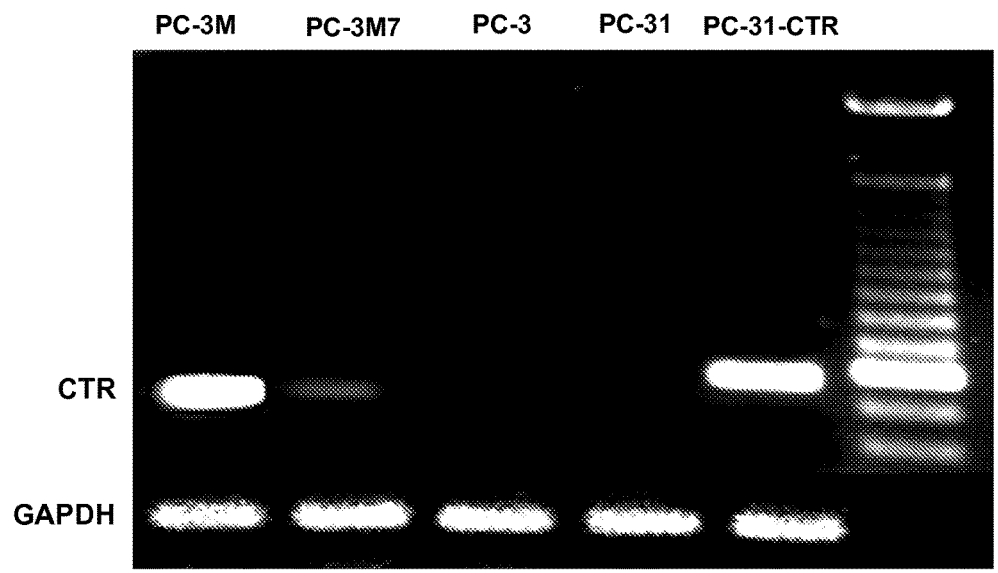
FIG. 10A depicts the presence or absence of CTR transcripts in several prostate cancer cells lines (PC-3M, PC-3M7, PC-3, PC-31, and PC-31+CTR) where CTR immunoreactivity in plasma membranes of the cell lines (30 μg protein/lane) was determined by Western blot analysis, using GAPDH for normalization.
Figure 10B:
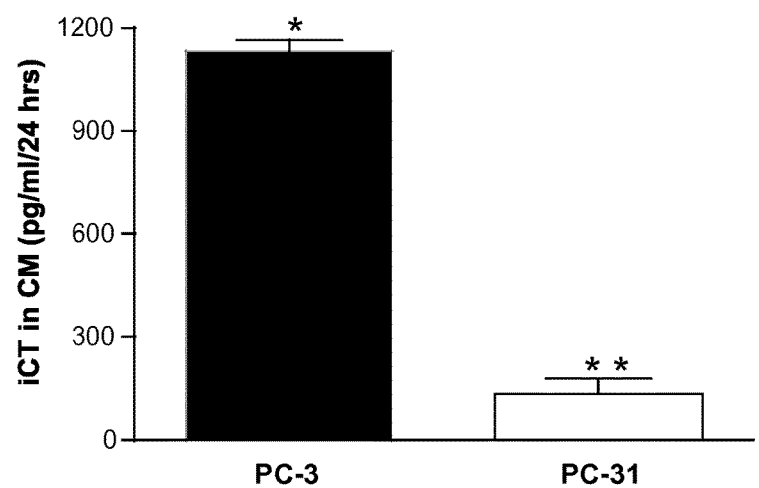
FIG. 10B shown the level of CT secretion in two cell lines—PC-3 and PC-31 as measured by ELISA. PC-3 and PC-31 cells were plated at a density of 100,000 cells perwell in 24-well culture plates. Once confluent, the complete medium was replaced with basal medium. The basal medium after 24 hour was collected and analyzed for CT content by ELISA.
Figure 10C:
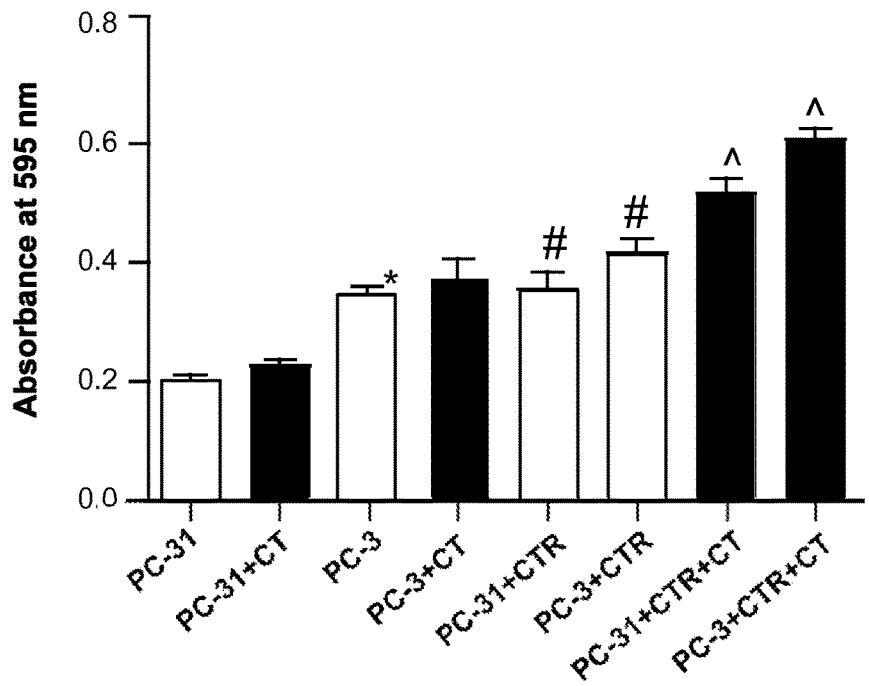
FIG. 10C depicts the effects of CT on cell proliferation rate in PC-31, PC-3, PC-3+CTR, and PC-31+CTR as measured as increase in absorbance at 595 nm.
Figure 10D:
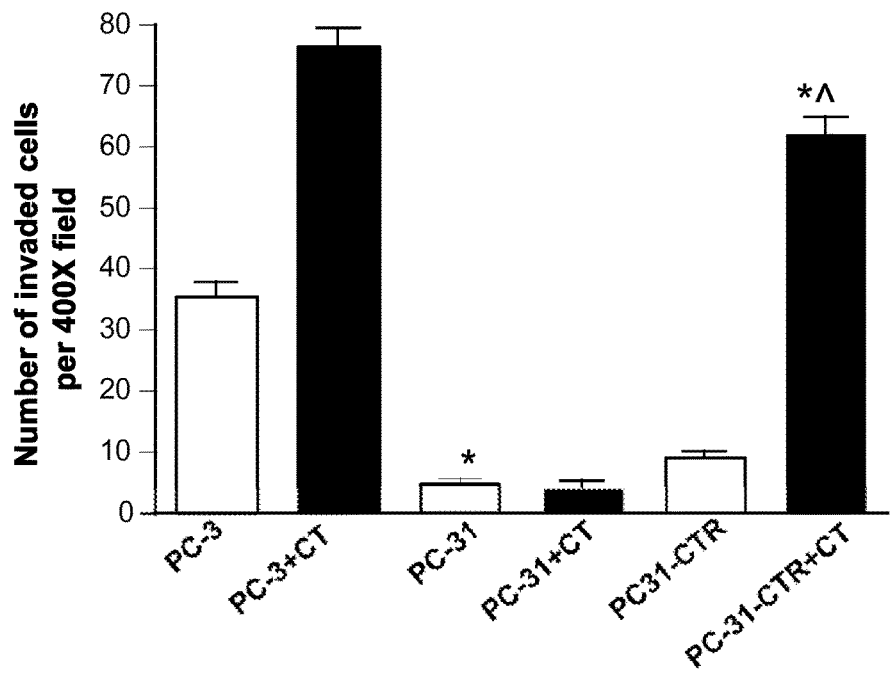
FIG. 10D depicts effects of CT on cell invasion. PC-3, PC-31, PC-3+CTR, and PC-31+CTR cells were added to upper insert of invasion chambers with/without 50 nM CT, and cells that passed through the Matrigel™ barrier were counted after 48 h. The results are expressed as mean number of invaded cells per 400× field ±SEM (n=6; *p<0.05).

To confirm CTR and ZO-1 interaction in a more physiological context, co-immunoprecipitation studies were performed. To avoid activation of CTR by endogenous CT in PC-3 cells, the PC-31 cell line that lacks both endogenous CT and CTR was used (FIGS. 10A and 10B). FIG. 10A shows the presence or absence of CTR transcripts in several prostate cancer cells lines (PC-3M, PC-3M7, PC-3, PC-31, and PC-31+CTR) where CTR immunoreactivity in plasma membranes of the cell lines (30 μg protein/lane) was determined by Western blot analysis, using GAPDH for normalization. As shown in FIG. 10A, both PC-3 and PC-31 cells lack CTR transcripts. FIG. 10B shows the level of CT secretion in PC-3 and PC-31 and indicates CT secretion in PC-3 and low secretion in PC-31 cells.

Figure 3B:
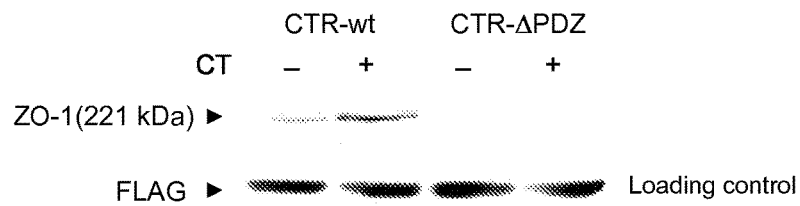
FIG. 3B shows a representative Western blot validating CTR-ZO-1 interaction with co-precipitation of CTR-FLAG with ZO-1. PC-31 FLAG-CTR-wt and PC-31 FLAG-CTR-ΔPDZ cells were treated with 50 nM CT for 3 min. CTR-FLAG was immunoprecipitated, the immunoprecipitates (IPs) were fractionated on SDS-PAGE, and ZO-1 was detected by immunoblotting.
Figure 8C:
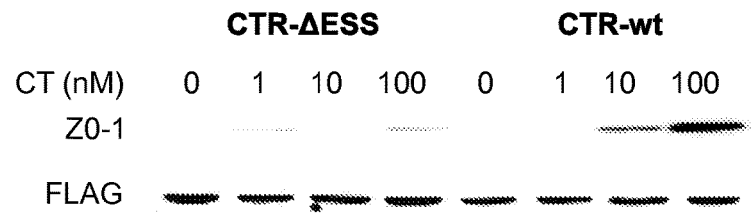
FIG. 8C shows a representative Western blot validating CTR-ZO-1 interaction with co-precipitation of CTR-FLAG with ZO-1 as CT concentration increases. PC-31 FLAG- CTR-wt and PC-31 FLAG-CTR-ΔESS cells were treated with various concentrations of CT for 3 min. CTR-FLAG was immunoprecipitated, the immunoprecipitates (IPs) were fractionated on SDS-PAGE, and ZO-1 was detected by immunoblotting

PC-31 cells stably expressing either FLAG-CTRwt or FLAGCTRΔESS were treated with or without CT for 3 min. The analysis of FLAG-CTR IPs confirmed that only FLAG-CTRwt, but not FLAG-CTRΔESS, co-precipitated ZO-1 (FIG. 3B). Interestingly, ligand-activated FLAG-CTRwt precipitated ZO-1 much more efficiently than dormant FLAG-CTRwt. The effect of multiple CT concentrations on CTR-ZO-1 co-precipitation was tested in PC-3 cells. As presented in FIG. 8C, it appears that co-precipitation of ZO-1 by CTRwt was barely detectable in the absence or presence of 1 nM CT. However, co-precipitation of ZO-1 by CTRwt was strong in PC-3 cells stimulated with 10 nM CT, and was even stronger in the cells receiving 100 nM CT. In contrast, ZO-1 was not co-precipitated by CTRΔESS at all CT concentrations (FIG. 8C). These results are consistent with those of FIGS. 8A and 8B.

Example 8

Identification of CTR-C Interaction Site on ZO-1.

Figure 3C:
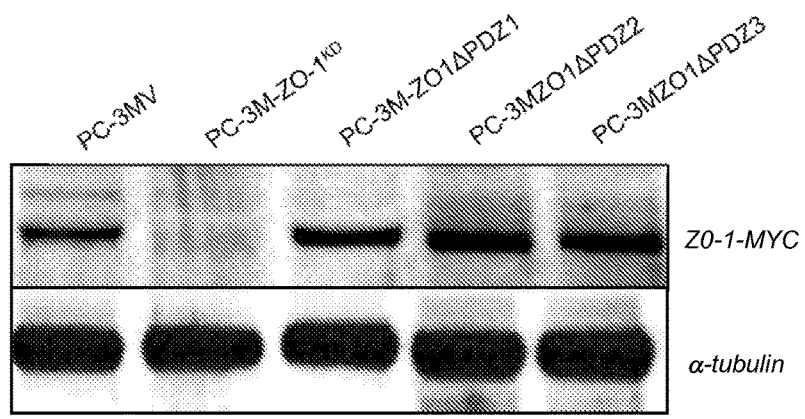
FIG. 3C shows PC-3M cells stably transfected with pSuperNeo expressing a scrambled control (SC) or ZO-1 siRNA, and then transfected with ZO-1wt or its ΔPDZ mutants. Cell lysates were tested for ZO-1 or mutants tagged with MYC protein by MYC immunoblotting.
Figure 3D:
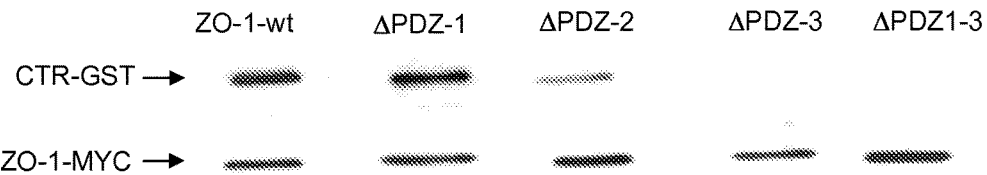
FIG. 3D depicts a representative Western blot of proteins from cell lysates expressing either ZO-1wt-MYC or ZO-1ΔPDZ-MYC (ΔPDZ-1 denotes PDZ-1 mutated with other PDZ domains intact). After separating the proteins by a gel, the proteins were transferred to a blot and incubated with GST tagged CTR-wt fusion protein overnight at 4° C. The blots were then washed and initially immunoprobed for GST, and then stripped and reprobed for MYC protein.

Overlay Assay:

Since ZO-1 contains three PDZ domains, which of these interacts with CTR-C PDZ-binding motif was analyzed. PC-3M cells was used for this study because they are PC-3-derived, but co-express both CT and CTR, and are suitable to examine modulation of CTR action in response to mutations in ZO-1 (Chien et al., 2001). To knock down endogenous ZO-1 expression, PC-3M cells were stably transfected with constitutive ZO-1 shRNA expression vector (pSuper.neo system; shRNA duplex-5'-GACGA-GAUAAUCCUCAUUUtt-3' (SEQ ID NO:8) corresponding to 596-614 bp of ZO-1 mRNA). Since the constitutive presence of ZO-1 siRNA in PC-3M cells could interfere with the re-expression of ZO-1 wt or its ΔPDZ mutants, ZO-1 (wt or ΔPDZ mutants) cDNA expression vectors refractory to ZO-1 RNAi were generated by introducing a silent mutation in RNAi target sequence in the ZO-1 transgene. The cells were then transfected with either ZO-1-wt or a ZO-1-ΔPDZ transgenes, where either one (ΔPDZ1, ΔPDZ2 or ΔPDZ3) or all three PDZ domains [ΔPDZ (1-3)] were deleted. Knockdown of ZO-1 as well as its re-expression was verified by Western blotting (FIG. 3C). All ZO-1 plasmids were myc-tagged. The lysates from these cells were fractionated on SDS-PAGE and transferred to PVDF membrane. After incubation with GST-CTRwt fusion protein, the blots were probed first for GST and then for MYC immunoreactivity (FIG. 3D). ZO-1-wt as well as ZO-1-ΔPDZ1 and ΔPDZ2 bound CTRwt-GST. However, deletion of either PDZ3 or PDZ (1-3) abolished the ability of ZO-1 to bind CTRwt-GST, suggesting CTR-C interacts with ZO-1 at its PDZ3 domain.

Example 9

CTR-C PDZ-Binding Motif-ZO-1-PDZ3 Interaction in Live PC Cells: Acceptor Photobleaching FRET Microscopy.

To verify CTR and ZO-1 interaction in live cells, acceptor photobleaching fluorescence resonance energy transfer (FRET) microscopy was employed (Karpova et al., 2006). PC-31 cells were transfected with CTR-wtCFP (or CTR-ΔESSCFP) and ZO-1-wtYFP (or ΔPDZ3-ZO-1YFP). Both ZO-1 and CTR were found localized to the plasma membrane (FIG. 4A, Columns 2 and 3 respectively). The cells appear rounded because the experiment was done within 36 hours of transfection. Increase in the intensity of CFP with YFP bleaching suggested energy transfer or interaction; no change in CFP intensity suggested lack of interaction. The results of FIG. 4B show that the addition of CT (50 nM) caused a visible increase in CFP intensity (Column B5=B4−B3), suggesting an interaction of CTR with ZO-1. Mean FRET efficiency of the resting CTR-wt-ZO-1-wt pair was 8.419±0.962 (n=8; separate experiments) suggesting a weak interaction (FIG. 4A). CT stimulation increased Mean FRET efficiency to 97.38±10.04, suggestive of moderately strong interaction (FIG. 4B). However, neither the CTR-ΔESSCFP: ZO-wt-YFP nor CTR-wt-CFP:ZO-1-ΔPDZ3-YFP FRET pairs demonstrated any interaction in the presence or absence of CT (FIGS. 4C-4F). These results again confirm that the interaction of CTR with ZO-1 requires the CTR-C PDZ-binding motif and the ZO-1-PDZ3 domain. Activated CTRwt displays stronger interaction with ZO-1 than the resting CTRwt, consistent with the data of co-immunoprecipitation presented in FIG. 3B.

Example 10

ZO-1-PDZ3 Deletion Abrogates the Action of CTR on Tight Junctions and Invasion.

Figure 5A:
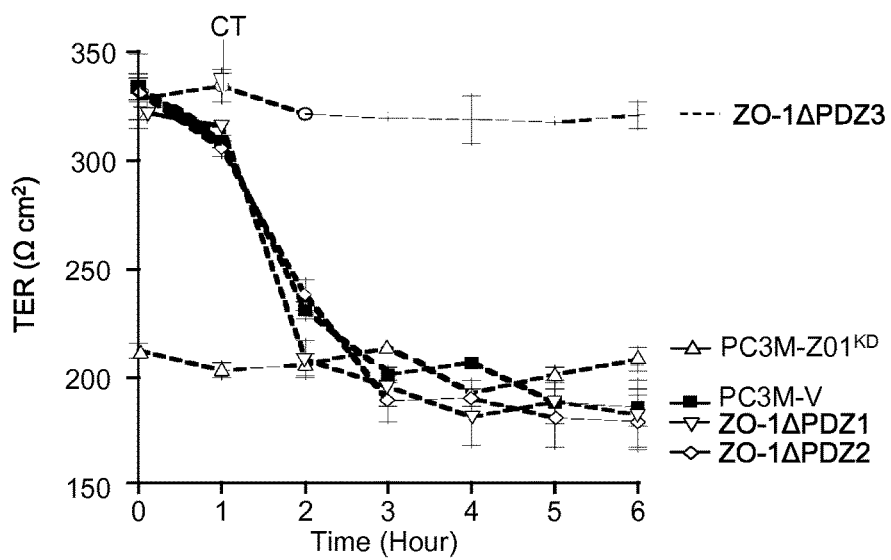
FIG. 5A depicts the effects of ZO-1 mutants and CTR-stimulation on transepithelial electric resistance (TER). Transepithelial electric resistance of polarized PC-3M cells or those expressing ZO-1 mutants (as labeled) was measured at several time points after stimulation with 50 nM CT ($\Omega cm^2 \pm SEM$; n=6). PC-3M cells used were characterized for endogenous ZO-1 expression as discussed in FIG. 3C.
Figure 5B:
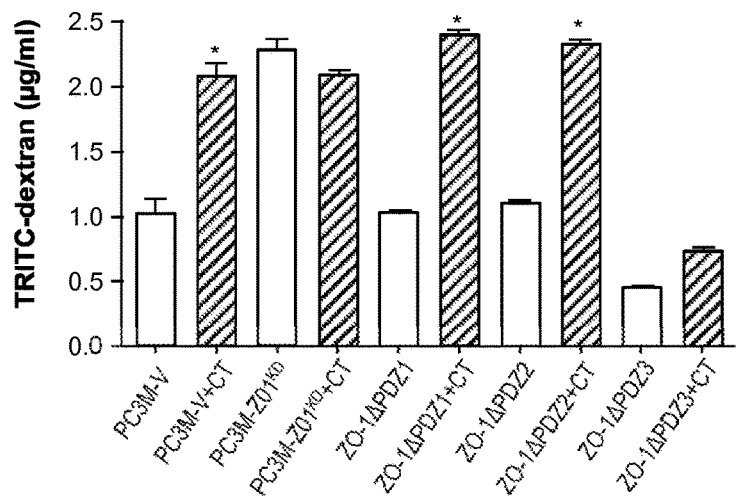
FIG. 5B depicts the effects of ZO-1 mutants and CTR-stimulation on paracellular permeability (PCP). Paracellular permeability of polarized PC-3M cells or those expressing ZO-1 mutants (as labeled) was measured as described above in FIG. 2B. The results are expressed as μg/ml/hour of TRITC-Dextran diffused±SEM (n=6; *p<0.05 significantly different from PC-3M V cells (one-way ANOVA and Newman-Keul's test)). PC-3M cells used were characterized for endogenous ZO-1 expression as described in FIG. 3C.
Figure 5C:
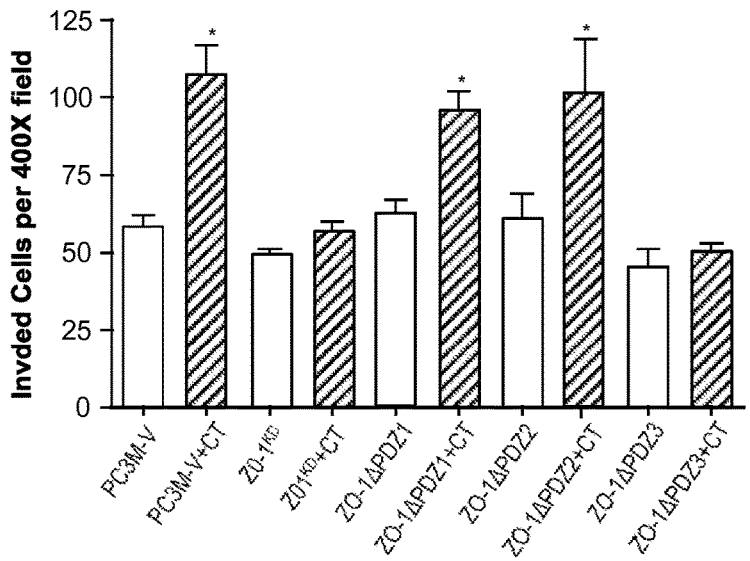
FIG. 5C depicts the results of ZO-1 mutants and CTR-stimulation on cell invasion. PC-3M cells or those expressing ZO-1 mutants (as labeled) were treated with/without 50 nM CT, and cells that passed through the Matrigel Barrier™ were counted after 48 hours. The results are expressed as mean number of invaded cells per 400× field ±SEM (n=6; *p<0.05 significantly different from PC-3MV cells (one way ANOVA and Newman-keul's test)). PC-3M cells used were characterized for endogenous ZO-1 expression.

To determine the functional significance of each ZO-1 PDZ domain in CTR-ZO-1 interaction, the effect of CT was examined on TJs and invasion in cells expressing ZO-1-wt or its ΔPDZ mutants. PC-3M-ZO-1 k/d cells had a lower TER relative to PC-3M-V cells (vector control) or those re-expressing ZO-1-wt or its ΔPDZ variants (FIG. 5A). Re-expression of ZO-1wt or its ΔPDZ variants restored their TER closer to that of PC-3M-V cells. Moreover, the cells re-expressing ZO-1-wt or its ΔPDZ1 and ΔPDZ2 variants responded to CT with a remarkable decline in TER. In contrast, the cells expressing ZO-1-ΔPDZ3 showed no decrease in TER following exposure to CT. A similar trend was observed when PCP and cell invasion were examined (FIGS. 5B and 5C respectively). Specifically, the third PDZ domain was required for cellular response to CT activation. These results corroborate the findings of FIGS. 3D, 4E and 4F that the loss of PDZ3, but not the PDZ1 or 2 domains, abrogates CT-stimulated TJ destabilization and invasion.

Example 11

CTR-ZO-1 Interaction is Required for Metastasis of Orthotopic Xenografts

Figure 6A:
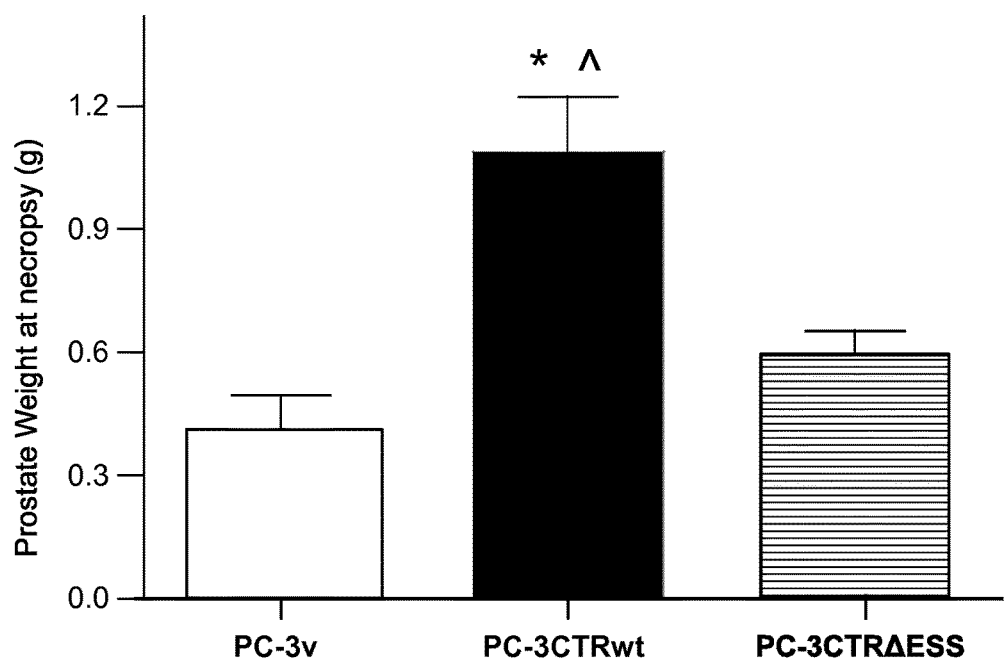
FIG. 6A depicts weights of orthotopic prostate cancer tumors formed by PC-3v, PC-3-CTRwt and PC-3-CTRΔESS cells in nude mice. Red Fluorescence Protein (RFP)-expressing PC-3 cells were transfected either with vector (V), CTR-wt or CTR-ΔESS constructs. The cells (1×10$^6$) were orthotopically implanted into the prostate of nude mice. Animals were sacrificed 8 weeks after implantation, and prostate tumors were weighed.
Figure 6B:
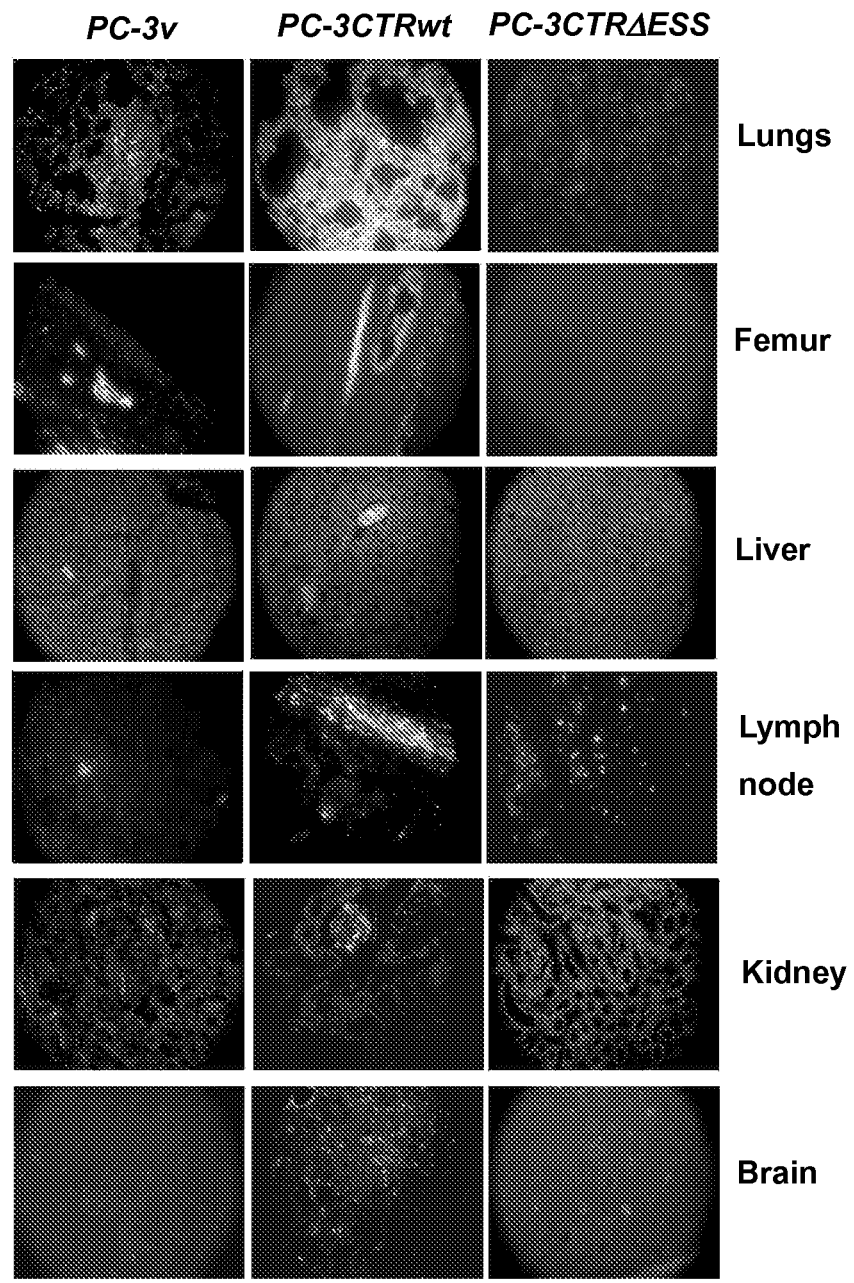
FIG. 6B depicts micrographs of distant metastases formed by PC-3v, PC-3 CTRwt and PC-3 CTRΔESS cells in nude mice. Red Fluorescence Protein (RFP)-expressing PC-3 cells were transfected either with vector (V), CTR-wt or CTR-ΔESS constructs. The cells (1×10$^6$) were orthotopically implanted into the prostate of nude mice. Animals were sacrificed 8 weeks after implantation. The indicated organs were removed from mice and observed directly under fluorescent microscope at 100× magnification (*p<0.01 (PC-3v vs PC-3CTRwt); ^p<0.01 (PC3CTRΔESS vs PC-3CTRwt); One-way ANOVA and Newman-keuls test).

The role of CTR-C PDZ-binding motif on tumor metastasis of PC-3 cells was examined in the orthotopic nu/nu (nude) mouse model. FIGS. 6A and 6B are from mice with orthotopic prostate cancer tumors formed by PC-3v, PC-3-CTRwt and PC-3-CTRΔESS cells. Red Fluorescence Protein (RFP)-expressing PC-3 cells were transfected either with vector (V), CTR-wt or CTR-ΔESS constructs. The cells ($1\times10^6$) were orthotopically implanted into the prostate of nude mice. Animals were sacrificed 8 weeks after implantation, and prostate tumors were weighed. The results are shown in FIG. 6A.

FIG. 6B depicts micrographs of distant metastases in tissues of the mice described above. The indicated organs were removed from mice and observed directly under fluorescent microscope at 100× magnification (*$p<0.01$ (PC-3v vs PC-3CTRwt); ^$p<0.01$ (PC3CTRΔESS vs PC-3CTRwt); One-way ANOVA and Newman-keuls test).

Figure 11:
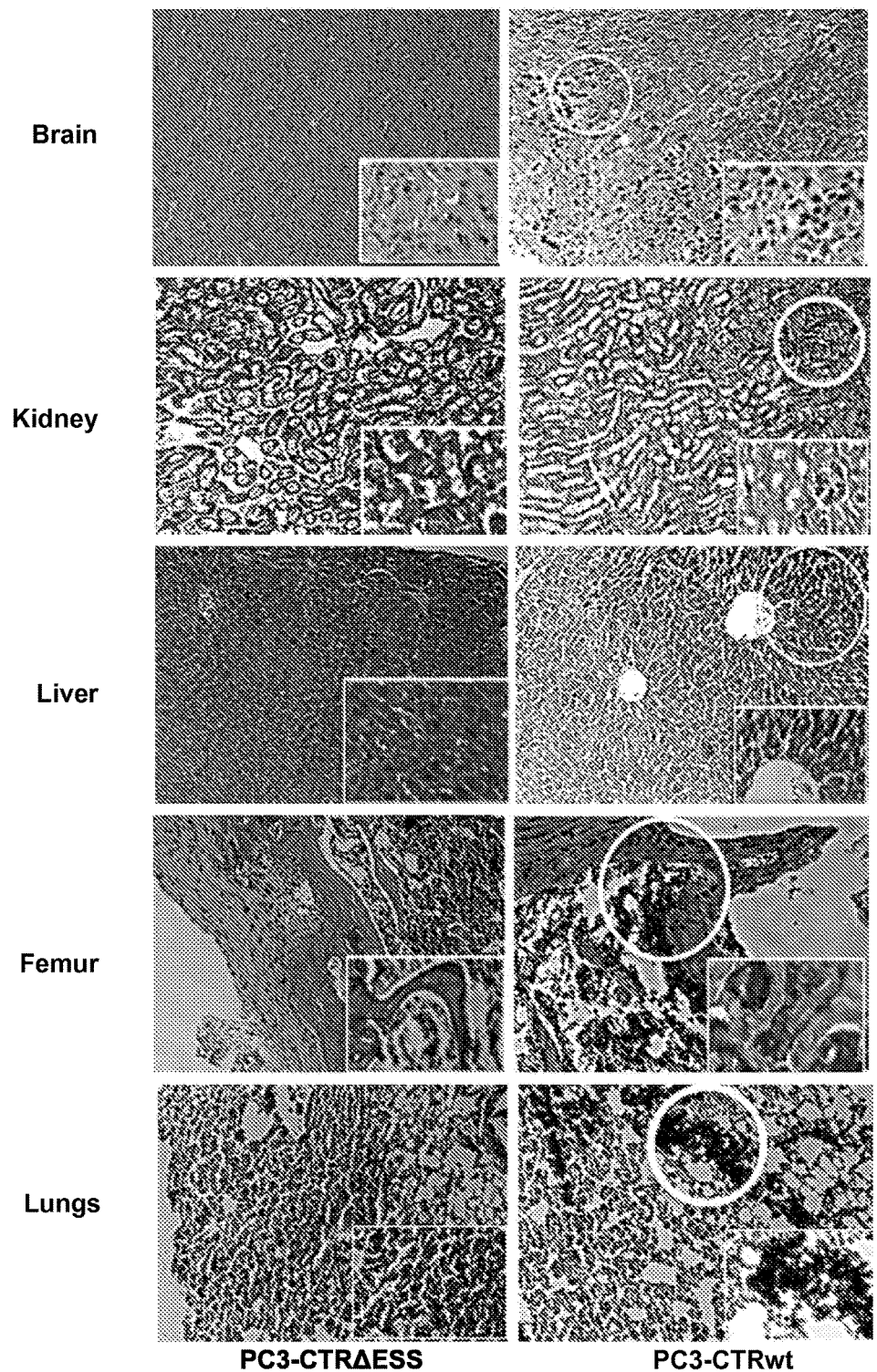
FIG. 11 depicts micrographs after staining with H&E at 100× of distant metastases from brain, liver, kidney, femur, and lungs of mice injected with either PC-3 CTRΔESS and PC-3 CTRwt. The lower right corner box is an enlarged (400×) micrograph of the tumor cells in the circle area.

As expected PC-3 cell line, which lacks CTR, displayed moderate orthotopic growth and metastasis in some organs (FIGS. 6A, 6B, Table 2). PC-3-CTRwt cells formed significantly larger orthotopic tumors and micrometastases in multiple organs including lymph nodes, femur and lungs. In contrast, PC-3-CTRΔESS orthotopic tumors were comparable to those of PC-3V, and no micrometastases were observed in all tested organs, except two out of six mice showed minor lymph node involvement (Table 2). H&E sections of these tumors in distant organs are presented in FIG. 11, with the insert in the lower right corner a higher magnification (400×) of tumor cells from the circled area in the PC-3-CTRwt mice.

TABLE 2

| A. Micrometastases of PC-3 cells in host organs | | | |
|---|---|---|---|
| Organs | PC-3v | PC-3CTRwt | PC-3CTRΔESS |
| Seminal vesicles | ++ | +++ | − |
| Testes | ++ | +++ | − |
| Lymph nodes | ++ | ++ | + |
| Femur | + | +++ | − |
| Lungs | + | ++ | − |
| Liver | + | ++ | − |
| Mesentery | + | ++ | − |
| Kidneys | + | ++ | − |
| Brain | − | − | − |

| B. Frequency of micromestases in host organs | | | |
|---|---|---|---|
| Organs | PC-3v | PC-3CTRwt | PC-3CTRΔESS | Number of 6animals (n) |
| Seminal vesicles | 5 | 6 | 0 | 6 |
| Testes | 3 | 6 | 0 | 6 |
| Lymph nodes | 6 | 6 | 2 | 6 |
| Femur | 2 | 4 | 0 | 6 |
| Lungs | 1 | 3 | 0 | 6 |

TABLE 2-continued

| Liver | 2 | 2 | 0 | 6 |
| Mesentery | 1 | 1 | 0 | 6 |
| Kidneys | 1 | 2 | 0 | 6 |
| Brain | 0 | 0 | 0 | 6 |

Example 12

Figure 12A:
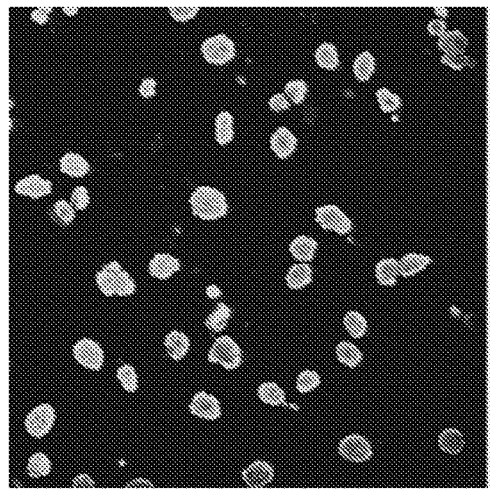
FIG. 12A depicts the results from PC-3 cells of negative controls for in situ PLA assay performed as described in FIG. 7D, but where either or both primary antibodies (anti-CTR and anti-ZO-1) were substituted with isotypic antibody controls. No interaction signal was detected.
Figure 12B:
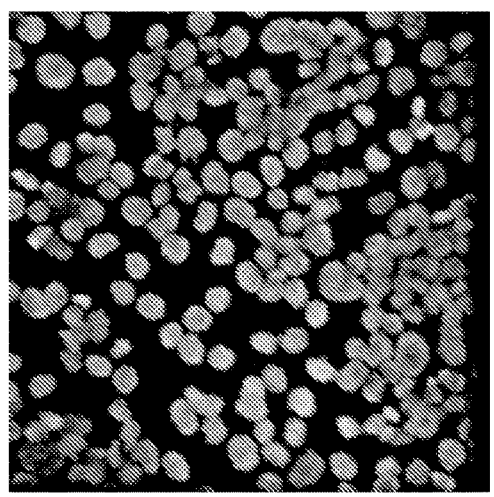
FIG. 12B depicts the results from PC-3 cells of an in situ PLA assay performed with goat anti-CTR serum and positive isotypic control instead of anti-ZO-1 antibody. No interaction signal was detected.
Figure 12C:
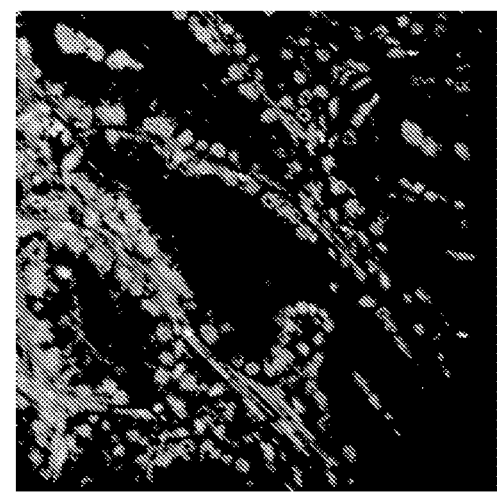
FIG. 12C depicts the results of an in situ PLA assay in prostate cancer tissue specimens, in which primary antisera were substituted with isotypic controls. No signal was detected.
Figure 13:
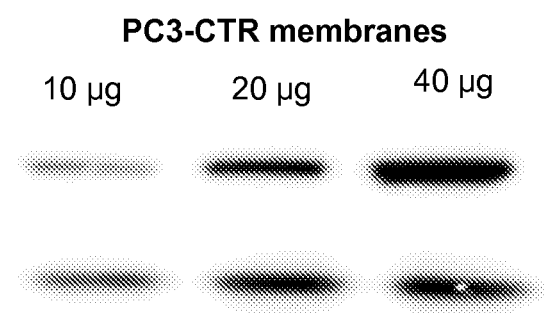
FIG. 13 shows that anti-CTR antibody reliably detects CTR immunoreactivity in PC-3CTRwt membranes. The membranes were loaded on the gel in increasing concentrations (10-40 μl), were transferred on to nitocellulose membrane, and CTR immunoreactivity was detected by Western blotting. The results depict dose-dependent increase in CTR immunoreactivity with increase in membrane concentrations.

CTR-ZO-1 Interaction is Observed in PC Cell Lines and Tumor Specimens:

CTR-ZO-1 interaction in unmodified cells or tissues was examined by an in situ proximity ligation assay (PLA assay). To test specificity of the assay, either rabbit anti-ZO-1 (FIG. 12B) or both goat anti-CTR and anti-ZO-1 (FIG. 12A) were replaced with isotypic control sera. No interaction signal (red dot) was detected either in PC-3CTRwt cells (FIGS. 12A and 12B) or prostate cancer tissue (FIG. 12C).

Figure 7D:
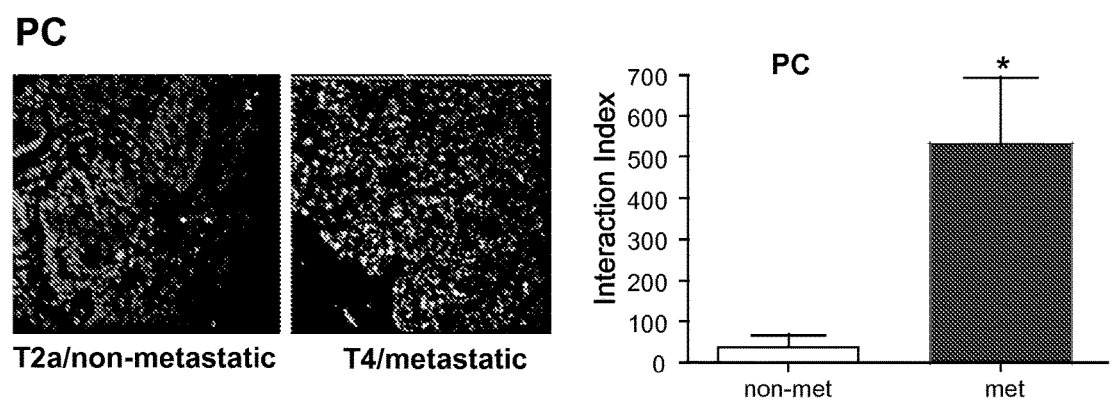
FIG. 7D shows representative micrographs of CTR-ZO-1 interactions in PC specimens of metastatic and non-metastatic tumors treated as described in FIG. 7A. The graph presents quantitative data (mean±SEM; n=3 of each condition; * p<0.001, paired t-test).

Next, CTR-ZO-1 interaction was examined in PC-3CTRwt cells. FIG. 7A shows representative micrographs of CTR-ZO-1 interactions in PC-3 CTRwt cells in the absence and presence of CT stimulation for 30 sec. Each dot represents an interaction between activated CTR and ZO-1, detected by in situ PLA™ using the Duolink® kit. Nuclei were stained with DAPI. The graph presents quantitative data of CTR-ZO-1 interactions in three separate but identical experiments (mean±SEM; n=6, p<0.001, paired t-test). Some CTR-ZO-1 interactions were observed in the absence of exogenous CT stimulus, possibly due to activation of CTR by endogenous CT secretion (Karpova et al., 2006). However, stimulation with 50 nM CT led to eighty-fold increase in these interactions in 30 seconds, and every cell responded to CT stimulation (FIG. 7A). In a comparable experiment using PC-3CTRΔESS cells, no CTR-ZO-1 interactions were observed with or without CT (FIG. 7B). Next, this phenomenon was examined in LNCaP cells, which are androgen-responsive and endogenously express CTR but not CT (Karpova et al., 2006). Unstimulated LNCaP cells did not display any CTR-ZO-1 interaction. When stimulated with CT (50 nM, 30 seconds), all cells responded with strong interaction between endogenous CTR and ZO-1 (FIG. 7C). Finally, non-metastatic and metastatic PC specimens were examined in a similar experiment. CTR-ZO-1 interactions were observed in PC specimens, and the number of interactions in metastatic PC (tumor stage T4) was thirteen-fold greater than non-metastatic PC (tumor stage T2a) (FIG. 7D).

Figure 7E:
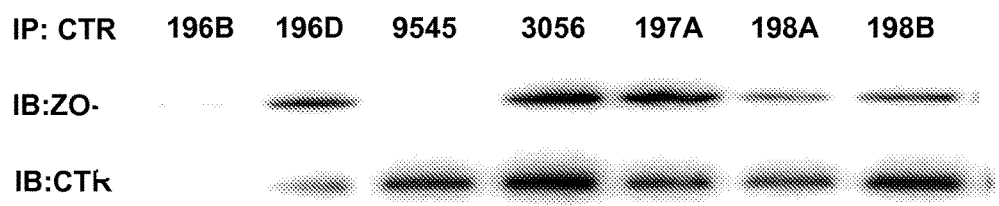
FIG. 7E shows ZO-1 immunoblots from tumors that were paraffin-embedded, deparaffinized, and homogenized. The clarified supernatant was used for immunoprecipitation of CTR. CTR immunoprecipitates were fractionated on SDS-PAGE, and ZO-1 was detected by immunoblotting and the blots were normalized by immunoprecipitation antibody.
Figure 14A:
FIGS. 14A and 14B show the presence of CTR-ZO-1 interaction in natural tumors. Prostate Cancer specimens from patients were collected, homogenized and immunoprecipitation of either ZO-1 (FIG. 14A) or CTR (FIG. 14B) was performed. The immunoprecipitates were then fractionated on SDS-PAGE and transferred on nitrocellulose membrane. The blots were then probed for co-precipitation of CTR (FIG. 14A) or ZO-1 (FIG. 14B). The blots were then normalized for loading controls by precipitating antibodies.
Figure 14B:
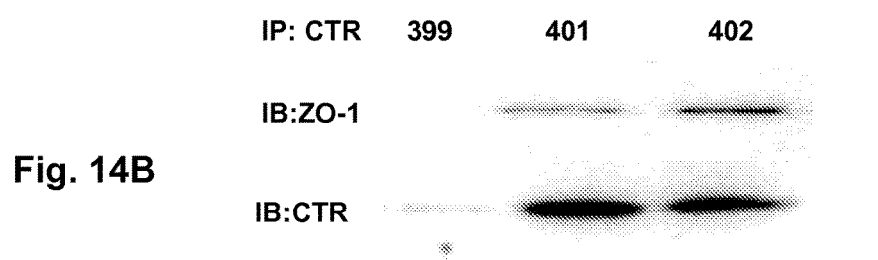

To biochemically validate the results of FIG. 7D, CTR was immunoprecipitated from lysates of randomly selected prostate tumors followed, and the IPs were tested for the presence of ZO-1 by Western blotting. As depicted in FIG. 7E, CTR from five of six tumor specimens co-precipitated significant amounts of ZO-1. Additionally, CTR was co-IPed by ZO-1, and in reverse, ZO-1 was co-IPed by CTR in three prostate tumors (FIG. 14, left and right, respectively) These results support the data of FIG. 7D, and provide biochemical evidence for the occurrence of CTR-ZO-1 association in natural prostate tumors.

Example 13

CT-CTR Expression is Elevated in Metastatic Prostate Cancer.

Figure 7F:
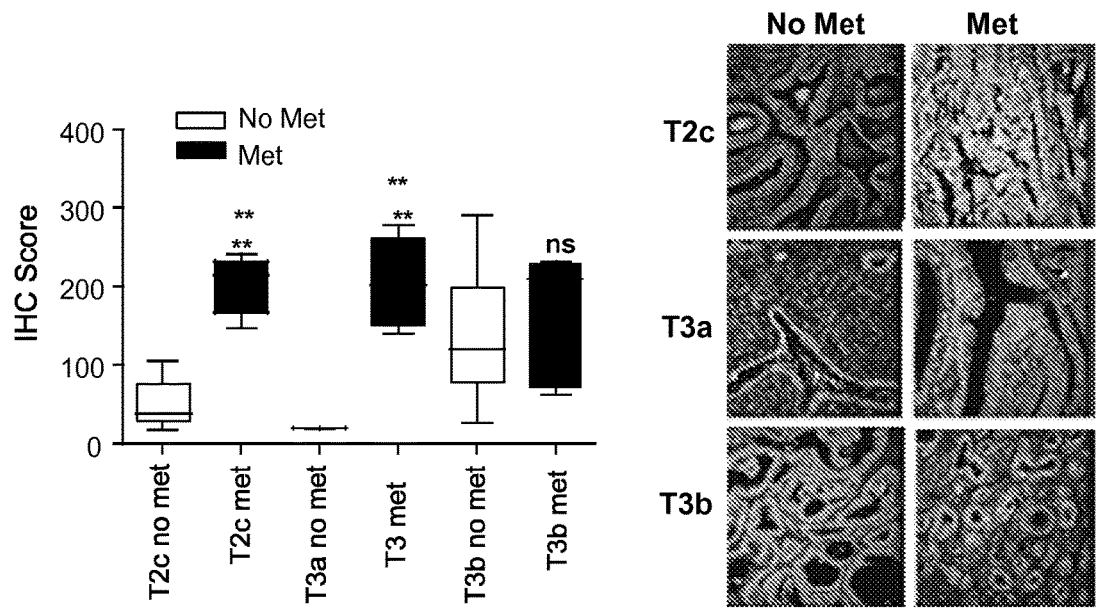
FIG. 7F depicts CT and CTR expression in non-metastatic (No-met) versus metastatic (Met) cases of prostate cancer cells, shown as a box-and-whisker plot of CT immunohistochemistry (IHC) scores from a cohort of 48 patients with non-metastatic and metastatic prostate cancer of tumor stages T2c-T3b TMA (USBiomax product#PR955). Immunopositive cell populations were scored as follows: >75% immunopositive cells=4, >50%=3, >25%=2, <25%=1, negative as 0. Staining intensity was scored as: weak=1; moderate=2; and strong=3. IHC score was immunopositive cells score*staining intensity score; (**p<0.01; *p<0.02, two-tailed t test).

To examine clinical significance of CT-CTR axis in prostate cancer metastasis, the distribution of CT/CTR immunoreactive cell populations was examined in a tissue microarray of 48 cohorts of known clinical outcomes (n=35 non-metastatic and 13 metastatic, US Biomax PR955). CT- and CTR-immunopositive cells in each specimen were counted and scored. FIG. 7F depicts CT and CTR expression in non-metastatic (No-met) versus metastatic (Met) cases of prostate cancer cells. The box-and-whisker plot of CT immunohistochemistry (IHC) scores from a cohort of 48 patients with non-metastatic and metastatic prostate cancer of tumor stages T2c-T3b TMA (USBiomax product#PR955). Immunopositive cell populations were scored as follows: >75% immunopositive cells=4, >50%=3, >25%=2, <25%=1, negative as 0. Staining intensity was scored as: weak=1; moderate=2; and strong=3. IHC score was immunopositive cells score*staining intensity score; (**p<0.01; *p<0.02, two-tailed t test).

Figure 7G:
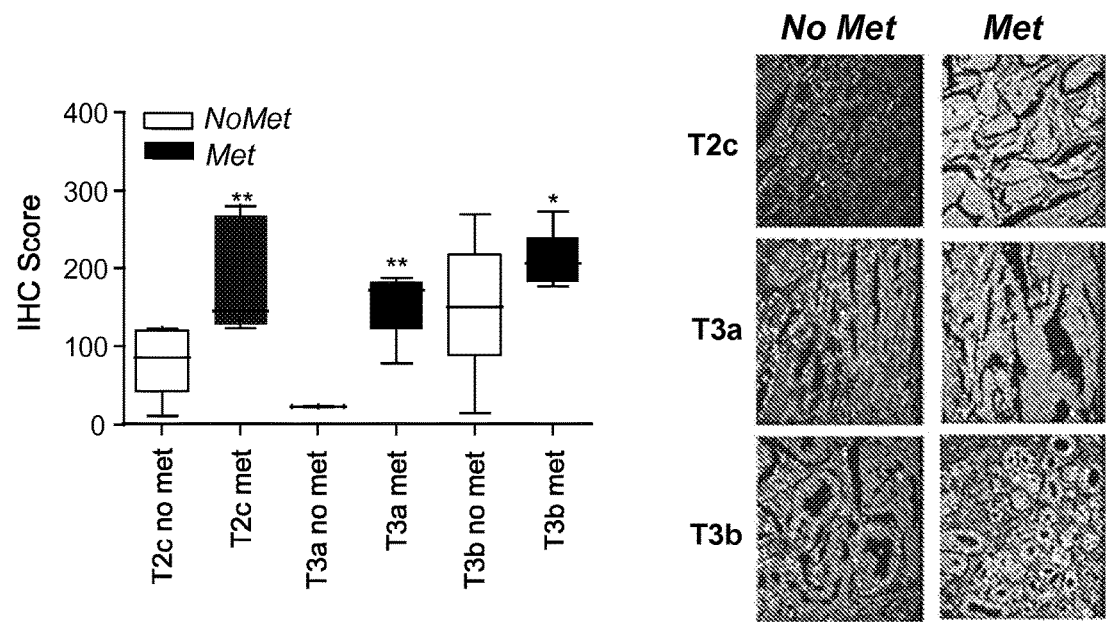
FIG. 7G shows a box-and-whisker plot depicting CTR expression as a plot of CTR IHC scores from same cohort as described in FIG. 7F.

FIG. 7F shows a box-and-whisker plot demonstrating the change in CT expression in prostate cancer specimens from patients with different stages of cancer. Similarly, the change in CTR expression in the same cohort is presented in FIG. 7G. Stratification of the data on the basis of tumor stage and metastasis (TNM classification) revealed that IHC score of CT and CTR in metastatic specimens was significantly higher than non-metastatic PC specimens of same T stage, specifically in T2c and T3a stages.

The above examples 2-13 demonstrate that the activation of the CT-CTR autocrine axis increases invasiveness and metastatic potential of prostate cancer cells lines. The results also indicate the importance of tight junctions in metastasis, with an increase in TJ disruption associated with invasive phenotype. CTR was also shown to interact with ZO-1 through its PDZ-binding motif, and this interaction is critical for the destabilization of TJs and for distant metasis. The site of the CTR-ZO-1 interaction was identified above as ZO-1-PDZ3.

Example 14

CTR Induces TJ Protein Disassembly.

The above examples demonstrated that calcitonin (CT) affected TJ functionality as assessed by TER and PCP in multiple prostate cell lines including LNCaP, DU-154 and PC-3M cells. The effect of CT on TJ functionality was tested by monitoring TER of PC-3CTRwt monolayers. FIG. 15A shows the effect of CT on TJ stability as measured with transelectric epithelial resistance (TER) and paracellular permeability (PCP) of PC3-CTRwt cells treated with/without CT. The left graph shows TER of PC3-CTRwt cells, with and without CT, over five hours. Polarized PC-3-CTRwt cells were serum-starved for 4 hours, then treated with or without 50 nM CT. TER was measured with EVOM volt-ohm meter. The results are expressed as TER ±SEM ($\Omega cm^2$±SEM; n=6). The right graph shows PCP of PC3-CTRwt cells with and without CT. PCP was determined by diffusion of ~4 kDa TRITC-conjugated dextran from the upper to the lower chamber in one hour. The results are expressed as µg/ml/hour of TRITC-Dextran diffused ±SEM (n=6; *p<0.05 (−CT v +CT, One way ANOVA and Newman-Keul's test)).

Figure 15B:
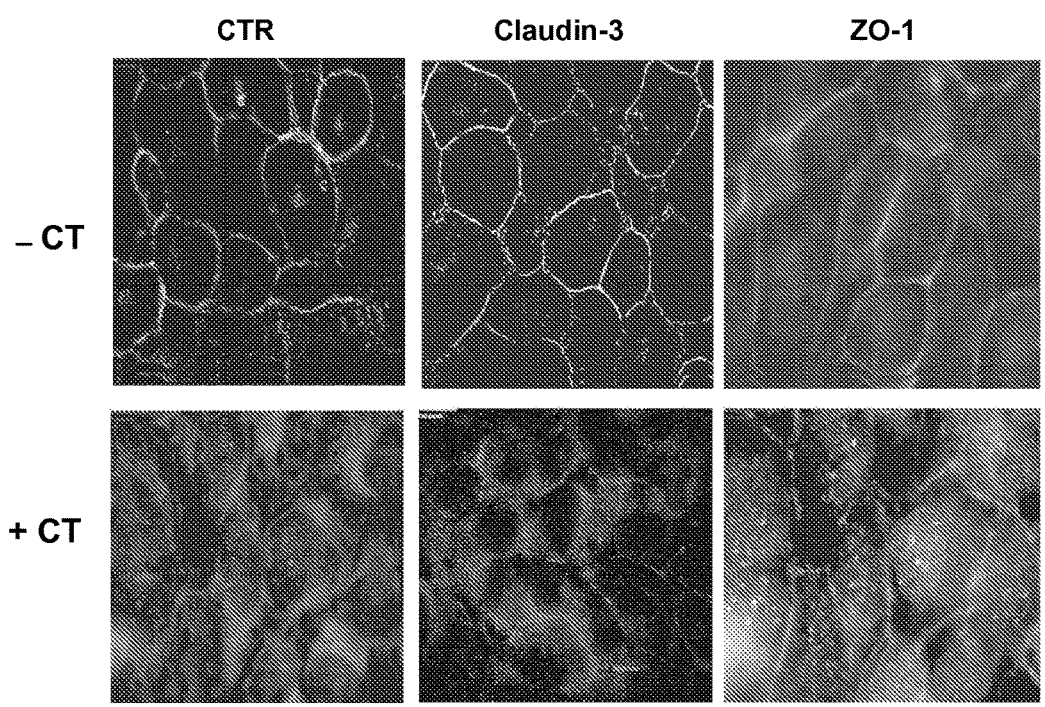
FIG. 15B. depicts immunochytochemical analysis for several cell proteins of PC3-CTRwt cells with and without CT. Polarized PC-3CTRwt cells were fixed and stained for FLAG (CTR), claudin-3, and ZO-1 before and after 30 min of CT stimulus (magnification 400×).

As depicted in FIG. 15A, PC-3CTRwt cells showed TER of approximately 650 $\Omega$-$cm^2$. Treatment with 50 nM CT led to relatively rapid decline in TER, and a remarkable drop was observed within 30 min of CT stimulus (FIG. 15A, left graph). In contrast, CT increased the PCP by eighty percent (FIG. 15A, right graph). To test whether CT-mediated loss of TJ functionality is caused by disassembly of TJs, subcellular distribution of key TJ proteins was examined. Polarized PC-3CTRwt cells were treated with 50 nM CT for 30 min, and then processed for immunofluorescence with anti- FLAG (CTR), anti-ZO-1 and anti-claudin-3 antibodies. The results of FIG. 15B show that CTR, ZO-1 and claudin-3 were preferentially located at cell-cell contacts of untreated PC-3CTRwt cells. However, the treatment with CT led to the loss of these proteins at cell-cell contacts and their internalization within 30 min of CT stimulus.

Figure 15C:
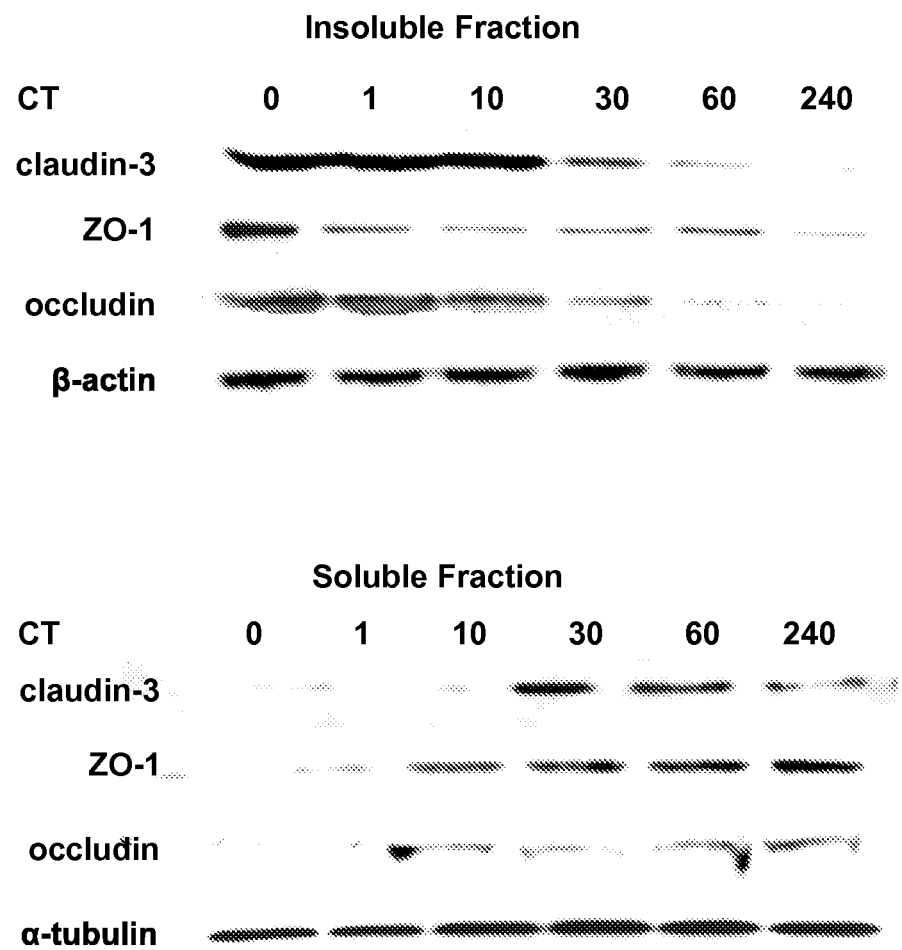
FIG. 15C shows the subcellular distribution of TJ proteins as a function of time through representative immunoblots of claudin 3, ZO-1 and occludin of insoluble and soluble fractions in TX-100 of cells that were treated with CT (50 nM) for 0, 1, 10, 30, 60, and 240 min. β-actin was used for control.

It is known that junctional proteins are functional only when they are at cell-cell contacts on the membrane (Shin et al., 2006). Therefore, the subcellular distribution of TJ proteins was analyzed by immunoblotting TX-soluble (cytoplasmic) and TX-insoluble (membrane) fractions of cell lysates. As depicted in FIG. 15C, CT treatment of PC-3CTR cells led to significant but rapid translocation of ZO-1, claudin-3 as well as occludin from the insoluble (the left side) to the soluble fraction (the right side). The endocytosis of TJ proteins was rapid, and increased progressively throughout the experimental period of four hours. Specifically, translocation of ZO-1 from the insoluble to the soluble compartment was quicker and observed within 1 min of CT stimulus. Similar translocation of occludin was observed after ten min, and that of claudin-3 after 30 min of CT stimulus.

Figure 15D:
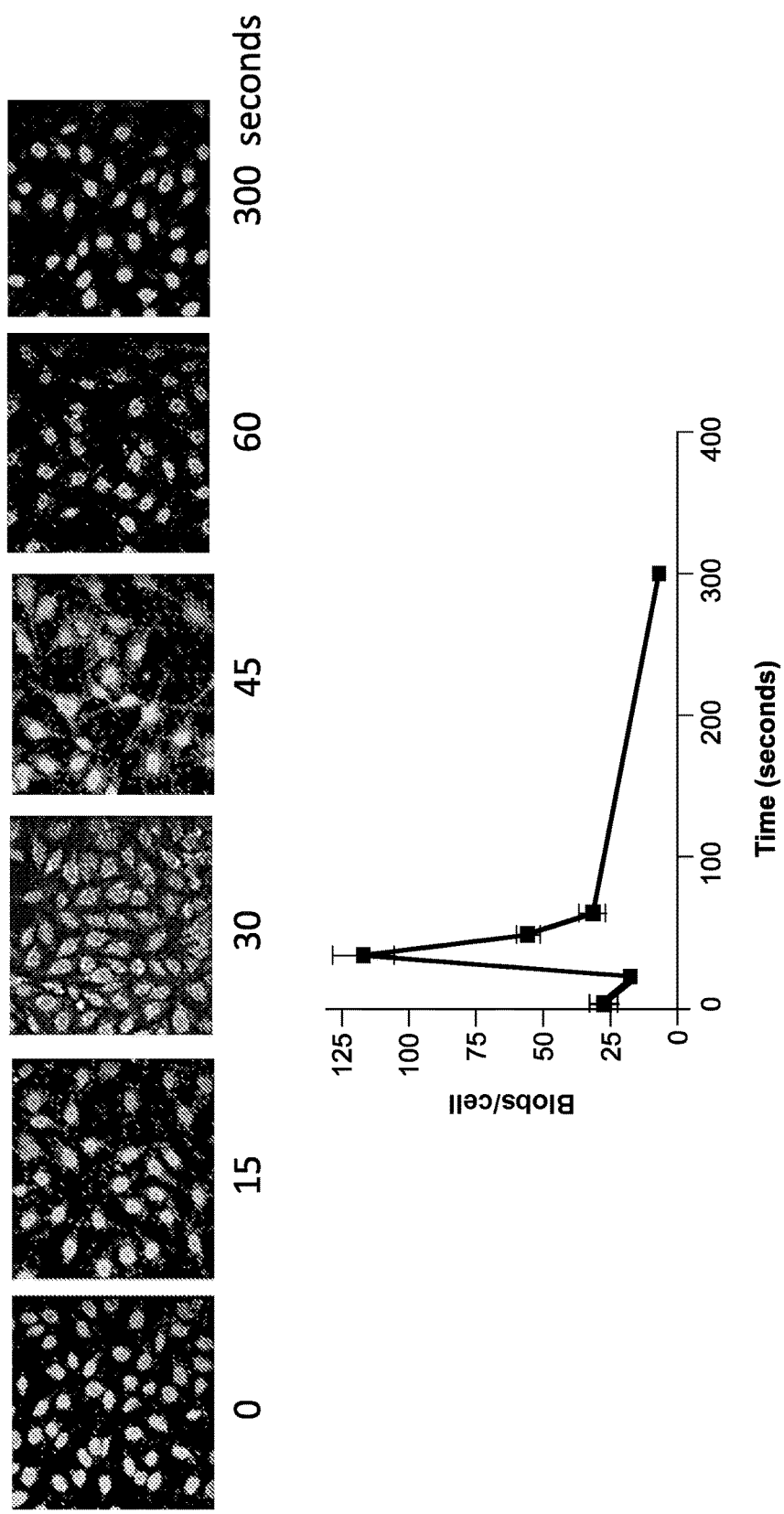
FIG. 15D shows the time course of CTR-ZO-1 interaction through representative micrographs and a line graph. Representative micrographs are shown of CTR-ZO-1 interactions in PC-3CTRwt cells at various time periods (0-300 seconds) after CT stimulus. Each highlighted dot represents an interaction between activated CTR and ZO-1, detected by in situ PLA™ using the Duolink® kit. Nuclei are stained with DAPI. The line graph presents the mean±SEM of dots at each time point (n=6).

Since CTR directly interacts with ZO-1 through PDZ domain, whether CT-induced endocytosis of ZO-1 is caused by CTR-mediated events prior to or subsequent to CTR-ZO-1 interaction was tested. To determine the time course of CTR-ZO-1 interaction, in situ PLA assay was used (FIG. 15D). FIG. 15D shows the time course of CTR-ZO-1 interaction through representative micrographs and a line graph. Representative micrographs are shown of CTR-ZO-1 interactions in PC-3CTRwt cells at various time periods (0-300 seconds) after CT stimulus. Each highlighted dot represents an interaction between activated CTR and ZO-1, detected by in situ PLA™ using the Duolink® kit. Nuclei were stained with DAPI. The line graph presents the mean±SEM of dots at each time point (n=6). The results indicate that CTR-ZO-1 interaction occurred within seconds, peaked at 30 seconds and then rapidly declined to prestimulus levels. Considering that ZO-1 endocytosis was observed after 1 minute of CT stimulus, it is conceivable that CTR-mediated events subsequent to CTR-ZO-1 interaction may be associated with TJ protein endocytosis.

Together, these results indicate that the treatment of PC-3CTRwt cells with CT leads to rapid disassembly of TJs, and endocytosis of major ZO-1, occluding and claudin 3. These results are corroborated by TJ functionality assays demonstrating remarkable changes in TER and PCP in response to CT treatment. Since CTR-stimulated endocytosis of ZO-1 occurred earlier than other TJ proteins, subsequent experiments focused on the action of CTR on ZO-1 modification and internalization.

Example 15

CTR-Stimulated TJ Disassembly is PKA-Dependent.

To test whether specific PKA inhibitors abrogate CT-induced TJ disassembly, two specific, well-characterized PKA inhibitors, mPKI and H-89, were used. PC-3CTRwt cells were treated with CT (50 nM for 30 min) in the presence of mPKI (100 nM) or H-89 (10 µM). Either of these inhibitors was added 15 min prior to the addition of CT. Initial studies tested multiple concentrations of these inhibitors, and observed that 100 nM of mPKI and 10 µM of H-89 completely abolished CT-stimulated PKA activity. These concentrations are significantly lower than those used by other investigators for the same purpose. Immunocytochemical studies of PC-3CTRwt cells revealed that ZO-1 was localized to cell-cell contact in unstimulated cells, and CT stimulated endocytosis of ZO-1. mPKI did not have any effect on the localization of ZO-1 at cell-cell contacts. However, when added in combination with CT, mPKI completely abrogated CT-induced ZO-1 endocytosis (FIG. 16A). FIG. 16A depicts photo micrographs of PC3-CTRwt cells, CT-stimulated in the presence and absence of mPKI. Polarized PC-3CTRwt cells were fixed and stained for FLAG (CTR), claudin 3 and ZO-1 before and after 30 min of CT stimulus in the presence/absence of mPKI (10 nM) (magnification 400×).

These results were corroborated by the subcellular distribution of TJ proteins in TX-insoluble and TX-soluble fractions. FIG. 16B shows representative immunoblots of claudin 3, ZO-1 and occludin of insoluble and soluble fractions in TX-100 of cells that were treated with/without CT (50 nM) for various time periods in the presence or absence of mPKI (10 nM). β-actin was used for control. FIG. 16C shows similar immunoblots but in the presence or absence of H89 (10 µM), instead of mPKI. As depicted in FIGS. 16B and 16C, mPKI as well as H-89 prevented CT-stimulated translocation of TJ proteins from TX-insoluble to TX-soluble fractions.

Example 16

CTR Increases Serine/Threonine Phosphorylation of TJ Proteins.

To directly examine the involvement of PKA in CTR action on TJ disassembly, the in vivo incorporation of $^{32}$PO4 in TJ proteins was examined. FIG. 17A shows autoradiograms of $^{32}$P-labeled cell lysates and immunoblots of ZO-1 and claudin 3 from PC-31 CTR treated with/without CT in the presence/absence of mPKI. Arrows indicate location of ZO-1 and claudin-3. FIG. 17B depicts the total amount of $^{32}$P-radioactivity of IP bands of ZO-1 and claudin from cells treated with CT (CT) and without treatment (Control, C). The results in FIG. 17A show that CT stimulus caused a remarkable increase in the incorporation of $^{32}$PO$_4$ in ZO-1 and claudin 3. The results of occludin were inconclusive (data not shown). Subsequent immunoprecipitation of $^{32}$P-labeled proteins with antisera to ZO-1 and claudin 3 revealed a ten-fold increase in $^{32}$P incorporation in these two proteins following CT stimulus (FIG. 17B). Moreover, the phoshorylation was completely abolished in the presence of mPKI, suggesting this phosphorylation was specifically catalyzed by PKA (FIG. 17A).

Next, the phosphorylated amino acids in these proteins were identified by probing ZO-1 and claudin 3 immunoprecipitates with antisera against phosphoserine, phosphothreonine and phosphotyrosine. FIG. 17C shows representative immunoblots of ZO-1 and claudin 3 cell lysates treated with (CT) and without CT (C). The blots were probed by antibodies to phosphoserine (Ser), phosphothreonine (Thr), and phosphotyrosine (Tyr). As expected, CT stimulated phosphorylation of serines and threonines in ZO-1 and only threonines in claudin-3 (FIG. 17C). There was complete absence of phosphotyrosines in either of these TJ proteins, consistent with the role of PKA in CTR-stimulated phosphorylation of ZO-1 and claudin 3.

Example 17

CTR-ZO-1-Stimulated Phosphorylation of ZO-1 and a Claudin 3 Requires CTR-ZO-1 Interaction as Well as PKA Activation.

As shown above, the interaction of CTR with ZO-1 occurs between CTR-C PDZ-binding motif and PDZ3 domain of ZO-1. Mutation of CTR-C PDZ-binding motif (CTRΔESS) did not affect CTR-induced PKA activation, but abrogated the actions of CTR on TJ functionality, invasion and distant metastasis. To examine the role of CTR-C PDZ-binding motif on phosphorylation of TJ proteins, the serine/threonine phosphorylation of ZO-1 and claudin 3 was analyzed in PC-3CTRwt and PC-3CTRΔESS cells. FIG. 18A shows serine phosphorylation of ZO-1 and claudin 3 in CT±mPKI-treated cell lysates from PC-3 CTRwt and PC-3 CTRΔESS cells that were immunoprecipitated with antibodies to either ZO-1 or claudin 3. The immunoprecipitates were then probed with antibodies to phosphoserine. FIG. 18B shows threonine phosphorylation of ZO-1 and claudin 3 in CT±mPKI-treated cell lysates from PC-3 CTRwt and PC-3 CTRΔESS cells that were immunoprecipitated with antibodies to either ZO-1 or claudin 3. The immunoprecipitates were then probed with antibodies to phosphothreonine. The IPs of ZO-1 and claudin 3 were immunoblotted and probed for phosphoserine and phosphothreonine.

The results presented in FIGS. 18A and 18B demonstrate that no phosphoserines or phosphothreonines were detected in either ZO-1 or claudin 3 in unstimulated PC-3CTRwt or PC-3CTRΔESS cells. When stimulated with CT for 1 minute, a detectable increase in phosphoserines/phosphothreonines in ZO-1 and phosphothreonine, but not phosphoserines, in claudin 3 was observed. mPKI alone did not have any effect on serine/threonine phosphorylation, but it prevented CTR-induced phosphorylation of ZO-1 and claudin 3. However, activation of CTRΔESS with CT did not induce phosphorylation of ZO-1 and claudin 3 under any conditions. Since CTRΔESS is shown to activate PKA, present results can be explained by CTRΔESS-activated PKA may not phosphorylate claudin 3 and/or ZO-1 because it may not be in the proximity of TJ complex; and that CTR-ZO-1 interaction may be necessary for bringing CTR in TJ complex and to activate the localized PKA in the TJ complex.

Example 18

CTR-ZO-1 Interaction is Required for CTR-Mediated TJ Disassembly.

Based on the results of FIGS. 18A and 18B, it seems that CTR must activate the PKA at a specific location that is in the close proximity of TJ proteins in order to phosphorylate TJ proteins; and this spatial specificity of CTR may be facilitated by the interaction between CTR-C PDZ-binding motif and ZO-1-PDZ3. If this is true, than CTR would not be able to induce TJ disassembly in cells expressing either CTRΔESS or ZO-1ΔPDZ3. This theory was tested by studying subcellular distribution of TJ proteins in TX-soluble/insoluble fractions of cells expressing either CTRΔESS or ZO-1ΔPDZ3 cells. FIG. 19A shows photomicrograhs of PC-3 CTRΔESS cells with and without CT stimulus. Polarized PC-3 CTRΔESS cells were fixed and stained for FLAG (CTR), claudin 3 and ZO-1 before and after 30 min of CT stimulus (magnification 400×). FIG. 19B shows a representative immunoblot of claudin 3, ZO-1 and occludin from insoluble and soluble fractions in TX-100 of PC-3 CTRΔESS cells that were treated with CT (50 nM) for various time periods from 0 to 240 min. FIG. 19C shows a representative immunoblot of claudin 3, ZO-1 and occludin of insoluble and soluble fractions in TX-100 of CTR-ΔPDZ1, CTRΔPDZ2 and CTRΔPDZ3 cells that were treated with and without CT (50 nM).

The results of FIGS. 19A and 19B demonstrate that CT could not induce endocytosis of ZO-1, claudin 3 or occludin in cells expressing CTRΔESS or ZO-1ΔPDZ3. Similarly, ZO-1 in these cells remained at cell-cell contacts, and did not translocate to cytoplasm after CT stimulus (FIG. 19C). Taken together, these results reinforce that CTR-ZO-1 interaction provides spatial specificity to CTR; and this spatial specificity is necessary for the activation of localized PKA in TJ complex.

To understand the significance of CT-induced, PKA-dependent disassembly of TJs in PC cell adhesion and invasion, the action of CT was examined on TER, PCP, cell adhesion and invasion in PC-3CTRwt cells in the presence/absence of mPKI. PC-3CTRwt cells displayed steady TER during experimental period of 60 min (FIG. 20A). However, CT-treated cells showed steady, remarkable decline in TER, which became apparent within 10 min of CT stimulus. However, the presence of mPKI completely abrogated CTR-induced decrease in TER. Similarly, mPKI abrogated the actions of CT on PCP and invasion (FIGS. 20B and 20C respectively). Next, the adhesion of PC-3CTRwt cells was examined on culture dishes. Treatment of PC-3CTRwt cells with 50 nM CT stimulus caused a remarkable decline in the adhesion of the cells to plastic matrix (FIG. 20D). However, the presence of mPKI prevented the loss of adhesion. Taken together, these results demonstrate that CTR induces TJ disassembly by PKA-mediated phosphorylation of ZO-1 and claudin 3, and leads to a remarkable loss of cell adhesion and increase of cell invasion, indicating that the loss of TJs may be a key step in CTR-induced EMT of prostate cancer cells.

Example 19

PKA Activation is not Required for CTR-ZO-1 Interaction.

To examine the possible role of PKA in CTR-ZO-1 interaction, acceptor photobleaching FRET microscopy was used. CTR-ZO-1 interaction in the presence or absence of mPKI was examined using CTR-wt-CFP and ZO-1-YFP as the FRET pair. The results of FIG. 21 suggest that dormant CTR displayed little interaction with ZO-1 as suggested by very low FRET efficiency (2.9±0.6). When stimulated with 50 nM CT, the FRET efficiency increased to 29.7±1.2, suggesting moderately strong interaction between CTR and ZO-1. mPKI did not significantly alter FRET efficiency of either dormant CTR (1.2±0.6) or activated CTR (24.2±3.5). CTR-ZO-1 interaction was also examined in response to PKA activation by forskolin (Data not shown). CTR-ZO-1 FRET efficiency remained at 2.2±0.1 either in the absence or presence of forskolin, suggesting PKA activation is not required for CTR-ZO-1 interaction, and its activation does not affect CTR-ZO-1 interaction. When taken together with other results, these results indicate that CTR-ZO-1 interaction may occur prior to the activation of localized PKA in TJ complex, and support that CTR-ZO-1 interaction enables CTR to activate localized PKA in the TJ complex.

Example 20

Interference of CTR-ZO-1 Interaction can be Used to Attenuate Proinvasive Actions of CT on Prostate Cancer Cells.

As shown above, CTR binds to ZO-1 through PDZ interaction (i.e. PDZ ligand on C-tail of CTR binds to the PDZ domain of ZO-1). To attenuate this binding, ZO-1 was saturated with a small C-terminal peptide of CTR sequence containing the PDZ-binding motif. Since ZO-1 is an intracellular membrane protein, the interfering peptide was delivered inside the plasma membrane. It has been shown that trans-activating transcriptional activator (TAT) protein (86-mer polypeptide) from HIV-1 enters mammalian cells when added to the surrounding media (Frankel et al., 1988; Green et al., 1989). Certain small regions of such proteins (10-16-mers) called protein transduction domains (PTDs), also efficiently traverse biological membranes (Elliott et al., 1997). Therefore, a fusion peptide Pep 1 was synthesized of TAT-peptide sequences of HIV virus and CTR-C(N-EQESSAAYGRKKRRQRRR-C (SEQ ID NO:2), CTR-C sequence underlined). The first experiment was to see if Pep I binds to ZO-1 in reversible fashion. For this, amino acid Y in Pep I was labeled with $^{125}$I, and the binding with ZO-1 analyzed in the presence/absence of unlabeled Pep I (1000×; 20 μM). PC-3CTR-ZO-1-MYC cells were first incubated with unlabeled Pep I or control peptide (20 μM) for 5 min. The cells were then incubated with $^{125}$I-pep I or C for 25 min. The cells were then washed in IP buffer, treated with DSP, and lysed. ZO-1 IPs were obtained, fractionated on SDS-PAGE, and autoradiographed. The results of FIG. 22A show that Pep I was bound to ZO-1, and the binding was almost abolished in the presence of unlabeled Pep I. C peptide did not co-IP with ZO-1 demonstrating the specificity PepI-ZO-1 binding. Next, whether Pep I competes with CTR for ZO-1 binding was tested. For this, PC-3-CTR-wt cells were treated with CT (50 nM) and or Pep I (50 μM) for 15 min. The CTR IPs were then immunoblotted and probed for ZO-1 immunoreactivity. The results of FIG. 22B show that the co-precipitation of ZO-1 with CTR increased following CTR activation (as reported earlier), and preincubation with Pep I markedly diminished CTR-ZO-1 co-precipitation in both cases (with or without CT). Next, the biological impact of this phenomenon was examined by testing the effect of Pep I on CTR-stimulated invasion. The results of FIG. 22C show that neither the control peptide nor Pep I (50 μM) significantly affected basal invasion of PC-3-CTR-wt cells. However, Pep I significantly attenuated CT (50 nM)-induced invasion. These results demonstrate that interference in CTR-ZO-1 interaction by a synthetic peptide like PepI can be a viable therapeutic approach for attenuating CTR-mediated prostate cancer progression.

Example 21

Peptide Molecules that Disrupt ZO-1-CTR or Other Invasion-Inducing Receptor Interaction as Therapeutic Agents to Treat Metastasis.

The binding of ZO-1 and CTR can be attenuated by saturating ZO-1 with a small C-terminal peptide of CTR sequence containing the PDZ ligand. Since ZO-1 is an intracellular membrane protein, the interfering peptide must penetrate plasma membrane to interact with ZO-1. As discussed above, fusion peptides of small TAT peptides (12-mer) and six (Pep I) or eight amino acids (Pep II) of C-terminal of CTR were synthesized. Control peptides were TAT peptides (12-mer) containing random amino acid sequence of equivalent size (6-mer). The initial experiment indicated that the preincubation of these peptides attenuated CT-induced invasion of PC-3-CTR-wt cells. The results of FIG. 23 show that either control peptide, PepI (50 μM) or PepII (50 μM) did not significantly affect basal invasion of PC-3-CTR-wt cells. However, both peptides (Pep I and Pep II) significantly attenuated CT (50 nM)-induced increase in the invasion of PC-3-CTR-wt cells, but Pep I was the more potent antagonist (FIG. 23). Thus, these two peptides (sequences given below) could be used therapeutically to attenuate or inhibit metastasis in cancerous cells.

The sequences of peptides 1 and II are as follows:

```
                                        (SEQ ID NO: 2)
PepI:  N-EQESSAAYGRKKRRQRRR-C (SEQ ID NO: 3)
PepII: N-IIEQESSAYGRKKRRQRRR-C
```

The sequences of peptides 1 and II are shown above. These peptides can be administered to a cancer patient in a number of ways well known in the art. For example, a series of small protein domains, termed protein transduction domains (PTDs), have been shown to cross biological membranes efficiently and independently of transporters or specific receptors, and to promote the delivery of peptides and proteins into cells. TAT protein from human immunodeficiency virus (HIV-1) is able to deliver biologically active proteins in vivo and has been shown to be of considerable interest for protein therapeutics (De Florai et al. 2001; Reuther, et al. 2006; see also, U.S. Pat. No. 7,521,415). Since the PTD sequence was incorporated into the sequence of PepI and PepII, either of the peptides can be injected intratumorally to prevent CTR-ZO-1 interaction in cancer cells. When delivered in the tumor, the peptide (I or II) is able to cross the membrane barrier and attenuate CTR-ZO-1 interaction as demonstrated in FIG. 23. To administer the peptides systemically, one could nano carriers or nano particles to transport them to the tumor (see, for example, U.S. Published Patent Applications 2009/0169478 and 2008/0213377). Other systems for this purpose have been well-described (Hatakeyama et al. 2007; Wang et al. 2007; Demirgoz et al. 2008; Kim et al. 2008; Pan et al. 2011). The delivery of these peptides can be selectively targeted for tumors when the nano particles are covalently linked with receptor-targeted motifs on their outer surface (Zhang et al. 2001; and U.S. Published Patent Applications 2009/0169478 and 2008/0213377), for example, use of prostate-specific membrane antigen (PSMA) to target prostate cancer cells.

Example 22

Small Molecule Inhibitors of ZO-1-CTR Interaction.

The yeast 2-hybrid (Y2H) complementation screening assay and the GST-pulldown assay described above proved a good system to screen for small molecules that can disrupt the interaction between ZO-1 PDZ motif and CTR (or similar receptors capable of destabilizing TJs by binding to ZO-1). The small molecule compounds can be obtained through standard combinatorial chemistry techniques, or from a large library of compounds or by in-silico modeling based on the predicted structure provided in this invention. The binding and ability to inhibit ZO-1-CTR binding can be performed by further modification to the active hits through further rounds of combinatorial chemistry/screening techniques or by empirical in-silico modeling to derive more potent drug molecules.

Y2H complementation screening used as bait the 64 aa long CTR C-tail of hCTR2 fused with the Gal-4 DNA binding domain. After screening 1×10$^6$ transformants, 11 interacting clones were identified, purified and sequenced (Table 1, above). Most positive clones encoded plasma membrane proteins and/or proteins associated with the adenylyl cyclase system. One clone encoded tight junction protein TJP-1 or ZO-1, and this clone also provided the strongest signal in secondary screening. Since CTR destabilized TJs only in the presence of PDZ-binding motif, CTR-ZO-1 interaction was further characterized.

GST pull-down assay: CTR-C tail-ZO-1 interaction was examined using GST pulldown assays. GST-C (random sequence of equivalent length to CTR-Cwt), GST-CTR-Cwt and GST-CTR-CΔESS fusion proteins immobilized on glu-thatione-Sepharose 4B beads were incubated with PC-3 cell lysates. Bound proteins were analyzed for ZO-1 immuno-reactivity by Western (Shah, 2003) blotting. Only GST-fused CTR-C-wt, but not CTR-CΔESS or C, pulled ZO-1 immu-noreactivity down.

Example 23

Disruption of ZO-1-CTR Interaction by Blocking the Action of CTR.

Multiple lines of evidence described above show that CTR-ZO-1 interaction through the PDZ domain of ZO-1 is critical for destabilization of TJ and the induction of inva-sion in cells and metastasis in animal models resembling human prostate cancer. The evidence also reveals how to develop various types of inhibitors that can block the interaction between CTR and ZO-1. This interaction can also be blocked by using a monoclonal antibody against CTR or CT or by screening and identifying a small molecule antagonist of CTR. Such molecules would act as therapeu-tics and block metastasis in prostate cancer patients by preventing the downstream event of association of CTR and the PDZ binding domain of ZO-1. Development of such fully human or humanized therapeutic antibodies against either CTR or CT is a widely known to anyone skilled in the art and can be employed to develop novel therapeutics. Likewise, small molecule antagonists of CTR which can lead to the abrogation of interaction between ZO-1 and CTR can be developed by combinatorial chemistry and screening techniques or through in-silico modeling, techniques widely used by people skilled in the art.

Example 24

CT and CTR Expression in Other Human Cancers.

To investigate whether CT and CTR are expressed in other human cancers, the expression of CTR (green) and CT (red) was examined using a human cancer tissue microarray. As shown in micrographs of FIG. 24, a remarkable increase in CT- and CTR-immunoreactive cell populations were seen in bladder carcinoma, esophagus cancer, squamous cell carcinoma, adenocarcinomas of lung, ovarian adenocarci-noma, pancreatic carcinoma, and rectal carcinomas. More-over, CT and CTR immunoreactive cells were found in the cell location, indicating that the CT-CTR autocrine axis may be functional in these cancers as observed in prostate adenocarcinomas above.

Next, whether CTR destabilizes tight junctions and increases invasion in these cancers was tested by examining the effect of CT on transepithelial electric resistance (TER), paracellular permeability (PCP) and invasion in cancer cell lines derived from bladder cancer (UMUC3 and RT4), ovarian cancer (A2780 and OVCAR8), and lung cancer (A549). Prostate cancer cell line PC-3CTR was used a reference line. As shown in FIG. 25, CT decreased TER of all these cell lines derived from other cancers similar to its effect on PC-3CTR cells. This was further confirmed by the actions of CT on PCP (FIG. 26A) and cell invasion (FIG. 26B). Interestingly, well-differentiated bladder and ovarian cancer cell lines (RT4 and OVCAR8 respectively) responded poorly to CT as was observed in LNCaP cells, a well-differentiated prostate cancer cell line. In contrast, aggressive cell lines responded extremely well to CT, further confirming a possibility that advanced tumors become more responsive to CT due to overexpression of CTR. Thus, overexpression of CT and CTR and formation of CT-CTR autocrine axis are not unique phenomena found in prostate cancer; but more general phenomena exhibited by multiple epithelial cancers. The role of CT-CTR axis is to destabilize junction complexes and increase invasion in cancers as diverse as prostate, bladder, lung and ovarian cancers. These results further reinforce that CTR-ZO-1 interaction and its impact on cancer metastasis is not a unique phenomenon of prostate cancer, but a more general phenomenon occurring in multiple epithelial cancers.

In addition, CTR expression was retained in tumor cells that metasized from the primary location of the tumor to other body organs. FIG. 27 shows that CTR expression was found in cerebellum cells from the metastatic adenocarci-noma from lung, in femur cells from metastatic adenocar-cinoma from lung, in fiber fatty tissue from metastatic squamous cell carcinoma from larynx, and in lymph node from metastatic adenocarcinoma from lung. These results demonstrate that the interaction of CTR or other growth factor receptors with ZO-1 is important for cancer progres-sion of not only prostate cancer, but several other cancers. Thus prevention of the CTR-ZO-1 interaction can have therapeutic benefits in other cancers, in addition to prostate cancers.

Example 25

Additional Inhibitors of CTR-Zo-1 Interaction

Certain hydantoin-like molecules isolated from sea sponge have been identified that could inhibit prostate cell metastasis (Shah et al., 2009; Mudit et al., 2011). Disruption of junctional complex stabilizes intracellular β-catenin, leading to its translocation in the nucleus, where it can bind to its partner LEF-1 (lymphocyte enhancer binding factor-1) to transactivate target genes. The transcription of TCF/LEF genes can be quantitated by using luciferase-based reporter plasmids, pGL3-OT and pGL3-OF, the improved version of the Topflash and Fopflash vectors (Shah et al., 2009). This assay can be used to comparatively evaluate junction dis-rupting activity of multiple compounds in a single assay. The results of FIG. 28 demonstrate that 50 nM CT caused over 50-fold increase in luciferase activity measured in relative light units (RLU) after normalization with *Renilla* luciferase activity. The results shown in FIG. 28 are means±SEM (n=3). As expected, PMH, an anti-metastatic compound decreased it remarkably. Interestingly, the PMH derivatives, MRM4 and MRM6, were significantly more potent than PMH inhibiting CT action, suggesting they were more potent than PMH in attenuating CT-ZO-1 interaction. Con-sidering that CT-stimulated TCF/LEF transcriptional activ-ity is associated with CTR-mediated junctional destabiliza-tion, the results of FIG. 28 demonstrate that the assay can be used for initial screen of large number of compounds to identify potential anti-metastatic agent. The two com-pounds, MRM-6 and MRM-4, derivatives of PMH whose structures are shown below, were obtained from Dr. K. A. El Sayed. As shown above, MRM-6 ((5Z,5'E)-5,5'-(1,4-phe-nylenebis(methan-1-yl-1-ylidene))diimidazolidine-2,4-di-one (CAS registry number 709620-57-5)) and MRM-4 ((Z)-5-(4-amino-2-chlorobenzylidene)imidazolidine-2,4-dione) were more potent in blocking CTR-ZO-1 interaction-medi-ated TCF/LEF activity than the previously reported com-pounds PMH and S-PMH.

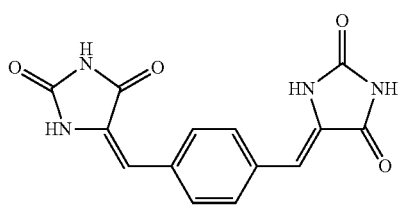

Chemical Formula: $C_{14}H_{10}N_4O_4$
Exact Mass: 298.0702
Migration, WHA PC-3 $IC_{50}$ 5.7 μM
MRM4

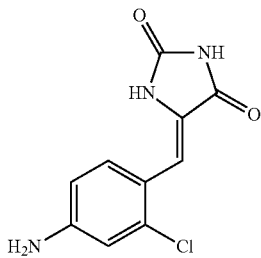

Chemical Formula: $C_{10}H_8ClN_3O_2$
Exact Mass: 237.0305
Migration, WHA PC-3 $IC_{50}$ 9.5 μM
MRM6

REFERENCES

Allalou, A., and Wahlby, C. (2009) *Comput Methods Programs Biomed* 94(1), 58-65

Anderson, J. M., and Van Itallie, C. M. (2008). Tight junctions. Curr Biol 18, R941-943.

Balasubramanian, S., Fam, S. R., and Hall, R. A. (2007). GABAB receptor association with the PDZ scaffold Muppl alters receptor stability and function. J Biol Chem 282, 4162-4171.

Bockaert, J., Dumuis, A., Fagni, L., and Marin, P. (2004). GPCR-GIP networks: a first step in the discovery of new therapeutic drugs? Curr Opin Drug Discov Devel 7, 649-657.

Bockaert, J., Marin, P., Dumuis, A., and Fagni, L. (2003). The 'magic tail' of G protein-coupled receptors: an anchorage for functional protein networks. FEBS Lett 546, 65-72.

Bomberger, J. M., Spielman, W. S., Hall, C. S., Weinman, E. J., and Parameswaran, N. (2005). Receptor activity-modifying protein (RAMP) isoform-specific regulation of adrenomedullin receptor trafficking by NHERF-1. J Biol Chem 280, 23926-23935.

Brennan, K., Offiah, G., McSherry, E. A., and Hopkins, A. M. Tight junctions: a barrier to the initiation and progression of breast cancer? J Biomed Biotechnol 2010, 460607.

Chen, M., Philipp, M., Wang, J., Premont, R. T., Garrison, T. R., Caron, M. G., Lefkowitz, R. J., and Chen, W. (2009). G Protein-coupled receptor kinases phosphorylate LRP6 in the Wnt pathway. J Biol Chem 284, 35040-35048.

Chien, J., and Shah, G. V. (2001) *Int J Cancer* 91(1), 46-54.

Chien, J., Ren, Y., Qing Wang, Y., Bordelon, W., Thompson, E., Davis, R., Rayford, W., and Shah, G. (2001a). Calcitonin is a prostate epithelium-derived growth stimulatory peptide. Mol Cell Endocrinol 181, 69-79.

Chien, J., Ren, Y., Qing Wang, Y., Bordelon, W., Thompson, E., Davis, R., Rayford, W., and Shah, G. (2001b). Calcitonin is a prostate epithelium-derived growth stimulatory peptide. Mol Cell Endocrinol 181, 69-79.

Chien, J., Wong, E., Nikes, E., Noble, M. J., Pantazis, C. G., and Shah, G. V. (1999a). Constitutive activation of stimulatory guanine nucleotide binding protein (G(S)alphaQL)-mediated signaling increases invasiveness and tumorigenicity of PC-3M prostate cancer cells. Oncogene 18, 3376-3382.

Chien, J., Wong, E., Nikes, E., Noble, M. J., Pantazis, C. G., and Shah, G. V. (1999b). Constitutive activation of stimulatory guanine nucleotide binding protein (G(S)alphaQL)-mediated signaling increases invasiveness and tumorigenicity of PC-3M prostate cancer cells. Oncogene 18, 3376-3382.

Chigurupati, S., Kulkarni, T., Thomas, S., and Shah, G. (2005). Calcitonin stimulates multiple stages of angiogenesis by directly acting on endothelial cells. Cancer Res 65, 8519-8529.

Conner, A. C., Simms, J., Hay, D. L., Mahmoud, K., Howitt, S. G., Wheatley, M., and Poyner, D. R. (2004). Heterodimers and family-B GPCRs: RAMPs, CGRP and adrenomedullin. Biochem Soc Trans 32, 843-846.

Danielpour, D. (1999) *J Cell Sci* 112 (Pt 2), 169-179

Demirgoz, D., A. Garg, et al. (2008). PR_b-targeted PEGylated liposomes for prostate cancer therapy. Langmuir 24(23): 13518-13524.

Denker, B. M., and Nigam, S. K. (1998). Molecular structure and assembly of the tight junction. Am J Physiol 274, F1-9.

De Flora, S., A. Izzotti, et al. (2001). "Multiple points of intervention in the prevention of cancer and other mutation-related diseases." Mutat Res 480-481: 9-22.

Dong, M., Pinon, D. I., Cox, R. F., and Miller, L. J. (2004). Importance of the amino terminus in secretin family G protein-coupled receptors. Intrinsic photoaffinity labeling establishes initial docking constraints for the calcitonin receptor. J Biol Chem 279, 1167-1175.

Egerton, M., Needham, M., Evans, S., Millest, A., Cerillo, G., McPheat, J., Popplewell, M., Johnstone, D., and Hollis, M. (1995). Identification of multiple human calcitonin receptor isoforms: heterologous expression and pharmacological characterization. J Mol Endocrinol 14, 179-189.

Elliott, G., and O'Hare, P. (1997). Intercellular trafficking and protein delivery by a herpesvirus structural protein. Cell 88, 223-233.

Fanning, A. S., Jameson, B. J., Jesaitis, L. A., and Anderson, J. M. (1998). The tight junction protein ZO-1 establishes a link between the transmembrane protein occludin and the actin cytoskeleton. J Biol Chem 273, 29745-29753.

Fanning, A. S., Ma, T. Y., and Anderson, J. M. (2002). Isolation and functional characterization of the actin binding region in the tight junction protein ZO-1. Faseb J 16, 1835-1837.

Findlay, D. M., Raggatt, L. J., Bouralexis, S., Hay, S., Atkins, G. J., and Evdokiou, A. (2002) *J Endocrinol* 175(3), 715-725

Findlay, D. M. (2006). Regulation of cell growth mediated by the calcitonin receptor. Cell Mol Biol (Noisy-le-grand) 52, 3-8.

Gage, R. M., Matveeva, E. A., Whiteheart, S. W., and von Zastrow, M. (2005). Type I PDZ ligands are sufficient to promote rapid recycling of G Protein-coupled receptors independent of binding to N-ethylmaleimide-sensitive factor. J Biol Chem 280, 3305-3313.

Gardner, L. A., Tavalin, S. J., Goehring, A. S., Scott, J. D., and Bahouth, S. W. (2006). AKAP79-mediated targeting of the cyclic AMP-dependent protein kinase to the beta1-adrenergic receptor promotes recycling and functional resensitization of the receptor. J Biol Chem 281, 33537-33553.

Golemis, E. A., Serebriiskii, I., Finley, R. L., Jr., Kolonin, M. G., Gyuris, J., and Brent, R. (2001). Interaction trap/two-hybrid system to identify interacting proteins. Curr Protoc Cell Biol Chapter 17, Unit 17 13.

Gonzalez-Mariscal, L., Tapia, R., and Chamorro, D. (2008) *Biochim Biophys Acta* 1778(3), 729-756

Gonzalez-Mariscal, L., Betanzos, A., and Avila-Flores, A. (2000) *Semin Cell Dev Biol* 11(4), 315-324

Hall, R. A. (2004). Studying protein-protein interactions via blot overlay or Far Western blot. Methods Mol Biol 261, 167-174.

Hall, R. A., Premont, R. T., and Lefkowitz, R. J. (1999). Heptahelical receptor signaling: beyond the G protein paradigm. J Cell Biol 145, 927-932.

Hatakeyama, H., H. Akita, et al. (2007). Development of a novel systemic gene delivery system for cancer therapy with a tumor-specific cleavable PEG-lipid. Yakugaku Zasshi 127(10): 1549-1556.

Huang, C. L., Sun, L., Moonga, B. S., and Zaidi, M. (2006). Molecular physiology and pharmacology of calcitonin. Cell Mol Biol (Noisy-le-grand) 52, 33-43.

Hurd, T. W., Gao, L., Roh, M. H., Macara, I. G., and Margolis, B. (2003). Direct interaction of two polarity complexes implicated in epithelial tight junction assembly. Nat Cell Biol 5, 137-142.

Kachar, B., and Reese, T. S. (1983) *J Ultrastruct Res* 82(1), 90-95

Karpova, T., and McNally, J. G. (2006). Detecting protein-protein interactions with CFP-YFP FRET by acceptor photobleaching. Curr Protoc Cytom Chapter 12, Unit12 17.

Katafuchi, T., Yasue, H., Osaki, T., and Minamino, N. (2009). Calcitonin receptor-stimulating peptide: Its evolutionary and functional relationship with calcitonin/calcitonin gene-related peptide based on gene structure. Peptides 30, 1753-1762.

Kim, J. H., Y. S. Kim, et al. (2008). Self-assembled glycol chitosan nanoparticles for the sustained and prolonged delivery of antiangiogenic small peptide drugs in cancer therapy. Biomaterials 29(12): 1920-1930.

Kohler, K., and Zahraoui, A. (2005) *Biol Cell* 97(8), 659-665

Kolonin, M. G., Zhong, J., and Finley, R. L. (2000). Interaction mating methods in two-hybrid systems. Methods Enzymol 328, 26-46.

Leve, F., de Souza, W., and Morgado-Diaz, J. A. (2008) *J Pharmacol Exp Ther* 327(3), 777-788

Li, Y., Fanning, A. S., Anderson, J. M., and Lavie, A. (2005). Structure of the conserved cytoplasmic C-terminal domain of occludin: identification of the ZO-1 binding surface. J Mol Biol 352, 151-164.

Liao, J., L. K. McCauley. (2006). Skeletal metastasis: established and emerging roles of parathyroid hormone related protein (PTHrP); Cancer Metastasis Rev., 25(4), 559-571.

Lupp, A., Klenk, C., Rocken, C., Evert, M., Mawrin, C., Schulz, S. (2010). Immunohistochemical identification of the PTHR1 parathyroid hormone receptor in nomal and neoplastic human tissues. Eur. J. Endocrinol. 162, 979-986.

Mahon, M. J. (2009). The parathyroid hormone 1 receptor directly binds to the FERM domain of ezrin, an interaction that supports apical receptor localization and signaling in LLC-PK1 cells. Mol Endocrinol 23, 1691-1701.

Martin, T. A., and Jiang, W. G. (2009). Loss of tight junction barrier function and its role in cancer metastasis. Biochim Biophys Acta 1788, 872-891.

Martin, T. A., Watkins, G., Mansel, R. E., and Jiang, W. G. (2004). Loss of tight junction plaque molecules in breast cancer tissues is associated with a poor prognosis in patients with breast cancer. Eur J Cancer 40, 2717-2725.

Morin, P. J. (2007). Claudin proteins in ovarian cancer. Dis Markers 23, 453-457.

Mudit, M., and El Sayed, K. A. (2011) Optimization of (Phenylmethylidene)-hydantoins as prostate cancer migration inhibitors: SAR-directed design, synthesis, and pharmacophore modeling. Chem. Biodiv. 8, 1470-1485.

Nussenzveig, D. R., Mathew, S., and Gershengorn, M. C. (1995). Alternative splicing of a 48-nucleotide exon generates two isoforms of the human calcitonin receptor. Endocrinology 136, 2047-2051.

Pan, H., N. R. Soman, et al. (2011). Cytolytic peptide nanoparticles ('NanoBees') for cancer therapy. Wiley Interdiscip Rev Nanomed Nanobiotechnol 3(3): 318-327.

Purdue, B. W., Tilakaratne, N., and Sexton, P. M. (2002). Molecular pharmacology of the calcitonin receptor. Receptors Channels 8, 243-255.

Reuther, G., K. T. Tan, et al. (2006). Structural model of the membrane-bound C terminus of lipid-modified human N-ras protein. Angew Chem Int Ed Engl 45(32): 5387-5390.

Ritchie, C. K., Thomas, K. G., Andrews, L. R., Tindall, D. J., and Fitzpatrick, L. A. (1997) *Prostate* 30(3), 183-187

Sabbisetti, V. S., Chirugupati, S., Thomas, S., Vaidya, K. S., Reardon, D., Chiriva-Internati, M., Iczkowski, K. A., and Shah, G. V. (2005). Calcitonin increases invasiveness of prostate cancer cells: role for cyclic AMP-dependent protein kinase A in calcitonin action. Int J Cancer 117, 551-560.

Sanger, F., Nicklen, S., and Coulson, A. R. (1992). DNA sequencing with chain-terminating inhibitors. 1977. Biotechnology 24, 104-108.

Shah, G. V. (2009). Calcitonin. Encyclopedia of Cancer 2, 16-20.

Shah G V, C.-I., Maurizio (2003). Cancer cells and pro-growth/prosurvival signaling. In: Encyclopedia of Hormones and related cell regulators, P. M. Conn, ed. (Oxford, UK: Academic Press), pp. 246-254.

Shah, G. V., Muralidharan, A., Gokulgandhi, M., Soan, K., and Thomas, S. (2009a). Cadherin switching and activation of beta-catenin signaling underlie proinvasive actions of calcitonin-calcitonin receptor axis in prostate cancer. J Biol Chem 284, 1018-1030.

Shah, G. V., Muralidharan, A., Thomas, S., Gokulgandhi, M., Mudit, M., Khanfar, M., and El Sayed, K. (2009b). Identification of a small molecule class to enhance cell-cell adhesion and attenuate prostate tumor growth and metastasis. Mol Cancer Ther 8, 509-520.

Shah, G. V., Noble, M. J., Austenfeld, M., Weigel, J., Deftos, L. J., and Mebust, W. K. (1992). Presence of calcitonin-like immunoreactivity (iCT) in human prostate gland: evidence for iCT secretion by cultured prostate cells. Prostate 21, 87-97.

Shah, G. V., Rayford, W., Noble, M. J., Austenfeld, M., Weigel, J., Vamos, S., and Mebust, W. K. (1994). Calcitonin stimulates growth of human prostate cancer cells through receptor-mediated increase in cyclic adenosine 3',5'-monophosphates and cytoplasmic Ca2+ transients. Endocrinology 134, 596-602.

Shah, G. V., Thomas, S., Muralidharan, A., Liu, Y., Hermonat, P. L., Williams, J., and Chaudhary, J. (2008). Calcitonin promotes in vivo metastasis of prostate cancer cells by altering cell signaling, adhesion, and inflammatory pathways. Endocr Relat Cancer 15, 953-964.

Sheehan, G. M., Kallakury, B. V., Sheehan, C. E., Fisher, H. A., Kaufman, R. P., Jr., and Ross, J. S. (2007). Loss of claudins-1 and -7 and expression of claudins-3 and -4 correlate with prognostic variables in prostatic adenocarcinomas. Hum Pathol 38, 564-569.

Tao, Y. X., and Johns, R. A. (2004). Neuronal PDZ domains: a promising new molecular target for inhaled anesthetics? Mol Interv 4, 215-221.

Thomas, S., Chigurupati, S., Anbalagan, M., and Shah, G. (2006). Calcitonin increases tumorigenicity of prostate cancer cells: evidence for the role of protein kinase A and urokinase-type plasminogen receptor. Mol Endocrinol 20, 1894-1911.

Thomas, S., Muralidharan, A., and Shah, G. V. (2007). Knock-down of calcitonin receptor expression induces apoptosis and growth arrest of prostate cancer cells. Int J Oncol 31, 1425-1437.

Thomas, S., and Shah, G. (2005). Calcitonin induces apoptosis resistance in prostate cancer cell lines against cytotoxic drugs via the Akt/survivin pathway. Cancer Biol Ther 4, 1226-1233.

Tolcos, M., Tikellis, C., Rees, S., Cooper, M., and Wookey, P. (2003) *J Comp Neurol* 456(1), 29-38

Tovar Sepulveda, V. A., Falzon, M. (2002) Parathyroid hormone-related protein enhances PC-3 prostate cancer cell growth via both autocrine/paracrine and intracrine pathways. Regul. Pept. 105, 109-120.

Van Itallie, C. M., and Anderson, J. M. (2004). The role of claudins in determining paracellular charge selectivity. Proc Am Thorac Soc 1, 38-41.

von Zastrow, M., and Kobilka, B. K. (1994) *J Biol Chem* 269(28), 18448-18452

Wang, M. D., D. M. Shin, et al. (2007). Nanotechnology for targeted cancer therapy. Expert Rev Anticancer Ther 7(6): 833-837.

Wu, G., Burzon, D. T., di Sant'Agnese, P. A., Schoen, S., Deftos, L. J., Gershagen, S., and Cockett, A. T. (1996) Urology 47(3), 376-381

Zahraoui, A. (2004). [Tight junctions, a platform regulating cell proliferation and polarity]. Med Sci (Paris) 20, 580-585.

Zhang, X., L. Collins, et al. (2001). A powerful cooperative interaction between a fusogenic peptide and lipofectamine for the enhancement of receptor-targeted, non-viral gene delivery via integrin receptors. J Gene Med 3(6): 560-568.

Zhu, Y., and Sundfeldt, K. (2007). Tight junction formation in epithelial ovarian adenocarcinoma. Acta Obstet Gynecol Scand 86, 1011-1019.

The complete disclosures of all references cited in the specification are hereby incorporated by reference. In the event of an otherwise irreconcilable conflict, however, the present specification shall control.

---

What is claimed:

1. A method to inhibit metastasis in a cancerous solid tumor with tumor cells that have a receptor with a C-terminal PDZ binding motif, and for which metastasis depends on disassembly of cellular tight junctions; said method comprising administering a therapeutic amount of a peptide selected from the group consisting of a peptide whose amino acid sequence has 90% or greater sequence identity with SEQ ID NO:2, and a peptide whose amino acid sequence has 90% or greater sequence identity with SEQ ID NO:3; wherein each amino acid, if any, in said peptide that is not identical to the corresponding amino acid of SEQ ID NO:2 or SEQ ID NO:3 is a conservative substitution; wherein said peptide inhibits interaction between the tumor cell receptor's PDZ binding motif and the PDZ motif of zonula occludens-1; whereby the disassembly of cellular tight junctions of the tumor cells is inhibited; whereby metastasis of the tumor is inhibited.

2. The method of claim 1, wherein the receptor is a calcitonin receptor.

3. The method of claim 1, wherein the compound is a peptide whose amino acid sequence has 90% or greater sequence identity with SEQ ID NO:2.

4. The method of claim 1, wherein the compound is a peptide whose amino acid sequence has 90% or greater sequence identity with SEQ ID NO:3.

5. The method of claim 1, wherein the tumor cells express zonula occludens-1 having a PDZ domain with an amino acid sequence selected from the group consisting of SEQ ID NO:9, SEQ ID NO:10, and SEQ ID NO:11.

6. The method of claim 5, wherein the PDZ domain of zonula occludens-1 has the amino acid sequence SEQ ID NO:11.

7. The method of claim 1, wherein the cancerous tumor is selected from the group consisting of prostate carcinoma, bladder carcinoma, esophagus cancer, squamous cell carcinoma, adenocarcinomas of lung, ovarian adenocarcinoma, pancreatic carcinoma, and rectal carcinoma.

8. The method of claim 1, wherein the cancerous tumor is prostate carcinoma.

9. The method of claim 1, wherein the compound is a peptide whose amino acid sequence is SEQ ID NO:2.

10. The method of claim 1, wherein the compound is a peptide whose amino acid sequence is SEQ ID NO:3.

11. The method of claim 1, wherein the cancerous tumor is prostate carcinoma, and wherein the compound is a peptide whose amino acid sequence is SEQ ID NO:2.

12. The method of claim 1, wherein the cancerous tumor is prostate carcinoma, and wherein the compound is a peptide whose amino acid sequence is SEQ ID NO:3.

13. The method of claim 5, wherein the PDZ domain of zonula occludens-1 has the amino acid sequence SEQ ID NO:9.

14. The method of claim 5, wherein the PDZ domain of zonula occludens-1 has the amino acid sequence SEQ ID NO:10.

* * * * *

SEQUENCE LISTING

```
<160> NUMBER OF SEQ ID NOS: 11

<210> SEQ ID NO 1
<211> LENGTH: 4
<212> TYPE: PRT
<213> ORGANISM: Homo sapiens

<400> SEQUENCE: 1

Glu Ser Ser Ala
1

<210> SEQ ID NO 2
<211> LENGTH: 18
<212> TYPE: PRT
<213> ORGANISM: Artificial sequence
<220> FEATURE:
<223> OTHER INFORMATION: Synthetic peptide

<400> SEQUENCE: 2

Glu Gln Glu Ser Ser Ala Ala Tyr Gly Arg Lys Lys Arg Arg Gln Arg
1               5                  10                  15

Arg Arg

<210> SEQ ID NO 3
<211> LENGTH: 19
<212> TYPE: PRT
<213> ORGANISM: Artificial sequence
<220> FEATURE:
<223> OTHER INFORMATION: Synthetic peptide

<400> SEQUENCE: 3

Ile Ile Glu Gln Glu Ser Ser Ala Tyr Gly Arg Lys Lys Arg Arg Gln
1               5                  10                  15

Arg Arg Arg
```

```
<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Ala Ala Ala Ala
1

<210> SEQ ID NO 5
<211> LENGTH: 60
<212> TYPE: DNA
<213> ORGANISM: Artificial sequence
<220> FEATURE:
<223> OTHER INFORMATION: Synthetic primer

<400> SEQUENCE: 5
aagcttatgg actacaagga cgacgatgac aagagcttca catttacaag ccggtgcttg    60

<210> SEQ ID NO 6
<211> LENGTH: 51
<212> TYPE: DNA
<213> ORGANISM: Artificial sequence
<220> FEATURE:
<223> OTHER INFORMATION: Synthetic primer

<400> SEQUENCE: 6
ctcgagtcaa gcagatgact cttgctctat gatattcaaa gggatgatct c              51

<210> SEQ ID NO 7
<211> LENGTH: 51
<212> TYPE: DNA
<213> ORGANISM: Artificial sequence
<220> FEATURE:
<223> OTHER INFORMATION: Synthetic primer

<400> SEQUENCE: 7
ctcgagtcaa gcagcagcag cttgctctat gatattcaaa gggatgatct c              51

<210> SEQ ID NO 8
<211> LENGTH: 21
<212> TYPE: DNA
<213> ORGANISM: Artificial sequence
<220> FEATURE:
<223> OTHER INFORMATION: Synthetic primer

<400> SEQUENCE: 8
gacgagauaa uccucauuut t                                               21

<210> SEQ ID NO 9
<211> LENGTH: 88
<212> TYPE: PRT
<213> ORGANISM: Homo sapiens

<400> SEQUENCE: 9

Thr Val Thr Leu His Arg Ala Pro Gly Phe Gly Phe Gly Ile Ala Ile
1               5                   10                  15

Ser Gly Gly Arg Asp Asn Pro His Phe Gln Ser Gly Glu Thr Ser Ile
            20                  25                  30

Val Ile Ser Asp Val Leu Lys Gly Gly Pro Ala Glu Gly Gln Leu Gln
        35                  40                  45
```

```
Glu Asn Asp Arg Val Ala Met Val Asn Gly Val Ser Met Asp Asn Val
    50                  55                  60

Glu His Ala Phe Ala Val Gln Gln Leu Arg Lys Ser Gly Lys Asn Ala
65                  70                  75                  80

Lys Ile Thr Ile Arg Arg Lys Lys
                85

<210> SEQ ID NO 10
<211> LENGTH: 79
<212> TYPE: PRT
<213> ORGANISM: Homo sapiens

<400> SEQUENCE: 10

Lys Val Thr Leu Val Lys Ser Arg Lys Asn Glu Glu Tyr Gly Leu Arg
1               5                   10                  15

Leu Ala Ser His Ile Phe Val Lys Glu Ile Ser Gln Asp Ser Leu Ala
                20                  25                  30

Ala Arg Asp Gly Asn Ile Gln Glu Gly Asp Val Val Leu Lys Ile Asn
            35                  40                  45

Gly Thr Val Thr Glu Asn Met Ser Leu Thr Asp Ala Lys Thr Leu Ile
        50                  55                  60

Glu Arg Ser Lys Gly Lys Leu Lys Met Val Val Gln Arg Asp Glu
65                  70                  75

<210> SEQ ID NO 11
<211> LENGTH: 82
<212> TYPE: PRT
<213> ORGANISM: Homo sapiens

<400> SEQUENCE: 11

Ser Met Lys Leu Val Lys Phe Arg Lys Gly Asp Ser Val Gly Leu Arg
1               5                   10                  15

Leu Ala Gly Gly Asn Asp Val Gly Ile Phe Val Ala Gly Val Leu Glu
                20                  25                  30

Asp Ser Pro Ala Ala Lys Glu Gly Leu Glu Glu Gly Asp Gln Ile Leu
            35                  40                  45

Arg Val Asn Asn Val Asp Phe Thr Asn Ile Ile Arg Glu Glu Ala Val
        50                  55                  60

Leu Phe Leu Leu Asp Leu Pro Lys Gly Glu Glu Val Thr Ile Leu Ala
65                  70                  75                  80

Gln Lys
```